United States Patent
Honda et al.

(10) Patent No.: US 12,285,475 B2
(45) Date of Patent: Apr. 29, 2025

(54) BACTERIUM CAPABLE OF INDUCING TH1 CELLS

(71) Applicant: KEIO UNIVERSITY, Tokyo (JP)

(72) Inventors: Kenya Honda, Tokyo (JP); Koji Atarashi, Tokyo (JP); Seiko Narushima, Tokyo (JP); Wataru Suda, Tokyo (JP); Masahira Hattori, Tokyo (JP)

(73) Assignee: KEIO UNIVERSITY, Tokyo (JP)

(*) Notice: Subject to any disclaimer, the term of this patent is extended or adjusted under 35 U.S.C. 154(b) by 1386 days.

(21) Appl. No.: 16/346,782

(22) PCT Filed: Nov. 1, 2017

(86) PCT No.: PCT/JP2017/039522
§ 371 (c)(1),
(2) Date: Jul. 29, 2019

(87) PCT Pub. No.: WO2018/084172
PCT Pub. Date: May 11, 2018

(65) Prior Publication Data
US 2023/0293656 A1 Sep. 21, 2023

Related U.S. Application Data

(60) Provisional application No. 62/533,844, filed on Jul. 18, 2017, provisional application No. 62/415,759, filed on Nov. 1, 2016.

(51) Int. Cl.
*A61K 39/02* (2006.01)
*A61K 39/108* (2006.01)
*A61K 39/39* (2006.01)
*A61P 37/04* (2006.01)
*G01N 33/50* (2006.01)
*A61K 39/00* (2006.01)

(52) U.S. Cl.
CPC .......... *A61K 39/0266* (2013.01); *A61K 39/39* (2013.01); *A61P 37/04* (2018.01); *G01N 33/5044* (2013.01); *A61K 2039/52* (2013.01); *A61K 2039/57* (2013.01)

(58) Field of Classification Search
None
See application file for complete search history.

(56) References Cited

U.S. PATENT DOCUMENTS

2009/0130072 A1  5/2009  Lemieux et al.

FOREIGN PATENT DOCUMENTS

JP  2011-200211 A  10/2011
JP  2011200211  *  10/2011

OTHER PUBLICATIONS

Moyat et al World J Gastroenterol. May 21, 2014; 20(19): 5583-5593.*
Mattapallil et al (Gastoenterology. vol. 118, Issue 2, Feb. 2000, pp. 307-315.*
Salcedo et al (Arch Intern Med. 1998;158(8):842-851. doi:10.1001/archinte.158.8.842.*
Anderl et al.(Antimicrob. Agents and Chemotherapy. Jul. 2000. 44(7): 1818-1824).*
Rashid et al (Int. J. Rheumatol. Article ID 610393, "The Role of Klebsiella in Crohn's Disease with a Potential for the Use of Antimicrobial Measures" Oct. 2013. pp. 1-8).*
Notification of Reason for Refusal, dated Oct. 28, 2021, issued by the Japanese Patent Office in JP Application No. 2018-549032.
Decision of Refusal, dated Apr. 4, 2022, issued by the Japanese Patent Office in Japanese Application No. 2018-549032.
Evrard et al., "Roles of Capsule and Lipopolysaccharide O Antigen in Interactions of Human Monocyte-Derived Dendritic Cells and *Klebsiella pneumoniae*", Infection and Immunity, Jan. 2010, pp. 210-219, vol. 78, No. 1.
Kant et al., "Immunostimulatory CpG motifs in the genomes of gut bacteria and their role in human health and disease", Journal of Medical Microbiology, 2014, pp. 293-308, vol. 63.
Morita et al., "Infection defensing function of Lactobacillus reuteri and knowledge about its mechanism" Food Industry, 2010, pp. 67-71, p. 68, vol. 54, No. 2.
Chen et al., "Recombinant outer membrane protein: a potential candidate for Th17 based vaccine against *Klebsiella pneumoniae*. (VAC7P.967)," The Journal of Immunology, 2014, vol. 192, 1 Supplement.
Kamada et al., "Innate immunity in development of inflammatory bowel diseases", Cell Technology, 2008, pp. 770-774, abstract, vol. 27, No. 8.
Ono et al., "Signal from gut tube, New aspect 1. Gut immunity and intestinal flora multi omics analysis", The Lipid, 2012, pp. 52-58, vol. 23, No. 3.
"Anything else, Make an approach to clinical allergy-Immune modification and anti-allergic effect of 465 probiotics lactobacillus, lactobacillus gasseri TMC0356 strain", The Allergy in Practice, non-official translation, 2005, pp. 983-988, abstract, No. 338.
Atarashi et al., "Ectopic colonization of oral bacteria in the intestine drives TH1 cell induction and inflammation", Science, Oct. 20, 2017, pp. 359-365, vol. 358.
Braat et al., Dichotomy between *Lactobacillus rhamnosus* and *Klebsiella pneumoniae* on dendritic cell phenotype and function, J. Mol. Med., 2004, pp. 197-205, vol. 82.
Braun et al., "Rheumatologic manifestations of gastrointestinal disorders", Curr. Opin. Rheumatol., 1999, pp. 68-74, abstract, vol. 11, No. 1.

(Continued)

Primary Examiner — Jennifer E Graser
(74) Attorney, Agent, or Firm — Sughrue Mion, PLLC

(57) ABSTRACT

The result of orally administering saliva derived from a Crohn's disease patient or an ulcerative colitis patient to germ-free mice has revealed that Th1 cells markedly increased in the colons. Further, from the bacterial microbiota in the intestines of the mice in which such an increase in Th1 cells were observed, bacteria have been successfully isolated which caused strong Th1 cell induction in the colon upon intestinal colonization.

4 Claims, 55 Drawing Sheets

Specification includes a Sequence Listing.

(56) References Cited

OTHER PUBLICATIONS

Atarashi et al., "Elucidation for activation mechanism of gut immunity by oral bacteria," FORUM 2016 Pharmaceutical Health Science Environmental Toxicology abstracts, Aug. 29, 2016, p. 134, entire text, non-official translation.

Broberg et al., "Whole-Genome Draft Sequences of Three Multidrug-Resistant Klebsiella pneumoniae Strains Available from the American Type Culture Collection," Genome Announc., 2013, vol. 1, No., 3, e00312-13, entire text.

Lozupone et al., "Alterations in the Gut Microbiota Associated with HIV-1 Infection," Cell Host & Microbe, Sep. 11, 2013, pp. 329-339, vol. 14.

Gevers et al., "The treatment-naive microbiome in new-onset Crohn's disease," Cell Host Microbe. Mar. 12, 2014, pp. 382-392, vol. 15, No. 3.

Chen et al., "Dysbiosis of small intestinal microbiota in liver cirrhosis and its association with etiology," Nat. Scientific Reports, 2016, pp. 1-9.

Sears et al., "Microbes, Microbiota, and Colon Cancer," Cell Host & Microbe, Mar. 12, 2014, pp. 317-328, vol. 15.

Qin et al., "Alterations of the human gut microbiome in liver cirrhosis," Nature, Sep. 4, 2014, pp. 59-64, vol. 513.

Vujkovic-Cvijin et al., "Dysbiosis of the Gut Microbiota Is Associated with HIV Disease Progression and Tryptophan Catabolismo" Science Translational Medicine, Jul. 10, 2013, pp. 1-14, vol. 5, Issue 193.

International Search Report for PCT/JP2017/039522 dated Jan. 23, 2018 [PCT/ISA/210].

Australian Patent Office, Communication issued Mar. 24, 2023 in Australian Application No. 2017354716.

Rasheed et al., "Characterization of the Extended-Spectrum ß-Lactamase Reference Strain, Klebsiella pneumoniae K6 (ATCC 700603), Which Produces the Novel Enzyme SHV-18", Antimicrobial Agents and Chemotherapy, Sep. 2000, p. 2382-2388, vol. 44, No. 9.

Nobuhiko Kamada, et al., "Role of the gut microbiota in immunity and inflammatory disease", Nature Reviews, Immunology, vol. 13, May 2013, pp. 321-335 (15 pages).

In-Ah LEE et al., "Klebsiella pneumoniae increases the risk of inflammation and colitis in a murine model of intestinal bowel disease", Scandinavian Journal of Gastroenterology, 2011, vol. 46, pp. 684-693 (11 pages).

Seydina M. Diene et al., "The Rhizome of the Multidrug-Resistant Enterobacter aerogenes Genome Reveals How New "Killer Bugs" Are Created because of a Sympatric Lifestyle", Mol. Biol. Evol., 2012, vol. 30, No. 2, pp. 369-383 (15 pages total).

Anne Davin-Regli et al., "Enterobacter aerogenes and Enterobacter cloacae; versatile bacterial pathogens confronting antibiotic treatment", Frontiers in Microbiology, 2015, vol. 6, Article 392, pp. 1-10 (10 pages total).

Taha Rashid, "Gut-mediated and HLA-B27-associated Arthritis: An Emphasis on Ankylosing Spondylitis and Crohn's Disease with a Proposal for the Use of New Treatment", Discovery Medicine, 2011, vol. 12, No. 64, pp. 187-194 (10 pages total).

Wang, H. et al., "Increased biofilm formation ability in Klebsiella pneumoniae after short-term exposure to a simulated microgravity environment", MicrobiologyOpen, 2016, vol. 5, No. 5, pp. 793-801.

Australian Office Action dated Nov. 22, 2023 issued by the Australian Patent Office in Australian Application No. 2017354716.

\* cited by examiner

Fig. 53

| KO | Uniprot | Gene category | Annotation |
|---|---|---|---|
| K00971 | | Fructose and mannose metabolism | Mannose-1-phosphate guanylyltransferase 1 |
| K11189 | | | Multiphosphoryl transfer protein |
| K02770 | | | PTS system fructose-specific EIIABC component |
| K15778 | | | Phosphomannomutase/phosphoglucomutase |
| K13058 | | | Mannosylfructose-phosphate synthase |
| K00059 | | | 3-oxoacyl-[acyl-carrier-protein] reductase FabG |
| K12995 | | | mannosylfructose syntransferase |
| K00094 | | Galactose metabolism | Galactitol-1-phosphate 5-dehydrogenase |
| K02775 | | | Galactitol permease IIC component |
| K02774 | | | Galactitol-specific phosphotransferase enzyme IIB component |
| K16371 | | | D-tagatose-1,6-bisphosphate aldolase subunit GatZ |
| K08302 | | | Tagatose-6-phosphate kinase |
| K08302 | | | D-tagatose-1,6-bisphosphate aldolase subunit GatY |
| K02775 | | Carbohydrate metabolism | Galactitol permease IIC component |
| K08256 | | | GDP-mannose dependent alpha-(1-2)-phosphatidylinositol mannosyltransferase |
| K00899 | | | L-xylulose/3-keto-L-gulonate kinase |
| K00874 | | | 2-dehydro-3-deoxygluconokinase |
| K00703 | | | Capsular glucan synthase |
| | A0A182AGT5 | | 3-octaprenyl-4-hydroxybenzoate carboxy-lyase partner protein |
| K18800 | | | 2-octaprenylphenol hydroxylase |
| K03182 | | | Phenolic acid decarboxylase subunit C |
| K01572 | | | Oxaloacetate decarboxylase beta chain |
| K01682 | | | Aconitate hydratase 2 |
| | A0A086RU2 | | Putative aldolase LsrF |
| K00625 | | | Putative acetyltransferase |
| | P9A1C7 | | Propanediol utilization protein PduA |
| | A0A0H4WDF2 | | Putative glycosyltransferase EpsF |

Fig. 56
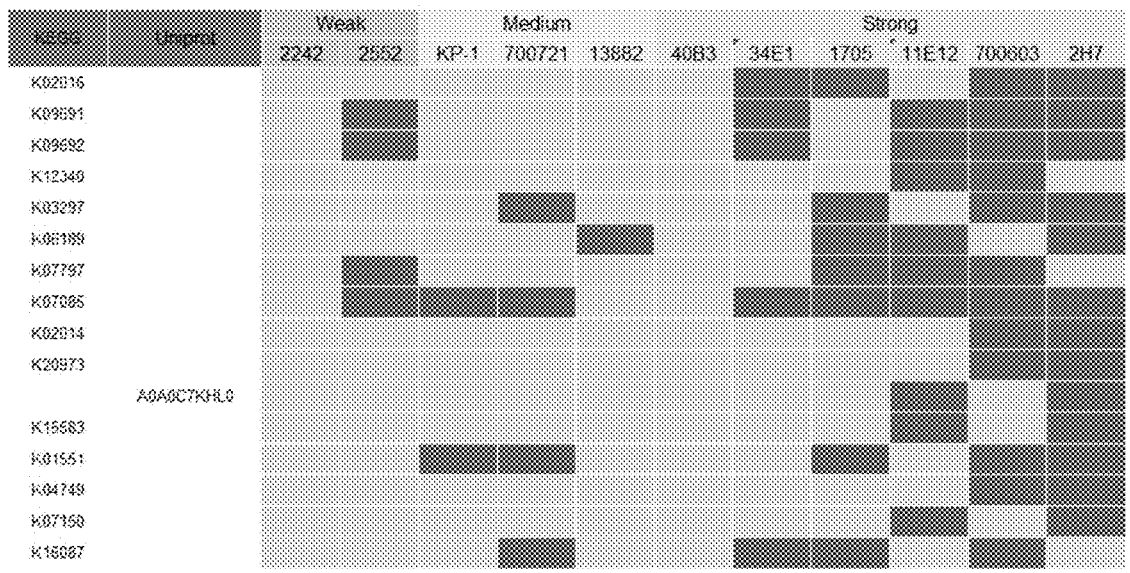
Fig. 57
Fig. 58
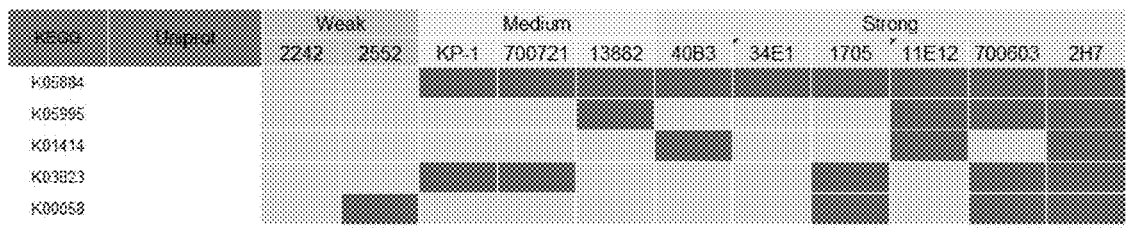

Fig. 59

| KO | Uniprot | Gene category | Annotation |
|---|---|---|---|
| K06218 | | | mRNA interferase RelE |
| K07462 | | | Single-stranded-DNA-specific exonuclease RecJ |
| K04763 | | | Tyrosine recombinase XerD_6 |
| | A0A0C7KGA2 | | Tyrosine recombinase XerD |
| K02468 | | Gene regulator | Glycerol operon repressor |
| K15836 | | | Formate hydrogenlyase transcriptional activator |
| | | | HTH-type transcriptional regulator TsR |
| P07774 | A0A0C7KER5 | | HTH-type transcriptional regulator CatM |
| K07774 | | | Transcriptional regulatory protein tctD |
| K03892 | | | HTH-type transcriptional repressor AseR |
| K13244 | | | Cyclic di-GMP phosphodiesterase YahA |
| K04757 | | | Serine-protein kinase RsbW |

Fig. 60

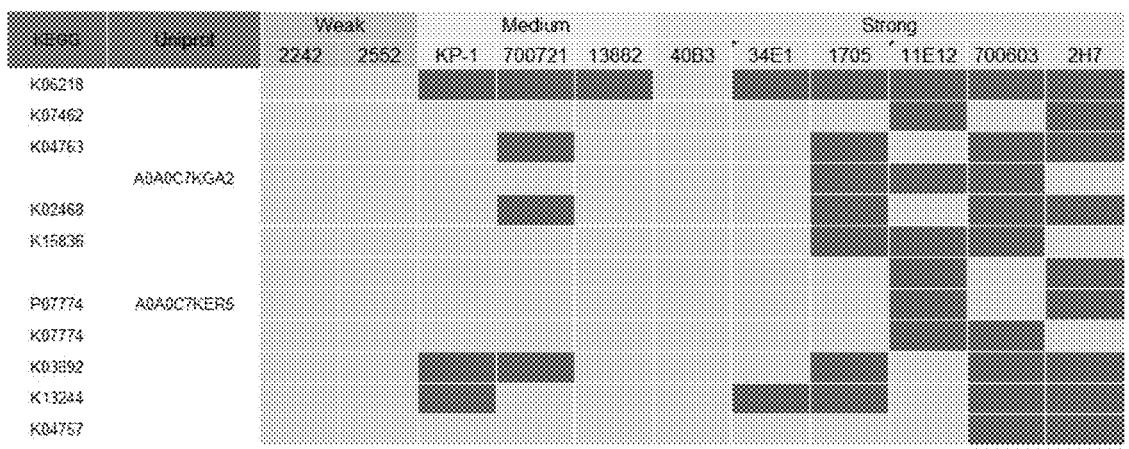

Fig. 61

| KO | Uniprot | Gene category | Annotation |
|---|---|---|---|
| K15125 | | | Filamentous hemagglutinin |
| K18974 | | | Dihydropteroate synthase |
| K01698 | | | Delta-aminolevulinic acid dehydratase |
| | A0A127MKS1 | | Aerobic respiration control protein ArcA |

Fig. 62

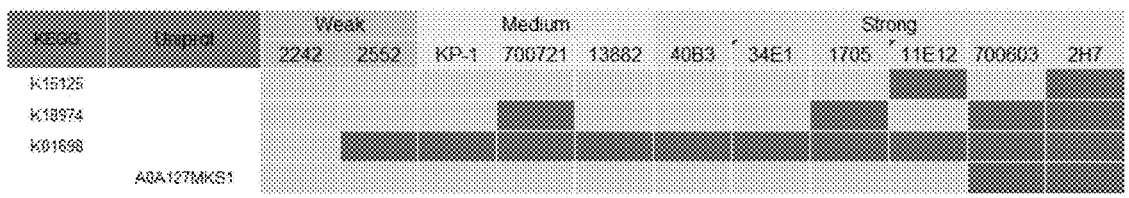

SEQUENCE LISTING

```
<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 1
aatcaagggc ccgagtaagt                                                   20

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 2
ccaaacgcta cgccatttat                                                   20

<210> SEQ ID NO 3
<211> LENGTH: 20
<212> TYPE: DNA
<213> ORGANISM: Artificial Sequence
<220> FEATURE:
```

<223> OTHER INFORMATION: Artificially synthesized primer sequence

<400> SEQUENCE: 3
agcactagcg gctgtggtat                                                    20

<210> SEQ ID NO 4
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 4
acttactcgg gcccttgatt                                                    20

<210> SEQ ID NO 5
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 5
aatcaagggc ccgagtaagt                                                    20

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 6
attcaggggc tgaaggagtt                                                    20

<210> SEQ ID NO 7
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 7
ccatctcatc cctgcgtgtc tccgactcag                                         30

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 8
agrgtttgat ymtggctcag                                                    20

<210> SEQ ID NO 9
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 9
tgctgcctcc cgtaggagt                                                     19

```
<210> SEQ ID NO 10
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 10
ggytaccttg ttacgactt                                                19

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 11
gcgaccagac ctacatgcgt                                               20

<210> SEQ ID NO 12
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 12
agtcgaaaga gcccgcgtc                                                19

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 13
agcactagcg gctgtggtat                                               20

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 14
acttactcgg gcccttgatt                                               20

<210> SEQ ID NO 15
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 15
cttcgccttc atcagcttca                                               20

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized primer sequence
```

```
<400> SEQUENCE: 16
tcatcattaa cgcgggtcag                                              20

<210> SEQ ID NO 17
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 17
ctcatgacca cagtccatgc                                              20

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 18
cacattgggg gtaggaacac                                              20

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 19
tgctggatct ttgctttggc                                              20

<210> SEQ ID NO 20
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 20
agttagctcc gtcacatagt gc                                           22

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 21
aatgccttga agctgatccc                                              20

<210> SEQ ID NO 22
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 22
gttctttgtc atgcgttggc                                              20

<210> SEQ ID NO 23
<211> LENGTH: 22
```

```
<212> TYPE: DNA
<213> ORGANISM: Artificial Sequence
<220> FEATURE:
<223> OTHER INFORMATION: Artificially synthesized primer sequence

<400> SEQUENCE: 23
ggctcattgc ttcagacttt cc                                              22

<210> SEQ ID NO 24
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 24
actgatccat ggcagttacc ag                                              22

<210> SEQ ID NO 25
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 25
atcatcttcc tggagcagtg tg                                              22

<210> SEQ ID NO 26
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 26
ttgttgcaat tggggcttgg                                                 20

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 27
ttggcctttt catccgtcac                                                 20

<210> SEQ ID NO 28
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 28
attcggagca gagacattca gg                                              22

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 29
```
tctccagcgt ttgcaaaacg                                                    20

<210> SEQ ID NO 30
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 30
aaaggtgtgg tttgggctac                                                    20

<210> SEQ ID NO 31
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 31
agaacttgca gctcgtgttg                                                    20

<210> SEQ ID NO 32
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 32
tggttctact tcccaagctt cc                                                 22

<210> SEQ ID NO 33
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 33
acggcacagt cattgaaagc                                                    20

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 34
accatccttt tgccagttcc                                                    20

<210> SEQ ID NO 35
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 35
cctatcccct gtgtgccttg gcagtctcag                                         30

BACTERIUM CAPABLE OF INDUCING TH1 CELLS

This application is a National Stage of International Application No. PCT/JP2017/039522, filed Nov. 1, 2017, which claims the benefit of U.S. Provisional Application No. 62/415,759, filed Nov. 1, 2016, and U.S. Provisional Application No. 62/533,844 filed Jul. 18, 2017.

TECHNICAL FIELD

The present invention has been made as a result of the research based on the entrusted program in the unit-type research area "Innovation for Ideal Medical Treatment Based on the Understanding of Maintenance, Change and Breakdown Mechanisms of Homeostasis among Interacting Organ Systems" (the title of the research and development: "Discovering therapies for Intractable Diseases through the Identification and Characterization of the Gut Microbiota") in Advanced Research and Development programs for Medical Innovation by Japan Agency for Medical Research and Development (AMED) in 2015.

The present invention relates to a bacterium capable of inducing Th1 cell proliferation or activation in an intestine (hereinafter also referred to as "Th1 cell-inducible bacterium"). Moreover, the present invention relates to a composition for activating immunity or a composition for inducing Th1 cell proliferation or activation, the compositions each comprising, as an active ingredient, the Th1 cell-inducible bacterium or a physiologically active substance derived therefrom. Further, the present invention relates to a method for activating immunity or a method for inducing Th1 cell proliferation or activation, the methods each using the Th1 cell-inducible bacterium or a physiologically active substance derived from the Th1 cell-inducible bacterium.

Furthermore, the present invention relates to: a vaccine composition comprising, as an active ingredient, the Th1 cell-inducible bacterium or an antigen specific to the bacterium; or a method for inducing an immune response to the Th1 cell-inducible bacterium in a subject, the method comprising providing the subject with the Th1 cell-inducible bacterium or an antigen specific to the Th1 cell-inducible bacterium.

Moreover, the present invention relates to a composition for suppressing immunity or a composition for suppressing Th1 cell proliferation or activation, the compositions each comprising, as an active ingredient, a substance having an antibacterial activity against the Th1 cell-inducible bacterium, or the like. Further, the present invention relates to a method for suppressing immunity or a method for suppressing Th1 cell proliferation or activation, the methods each using the substance or the like.

Further, the present invention relates to: screening methods for a Th1 cell-inducible bacterium and so forth capable of suppressing or inducing Th1 cell proliferation or activation in an intestine; and a kit or a non-human animal used in the screening methods.

Furthermore, the present invention relates to a composition for testing a disease attributable to Th1 cells, the composition comprising a substance for specifically detecting the Th1 cell-inducible bacterium.

BACKGROUND ART

Diverse indigenous bacteria are present in mucosas of the digestive tract, oral cavity, and so forth, forming a flora as a whole. Indigenous floras play quite major roles in the host physiology and health maintenance. An indigenous floral imbalance is called Dysbiosis, which has been gradually revealed to cause various diseases. It is highly likely that a further progress in the elucidation of mucosal indigenous floras lead to novel disease controls and treatment developments against various diseases. Nevertheless, due to the complexity, the detailed mechanisms have not been sufficiently revealed yet.

A human generates and swallows approximately 1.5 L of saliva every day. Normally, bacteria contained in saliva (oral bacteria) merely pass through the intestinal tract and do not colonize. However, oral bacteria may colonize in the intestinal tract under certain situations. There have been reports that the intestinal colonization of oral bacteria was observed from the early phase of the disease onsets particularly in Crohn's disease, liver cirrhosis, and colorectal cancer. Moreover, it has been known that such colonized oral bacteria influence the disease status (NPLs 1 to 6).

CITATION LIST

Non Patent Literature

[NPL 1] Y. Chen et al., Scientific reports 6, 34055 (2016)
[NPL 2] D. Gevers et al., Cell host & microbe 15, 382-392 (2014)
[NPL 3] C. A. Lozupone et al. Cell host & microbe 14, 329-339 (2013)
[NPL 4] I. Vujkovic-Cvijin et al., Science translational medicine 5, 193ra191 (2013)
[NPL 5] N. Qin et al., Nature 513, 59-64 (2014)
[NPL 6] C. L. Sears, W. S. Garrett, Cell host & microb e 15, 317-328 (2014)

SUMMARY OF INVENTION

Technical Problem

An object to be achieved by the present invention is to provide a bacterium capable of inducing Th1 cell proliferation or activation in an intestine. Another object of the present invention is to identify an oral bacterium which induces Crohn's disease or the like upon intestinal colonization. Consequently, an object of the present invention is to provide, as an example, a composition for treating, alleviating, or preventing a disease such as Crohn's disease by targeting the identified oral bacterium.

Solution to Problem

The present inventors have conducted earnest studies to achieve the above-described objects. As a result, the inventors found out that when salivas derived from some Crohn's disease patients were orally administered to germ-free mice, interferon-gamma (IFN-γ) producing CD4 positive T cells, Th1 cells, markedly increased in the colons (see FIGS. 1 and 2 and so forth). Intestinal bacteria in the mice from which such an increase in Th1 cells was observed were cultured, and eight bacterial strains were successfully isolated (see FIG. 3 and so forth). Next, a mixture solution of the eight bacterial strains was administered to germ-free mice. The result revealed that the mixture was capable of sufficiently inducing Th1 cells (see FIG. 4 and so forth). Further, it was revealed that, among the eight bacterial strains, a 2H7 strain conceivably belonging to *Klebsiella pneumoniae* was capable of sufficiently inducing Th1 cells, even when administered alone to germ-free mice (see FIG. 4 and so forth). On the other hand, a mixture solution of the remaining seven bacterial strains did not induce Th1 cells (see FIG. 4 and so forth). These revealed that the *K. pneumoniae* 2H7 strain present in the saliva of the Crohn's disease patient caused strong induction of Th1 cells in the colon upon intestinal colonization.

Further, among the eight bacterial strains, the *K. pneumoniae* 2H7 strain or an *E. coli* 2B1 strain was allowed to colonize in germ-free IL-10-deficient mice. The result revealed that the colonization by the *K. pneumoniae* 2H7 strain developed more severe colitis than the colonization by the *E. coli* 2B1 strain (see FIG. 17 and so forth). This strongly suggested a possibility that the *K. pneumoniae* 2H7 strain derived from the saliva of the Crohn's disease patient was involved in the development of colitis.

Next, to analyze the mechanism by which the *K. pneumoniae* 2H7 strain induces Th1 cells, the *K. pneumoniae* 2H7 strain was administered to germ-free MyD88/Trif-double deficient mice. As a result, no significant increase in Th1 cells was observed in comparison with wildtype C57BL/6 mice (see FIG. 24 and so forth). This suggested a possibility of the involvement of the signaling pathways of Toll-like receptors, IL-1, and IL-18 in which MyD88/Trif are involved.

Further, whether other strains of *K. pneumoniae* induce colonic Th1 cells similarly or not was studied. The result revealed that increases in Th1 cells by both of a BAA-2552 strain and a 700721 strain purchased from ATCC were significantly low in comparison with the 2H7 strain (see FIG. 21 and so forth). From this, it is conceivable that the *K. pneumoniae* 2H7 strain has a gene and a structure involved in Th1 cell induction, which the BAA-2552 strain and the 700721 strain do not have.

Moreover, it was found out that orally administering saliva of some ulcerative colitis patient to germ-free mice markedly induced Th1 cells in the colons as in the case of the above-described Crohn's disease patients. Further, as a result of identifying a bacterium capable of inducing Th1 cells, an 11E12 strain was found out which is a different strain from the 2H7 strain but belongs to *Klebsiella aeromobilis* closely related to *K. pneumoniae*.

In addition, as a result of progressing the identification of bacteria capable of inducing colonic Th1 cells, a 34E1 strain, a BAA-1705 strain, a 700603 strain, and a 40B3 strain were found out as bacteria capable of inducing colonic Th1 cells as strongly as the 2H7 strain and the 11E12 strain.

Furthermore, the levels of colonic Th1 cells induced and the genome sequences were compared among the above-described bacterial strains belonging to *Klebsiella* (see FIGS. 52 and 23). As a result, as shown in FIGS. 53-62, 64 genes were found out whose functions have been already known and related to the induction of colonic Th1 cells.

Note that FIG. 52 shows annotations of and information (KEGG or UniProt) on genes related to carbohydrate metabolism, among the genes related to the induction of the colonic Th1 cells. FIG. 54 shows the levels of colonic Th1 cells induced by the bacterial strains belonging to *Klebsiella*, and the levels of the genes related to the carbohydrate metabolism the bacterial strains comprise.

FIG. 55 shows annotations of and information (KEGG or UniProt) on genes related to membrane transport, among the genes related to the induction of the colonic Th1 cells. FIG. 56 shows the levels of colonic Th1 cells induced by the bacterial strains belonging to *Klebsiella*, and the levels of the genes related to the membrane transport the bacterial strains comprise.

FIG. 57 shows annotations of and information (KEGG or UniProt) on genes related to amino acid metabolism, among the genes related to the induction of the colonic Th1 cells. FIG. 58 shows the levels of colonic Th1 cells induced by the bacterial strains belonging to *Klebsiella*, and the levels of the genes related to the amino acid metabolism the bacterial strains comprise.

FIG. 59 shows annotations of and information (KEGG or UniProt) on genes related to gene regulation, among the genes related to the induction of the colonic Th1 cells. FIG. 60 shows the levels of colonic Th1 cells induced by the bacterial strains belonging to *Klebsiella*, and the levels of the genes related to the gene regulation the bacterial strains comprise.

FIG. 61 shows annotations of and information (KEGG or UniProt) on other genes than those in FIGS. 53-60, among the genes related to the induction of the colonic Th1 cells. FIG. 62 shows the levels of colonic Th1 cells induced by the bacterial strains belonging to *Klebsiella*, and the levels of the other genes the bacterial strains comprise.

Additionally, it was also revealed that these genes whose functions have been already known include a gene involved in a metabolism of mannose, fructose, or galactose as shown in FIGS. 53 and 54. These findings have led to the completion of the present invention.

Accordingly, the present invention provides the following.

<1> A bacterium capable of inducing Th1 cell proliferation or activation in an intestine.

<2> The bacterium according to <1>, further characterized in that the bacterium belongs to *Klebsiella pneumoniae* or *Klebsiella aeromobilis*.

<3> The bacterium according to <1> or <2>, further characterized in that the bacterium comprises genes encoding at least five proteins selected from the following protein group, a group of proteins:
Mannose-1-phosphate guanylyltransferase 1,
Multiphosphoryl transfer protein,
PTS system fructose-specific EIIABC component,
Phosphomannomutase/phosphoglucomutase,
Mannosylfructose-phosphate synthase,
3-oxoacyl-[acyl-carrier-protein] reductase FabG,
rhamnosyl/mannosyltransferase,
Galactitol-1-phosphate 5-dehydrogenase,
Galactitol permease IIC component,
Galactitol-specific phosphotransferase enzyme IIB component,
D-tagatose-1,6-bisphosphate aldolase subunit Gatz,
Tagatose-6-phosphate kinase,
D-tagatose-1,6-bisphosphate aldolase subunit GatY,
Galactitol permease IIC component,
GDP-mannose-dependent alpha-(1-2)-phosphatidylinositol mannosyltransferase,
L-xylulose/3-keto-L-gulonate kinase,
2-dehydro-3-deoxygluconokinase,
Capsular glucan synthase,
3-octaprenyl-4-hydroxybenzoate carboxy-lyase partner protein,
2-octaprenylphenol hydroxylase,
Phenolic acid decarboxylase subunit C,
Oxaloacetate decarboxylase beta chain,
Aconitate hydratase 2,
Putative aldolase LsrF,
Putative acetyltransferase,
Propanediol utilization protein PduA,
Putative glycosyltransferase EpsF, Hemin-binding periplasmic protein HmuT precursor,
Teichoic acids export ATP-binding protein TagH,
Teichoic acid translocation permease protein TagG,
Outer membrane protein TolC precursor,
Multidrug transporter EmrE,
Magnesium and cobalt efflux protein CorC,
Inner membrane protein YibH,
Aspartate/alanine antiporter,
Ferric enterobactin receptor precursor,
Signal transduction histidine-protein kinase BarA,
Hemolysin transporter protein ShlB precursor,
Oligopeptide transport ATP-binding protein OppD,
Arsenical pump-driving ATPase,
Putative anti-sigma factor antagonist,
Putative membrane protein YdfK,
Putative hemoglobin and hemoglobin-haptoglobin-binding protein 2 precursor,
(2R)-3-sulfolactate dehydrogenase (NADP (+)),
Peptidase E,
Oligopeptidase A,
Phosphinothricin N-acetyltransferase,
Putative 2-hydroxyacid dehydrogenase YoaD,
mRNA interferase RelE,
Single-stranded-DNA-specific exonuclease RecJ,
Tyrosine recombinase XerD_6,
Tyrosine recombinase XerD,
Glucitol operon repressor,
Formate hydrogenlyase transcriptional activator,
HTH-type transcriptional regulator TdfR,
HTH-type transcriptional regulator CatM,
Transcriptional regulatory protein tctD,
HTH-type transcriptional repressor AseR,
Cyclic di-GMP phosphodiesterase YahA,
Serine-protein kinase RsbW,
Filamentous hemagglutinin,
Dihydropteroate synthase,
Delta-aminolevulinic acid dehydratase, and
Aerobic respiration control protein ArcA.

<4> The bacterium according to any one of <1> to <3>, further characterized in that the bacterium comprises a gene involved in a metabolism of at least one saccharide of mannose, fructose, and galactose.
<5> A composition for activating immunity, the composition comprising, as an active ingredient, the bacterium according to any one of <1> to <4> or a physiologically active substance derived from the bacterium.
<6> The composition according to <5>, further characterized in that the composition is for inducing Th1 cell proliferation or activation.
<7> A method for inducing Th1 cell proliferation or activation in a subject, the method comprising providing the subject with the bacterium according to any one of <1> to <4> or a physiologically active substance derived from the bacterium.
<8> A method for activating immunity in a subject, the method comprising providing the subject with the bacterium according to any one of <1> to <4> or a physiologically active substance derived from the bacterium.
<9> A vaccine composition comprising, as an active ingredient, the bacterium according to any one of <1> to <4> or an antigen specific to the bacterium.
<10> A method for inducing an immune response to the bacterium according to any one of <1> to <4> in a subject, the method comprising providing the subject with the bacterium or an antigen specific to the bacterium.
<11> A composition for suppressing immunity, the composition comprising, as an active ingredient, a substance having an antibacterial activity against the bacterium according to any one of <1> to <4> or a substance capable of binding to a physiologically active substance derived from the bacterium according to any one of <1> to <4>.
<12> The composition according to <11>, further characterized in that the composition is for suppressing Th1 cell proliferation or activation.
<13> The composition according to <11> or <12>, further characterized in that the composition is for treating, alleviating, or preventing a disease attributable to Th1 cells.
<14> A method for suppressing Th1 cell proliferation or activation in a subject, the method comprising providing the subject with a substance having an antibacterial activity against the bacterium according to any one of <1> to <4> or a substance capable of binding to a physiologically active substance derived from the bacterium according to any one of <1> to <4>.
<15> A method for suppressing immunity in a subject, the method comprising providing the subject with a substance having an antibacterial activity against the bacterium according to any one of <1> to <4> or a substance capable of binding to a physiologically active substance derived from the bacterium according to any one of <1> to <4>.
<16> A method for treating, alleviating, or preventing a disease attributable to Th1 cells in a subject, the method comprising providing the subject with a substance having an antibacterial activity against the bacterium according to any one of <1> to <4> or a substance capable of binding to a physiologically active substance derived from the bacterium according to any one of <1> to <4>.
<17> A non-human animal comprising the bacterium according to any one of <1> to <4> colonized in an intestine of the animal.
<18> The non-human animal according to <17>, further characterized in that the non-human animal is a non-human model animal of a disease attributable to Th1 cells.
<19> A method for producing the non-human animal according to <17> or <18>, the method comprising the step of providing a non-human animal with the bacterium capable of inducing Th1 cell proliferation or activation in an intestine to allow the bacterium to colonize in an intestine of the animal.
<20> A kit for evaluating Th1 cell proliferation or activation, the kit comprising:
  the bacterium according to any one of <1> to <4>;
  an intestinal epithelial cell; and
  a peripheral blood mononuclear cell.
<21> A kit for evaluating Th1 cell proliferation or activation, the kit comprising:
  an intestinal epithelial cell; and
  a peripheral blood mononuclear cell.
<22> A screening method for a bacterium capable of inducing Th1 cell proliferation or activation in an intestine, the method comprising the steps of:
  providing a non-human germ-free animal with a test sample;
  detecting the number or activity of Th1 cells in an intestine of the non-human germ-free animal; and isolating a bacterium from a sample in the intestine of the non-human germ-free animal from which Th1 cell proliferation or activation is detected in the previous step.

<23> A screening method for a physiologically active substance capable of inducing Th1 cell proliferation or activation in an intestine, the method comprising the steps of:
providing a non-human germ-free animal with a physiologically active substance derived from a bacterium capable of inducing Th1 cell proliferation or activation in an intestine;
detecting the number or activity of Th1 cells in an intestine of the non-human germ-free animal; and
determining that the physiologically active substance is a physiologically active substance capable of inducing Th1 cell proliferation or activation in an intestine, if Th1 cell proliferation or activation is detected in the previous step.

<24> A screening method for a bacterium capable of inducing Th1 cell proliferation or activation in an intestine, the method comprising the steps of:
adding a test bacterium to an intestinal epithelial cell in a system containing the intestinal epithelial cell and a peripheral blood mononuclear cell;
detecting the number or activity of Th1 cells in the system; and
determining that the test bacterium is a bacterium capable of inducing Th1 cell proliferation or activation in an intestine, if Th1 cell proliferation or activation is detected in the previous step.

<25> A screening method for a physiologically active substance capable of inducing Th1 cell proliferation or activation in an intestine, the method comprising the steps of:
adding a physiologically active substance derived from a bacterium capable of inducing Th1 cell proliferation or activation in an intestine to an intestinal epithelial cell in a system containing the intestinal epithelial cell and a peripheral blood mononuclear cell;
detecting the number or activity of Th1 cells in the system; and
determining that the physiologically active substance is a physiologically active substance capable of inducing Th1 cell proliferation or activation in an intestine, if Th1 cell proliferation or activation is detected in the previous step.

<26> A screening method for a substance capable of inducing Th1 cell proliferation or activation in an intestine, the method comprising the steps of:
adding a test substance and a bacterium capable of inducing Th1 cell proliferation or activation in an intestine to an intestinal epithelial cell in a system containing the intestinal epithelial cell and a peripheral blood mononuclear cell;
detecting the number or activity of Th1 cells in the system; and
determining that the test compound is a substance capable of inducing Th1 cell proliferation or activation in an intestine, if the number or activity of the Th1 cells detected in the previous step is more than that in a case without the test substance added.

<27> A screening method for a substance capable of inducing Th1 cell proliferation or activation in an intestine, the method comprising the steps of:
providing the non-human animal according to <17> with a test substance;
detecting the number or activity of Th1 cells in an intestine of the non-human animal; and
determining that the test substance is a substance capable of inducing Th1 cell proliferation or activation in an intestine, if the number or activity of the Th1 cells detected in the previous step is more than that in a case without the test substance provided.

<28> A composition for activating immunity, the composition comprising, as an active ingredient, the bacterium, the physiologically active substance, or the substance obtained by the screening method according to any one of <22> to <27>.

<29> The composition according to <28>, further characterized in that the composition is for inducing Th1 cell proliferation or activation.

<30> A vaccine composition comprising, as an active ingredient, the bacterium obtained by the screening method according to <22> or <24> or an antigen specific to the bacterium.

<31> A screening method for a substance having an activity of inducing or worsening a disease attributable to Th1 cells, the method comprising the steps of:
providing the non-human animal according to <18> with a test substance;
detecting a degree of a lesion of the disease attributable to Th1 cells in the non-human animal; and
determining that the test substance is a substance having an activity of inducing or worsening a disease attributable to Th1 cells, if the degree of the lesion detected in the previous step is more than that in a case without the test substance provided.

<32> A composition for inducing or worsening a disease attributable to Th1 cells, the composition comprising, as an active ingredient, the substance obtained by the screening method according to <31>.

<33> A screening method for a bacterium capable of suppressing Th1 cell proliferation or activation in an intestine, the method comprising the steps of:
providing a non-human germ-free animal with a test sample;
detecting the number or activity of Th1 cells in an intestine of the non-human germ-free animal; and
isolating a bacterium from a sample in the intestine of the non-human germ-free animal from which suppression of Th1 cell proliferation or activation is detected in the previous step.

<34> A screening method for a physiologically active substance capable of suppressing Th1 cell proliferation or activation in an intestine, the method comprising the steps of:
providing a non-human germ-free animal with physiologically active substance derived from a bacterium capable of suppressing Th1 cell proliferation or activation in an intestine;
detecting the number or activity of Th1 cells in an intestine of the non-human germ-free animal; and
determining that the physiologically active substance is a physiologically active substance capable of suppressing Th1 cell proliferation or activation in an intestine, if suppression of Th1 cell proliferation or activation is detected in the previous step.

<35> A screening method for a bacterium capable of suppressing Th1 cell proliferation or activation in an intestine, the method comprising the steps of:

adding a test bacterium to an intestinal epithelial cell in a system containing the intestinal epithelial cell and a peripheral blood mononuclear cell;

detecting the number or activity of Th1 cells in the system; and determining that the test bacterium is a bacterium capable of suppressing Th1 cell proliferation or activation in an intestine, if suppression of Th1 cell proliferation or activation is detected in the previous step.

<36> A screening method for a physiologically active substance capable of suppressing Th1 cell proliferation or activation in an intestine, the method comprising the steps of:

adding a physiologically active substance derived from a bacterium capable of suppressing Th1 cell proliferation or activation in an intestine to an intestinal epithelial cell in a system containing the intestinal epithelial cell and a peripheral blood mononuclear cell;

detecting the number or activity of Th1 cells in the system; and determining that the physiologically active substance is a physiologically active substance capable of suppressing Th1 cell proliferation or activation in an intestine, if suppression of Th1 cell proliferation or activation is detected in the previous step.

<37> A screening method for a substance capable of suppressing Th1 cell proliferation or activation in an intestine, the method comprising the steps of:

adding a test substance and a bacterium capable of inducing Th1 cell proliferation or activation in an intestine to an intestinal epithelial cell in a system containing the intestinal epithelial cell and a peripheral blood mononuclear cell;

detecting the number or activity of Th1 cells in the system; and determining that the test substance is a substance capable of suppressing Th1 cell proliferation or activation in an intestine, if the number or activity of the Th1 cells detected in the previous step is less than that in a case without the test compound added.

<38> A screening method for a substance capable of suppressing Th1 cell proliferation or activation in an intestine, the method comprising the steps of:

providing the non-human animal according to <17> with a test substance;

detecting the number or activity of Th1 cells in an intestine of the non-human animal; and determining that the test substance is a substance capable of suppressing Th1 cell proliferation or activation in an intestine, if the number or activity of the Th1 cells detected in the previous step is less than that in a case without the test substance provided.

<39> A composition for suppressing immunity, the composition comprising, as an active ingredient, the bacterium, the physiologically active substance, or the substance obtained by the screening method according to any one of <33> to <38>.

<40> The composition according to <39>, further characterized in that the composition is for suppressing Th1 cell proliferation or activation.

<41> The composition according to <39> or <40>, further characterized in that the composition is for treating, alleviating, or preventing a disease attributable to Th1 cells.

<42> A screening method for a substance having an activity of treating, alleviating, or preventing a disease attributable to Th1 cells, the method comprising the steps of:

providing the non-human animal according to <18> with a test substance;

detecting a degree of a lesion of the disease attributable to Th1 cells in the non-human animal; and determining that the test substance is a substance having an activity of treating, alleviating, or preventing a disease attributable to Th1 cells, if the degree of the lesion detected in the previous step is less than that in a case without the test substance provided.

<43> A composition for treating, alleviating, or preventing a disease attributable to Th1 cells, the composition comprising, as an active ingredient, the substance obtained by the screening method according to <42>.

<44> A composition for testing a disease attributable to Th1 cells, the composition comprising an antibody capable of specifically recognizing the bacterium according to any one of <1> to <4>.

<45> A composition for testing a disease attributable to Th1 cells, the composition comprising a polynucleotide for detecting a nucleotide sequence specific to the bacterium according to any one of <1> to <4>.

<46> A physiologically active substance derived from the bacterium according to any one of <1> to <4>.

<47> An antigen specific to the bacterium according to any one of <1> to <4>.

<48> An antibody capable of specifically recognizing the bacterium according to any one of <1> to <4>.

<49> A polynucleotide for detecting a nucleotide sequence specific to the bacterium according to any one of <1> to <4>.

Advantageous Effects of Invention

According to the present invention, targeting bacteria capable of inducing Th1 cell proliferation or activation in an intestine (Th1 cell-inducible bacteria) such as the 2H7 strain, the 11E12 strain, the 34E1 strain, the BAA-1705 strain, the 700603 strain, and the 40B3 strain belonging to *Klebsiella* to, for example, suppress the bacterial growth or kill the bacteria makes it possible to suppress Th1 cell proliferation or activation. Moreover, the suppression of the growth of the Th1 cell-inducible bacteria or the like makes it also possible to suppress immunity in an intestine, and consequently makes it also possible to treat, alleviate, or prevent a disease such as Crohn's disease and ulcerative colitis attributable to Th1 cells.

Further, according to the present invention, detecting the oral bacteria makes it also possible to test a disease attributable to Th1 cells.

In addition, according to the present invention, the use of such a Th1 cell-inducible bacterium or a physiologically active substance thereof makes it also possible to induce Th1 cell proliferation or activation, activate immunity, and consequently treat an infectious disease and enhance an anticancer action.

Furthermore, the present invention makes it also possible to screen for a bacterium and so forth capable of suppressing or inducing Th1 cell proliferation or activation in an intestine.

BRIEF DESCRIPTION OF DRAWINGS

FIG. 42 is a photograph for illustrating the result of analyzing the motile characteristics of Ka-11E12 and the like.

Biological Material Deposit Information

Figure 1:
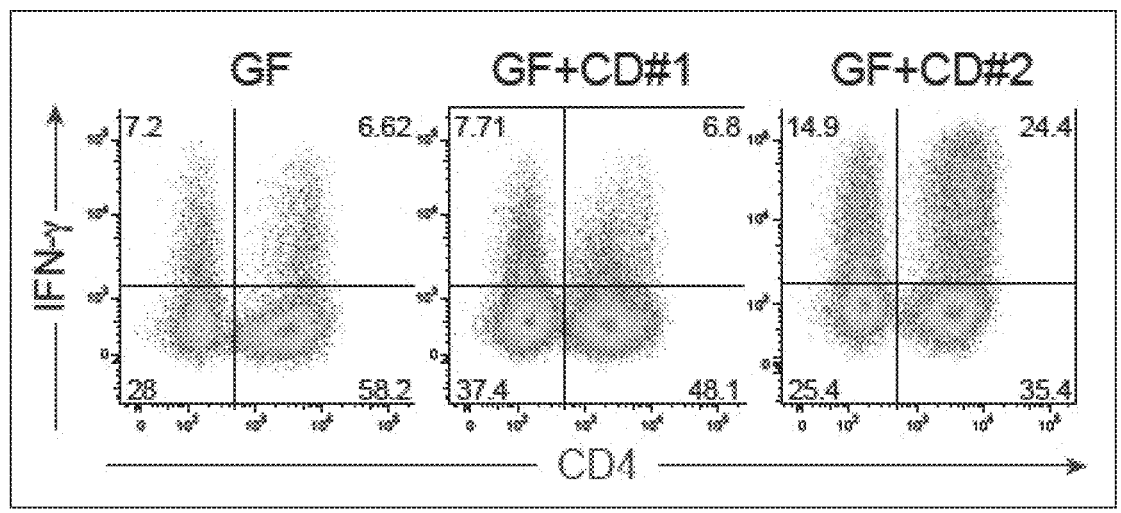
FIG. 1 shows plots for illustrating representative results of flow cytometry analysis of the frequencies of IFN-γ positive cells among CD4⁺TCRβ⁺ T cells in the colonic lamina propria (LP) of exGF B6 mice inoculated with saliva samples from two Crohn's disease patients (CD #1, CD #2), respectively. Note that, in a plot, "GF" indicates data on a group inoculated with no saliva sample.

Applicants made the following biological deposits under the terms of the Budapest Treaty on the International Recognition of the Deposit of Microorganisms for the Purposes of Patent Procedure at NITE Patent Microorganisms Depositary, National Institute of Technology and Evalution, #122, 2-5-8 Kazusakamatari, Kisarazu-shi, Chiba 292-0818, Japan:

| Depositor Identification Reference | International Depository Designation | Date of Deposit |
|---|---|---|
| *Klebsiella pneumonia* Kp-2H7 strain | NITE BP-04150 | Sep. 3, 2024 |
| *Klebsiella aeromobilis* Ka-11E12 strain | NITE BP-04151 | Sep. 3, 2024 |

DESCRIPTION OF EMBODIMENTS

<Bacterium Capable of Inducing Th1 Cells in Intestine>

As described above, the present inventors have revealed that when a 2H7 strain, an 11E12 strain, a 34E1 strain, a BAA-1705 strain, a 700603 strain, or a 40B3 strain belonging to *Klebsiella* colonizes in an intestine, Th1 cells are markedly induced. Thus, the present invention provides a bacterium capable of inducing Th1 cell proliferation or activation in an intestine.

Note that the 2H7 strain, the 11E12 strain, the 34E1 strain, and the 40B3 strain are bacteria normally present in the human oral cavity (oral bacteria). Meanwhile, the BAA-1705 strain and the 700603 strain are also bacteria normally present in the human oral cavity, but the bacteria are detected in human urine (bacteria in urine).

In the present invention, the term "Th1 cell" means a subtype of CD4 positive helper T cells (Th cells), and the cell enhances cell-mediated immunity. Moreover, the "activity of Th1 cells" and related terms mean to include: production of Th1 cytokines (such as IFN-γ) by the cells; activation of cells such as macrophages and cytotoxic T cells (CTL) with the cytokines; and enhancement of cell-mediated immunity through the activation. Further, "inducing Th1 cell proliferation or activation" and similar phrases mean to include differentiation induction from naive T cells to Th1 cells, leading to Th1 cell proliferation or activation. Additionally, the action of inducing Th1 cell proliferation or activation in an intestine can be evaluated by quantitatively detecting a marker (for example, CD4 and IFN-γ) specific to Th1 cells. Such quantitative detection can be conducted by known methods, for example, detection methods using an antibody (immunological methods) such as flow cytometry, imaging cytometry, ELISA methods, radioimmunoassay, immunohistochemical staining, immunoprecipitation, immunoblotting, and antibody array analyses. Moreover, whether certain bacterium, substance, or the like has an action of inducing Th1 cell proliferation or activation in an intestine or not can be determined, for example, by employing screening methods to be described later. More concretely, if the percentage of IFN-γ$^+$ cells detected in an intestine by flow cytometry is normally 10% or more among CD4$^+$TCRβ$^+$ T cells, it can be determined that the bacterium, substance, or the like has an action of inducing Th1 cell proliferation or activation in an intestine. It is preferable to determine that the bacterium, substance, or the like has an action of inducing Th1 cell proliferation or activation in an intestine if the percentage is 25% or more. It is more preferably to determine that the bacterium, substance, or the like has an action of inducing Th1 cell proliferation or activation in an intestine if the percentage is 30% or more.

The "bacterium capable of inducing Th1 cell proliferation or activation in an intestine" of the present invention is a bacterium normally present in the human oral cavity and capable of inducing Th1 cell proliferation or activation upon intestinal colonization.

The "bacterium capable of inducing Th1 cell proliferation or activation in an intestine" of the present invention is a bacterium belonging to preferably *Klebsiella*, more preferably *Klebsiella pneumoniae* or *Klebsiella aeromobilis*, and being capable of inducing Th1 cell proliferation or activation in an intestine.

Moreover, the "bacterium capable of inducing Th1 cell proliferation or activation in an intestine" of the present invention is preferably a bacterium easily colonizing in an intestinal environment where the diversity changes by antibacterial drug administration in comparison with a healthy state.

Further, the "bacterium capable of inducing Th1 cell proliferation or activation in an intestine" of the present invention is a bacterium easily colonizing in an intestinal environment where the diversity changes by colitis in comparison with a healthy state.

Furthermore, as shown in FIGS. 53-62, the present inventors have found out 64 genes whose functions have been already known and related to the induction of Th1 cell proliferation or activation induction.

Thus, the "bacterium capable of inducing Th1 cell proliferation or activation in an intestine" of the present invention preferably comprises genes encoding at least five proteins selected from the following protein group; more preferably, comprises genes encoding at least 10 proteins selected from the following protein group; further preferably comprises genes encoding at least 20 proteins selected from the following protein group; furthermore preferably, comprises genes encoding at least 30 proteins selected from the following protein group; and still furthermore preferably, comprises genes encoding at least 50 proteins selected from the following protein group.

Group of proteins:
Mannose-1-phosphate guanylyltransferase 1,
Multiphosphoryl transfer protein,
PTS system fructose-specific EIIABC component,
Phosphomannomutase/phosphoglucomutase,
Mannosylfructose-phosphate synthase,
3-oxoacyl-[acyl-carrier-protein] reductase FabG,
rhamnosyl/mannosyltransferase,
Galactitol-1-phosphate 5-dehydrogenase,
Galactitol permease IIC component,
Galactitol-specific phosphotransferase enzyme IIB component,
D-tagatose-1,6-bisphosphate aldolase subunit GatZ,
Tagatose-6-phosphate kinase,
D-tagatose-1,6-bisphosphate aldolase subunit GatY,
Galactitol permease IIC component,
GDP-mannose-dependent alpha-(1-2)-phosphatidylinositol mannosyltransferase,
L-xylulose/3-keto-L-gulonate kinase,
2-dehydro-3-deoxygluconokinase,
Capsular glucan synthase,
3-octaprenyl-4-hydroxybenzoate carboxy-lyase partner protein,
2-octaprenylphenol hydroxylase,
Phenolic acid decarboxylase subunit C,
Oxaloacetate decarboxylase beta chain,
Aconitate hydratase 2, Putative aldolase LsrF,
Putative acetyltransferase,
Propanediol utilization protein PduA,
Putative glycosyltransferase EpsF,
Hemin-binding periplasmic protein HmuT precursor,
Teichoic acids export ATP-binding protein TagH,
Teichoic acid translocation permease protein TagG,
Outer membrane protein TolC precursor,
Multidrug transporter EmrE,
Magnesium and cobalt efflux protein CorC,
Inner membrane protein YibH,
Aspartate/alanine antiporter,
Ferric enterobactin receptor precursor,
Signal transduction histidine-protein kinase BarA,
Hemolysin transporter protein ShlB precursor,
Oligopeptide transport ATP-binding protein OppD,
Arsenical pump-driving ATPase,
Putative anti-sigma factor antagonist,
Putative membrane protein YdfK,
Putative hemoglobin and hemoglobin-haptoglobin-binding protein 2 precursor,
(2R)-3-sulfolactate dehydrogenase (NADP(+)),
Peptidase E,
Oligopeptidase A,
Phosphinothricin N-acetyltransferase,
Putative 2-hydroxyacid dehydrogenase YoaD,
mRNA interferase RelE,
Single-stranded-DNA-specific exonuclease RecJ,
Tyrosine recombinase XerD_6,
Tyrosine recombinase XerD,
Glucitol operon repressor,
Formate hydrogenlyase transcriptional activator,
HTH-type transcriptional regulator TdfR,
HTH-type transcriptional regulator CatM,
Transcriptional regulatory protein tctD,
HTH-type transcriptional repressor AseR,
Cyclic di-GMP phosphodiesterase YahA, Serine-protein kinase RsbW,
Filamentous hemagglutinin,
Dihydropteroate synthase,
Delta-aminolevulinic acid dehydratase, and
Aerobic respiration control protein ArcA.

Meanwhile, although these proteins are specified by particular amino acid sequences (amino acid sequences specified under KEGG or UniProt ID) in FIGS. 53-62, the proteins according to the present invention include not only the proteins specified by these typical amino acid sequences, but also functionally active derivatives thereof, functionally active fragments thereof, homologs thereof, and mutants encoded by nucleic acids capable of hybridizing to nucleic acids encoding the proteins under high stringency conditions or low stringency conditions. In addition, such derivatives, fragments, homologs, or mutants include proteins having a homology of at least 60% (preferably 70%, more preferably 80%, further preferably 90%, furthermore preferably 95%, particularly preferably 99%) with the particular amino acid sequences.

Figures 54, 55:
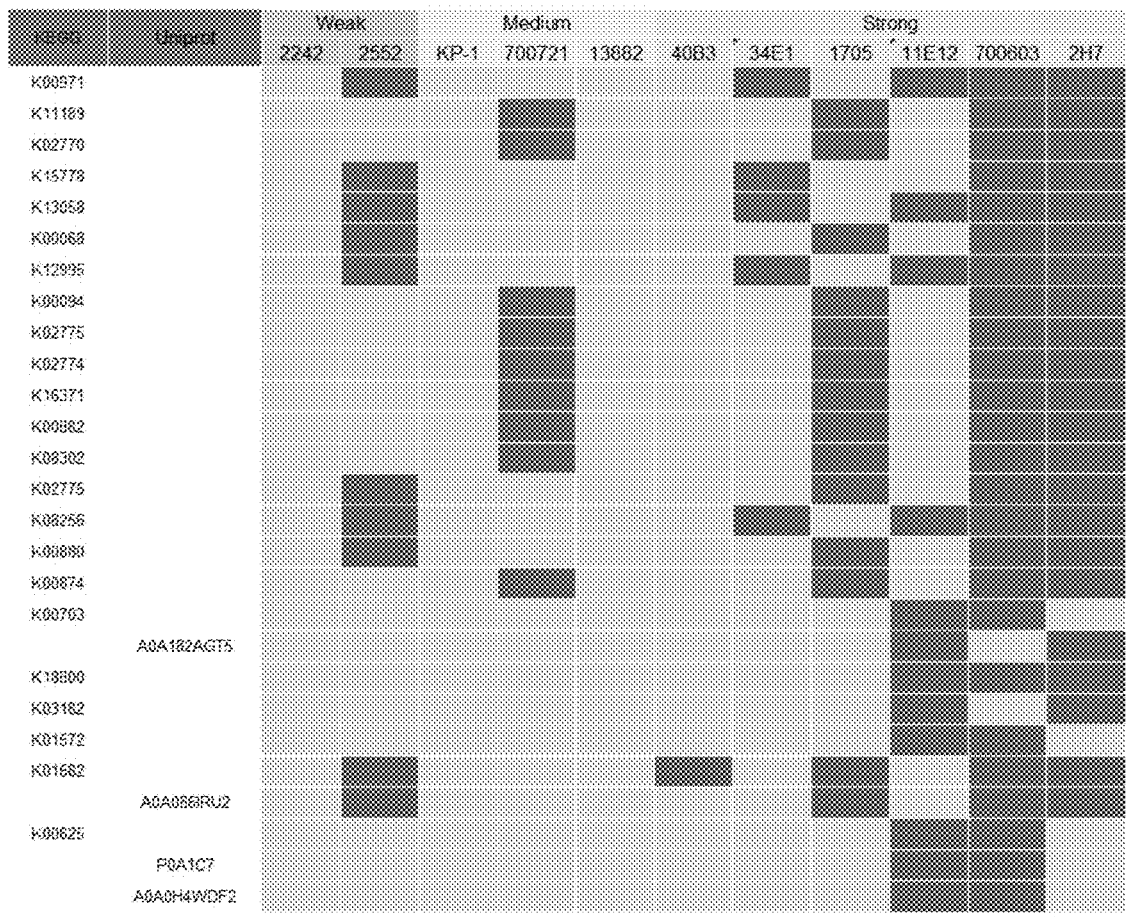

Moreover, as shown in FIGS. 53 and 54, the proteins according to the present invention include proteins involved in a metabolism of mannose, fructose, or galactose. Thus, the "bacterium capable of inducing Th1 cell proliferation or activation in an intestine" of the present invention preferably expresses a gene involved in a metabolism of mannose, fructose, or galactose.

Further, the "bacterium capable of inducing Th1 cell proliferation or activation in an intestine" of the present invention is preferably a bacterium which belongs to Klebsiella, forms no capsule, and induces Th1 cell proliferation or activation in an intestine; more preferably, a bacterium which belongs to Klebsiella pneumoniae, forms no capsule, produces outer membrane vesicles (OMV) or OMV-like structures, and induces Th1 cell proliferation or activation in an intestine.

Furthermore, the "bacterium capable of inducing Th1 cell proliferation or activation in an intestine" of the present invention is preferably a bacterium which belongs to Klebsiella and has a flagellum, or preferably a bacterium which belongs to Klebsiella and has a stimulatory action on TLR5.

In addition, examples of the "bacterium capable of inducing Th1 cell proliferation or activation in an intestine" of the present invention typically include the 2H7 strain, the 11E12 strain, the 34E1 strain, the BAA-1705 strain, the 700603 strain, and the 40B3 strain belonging to Klebsiella. Note that, regarding details of these bacteria, see Table 11.

Table 11

| Bacterial Name | Supplier | Information from Supplier | Registry number |
| --- | --- | --- | --- |
| KCTC2242 | KCTC | http://kctc.kribb.re.kr/English/-Search View.aspx?sn=2242 | NCBI Taxonomy ID: 1049565 |
| 2552 | ATCC | https://www.atcc.org/Products/All/BAA-2552.aspx | NCBI Taxonomy ID: 507522 |
| KP-1 | — | — | NCBI Taxonomy ID: 1365186 |
| 700721 | ATCC | https://www.atcc.org/Products/All/700721.aspx | NCBI Taxonomy ID: 272620 |
| 13882 | JCM | https://www.atcc.org/Products/All/13882.aspx | NCBI Taxonomy ID: 1913574 |
| 40B3 | — | — | SAMD00083913 |
| 34E1 | — | — | SAMD00083911 |
| 1705 | ATCC | https://www.atcc.org/Products/All/BAA-1705.aspx | NCBI Taxonomy ID: 1276652 |
| 11E12 | — | — | SAMD00083912 |
| 700603 | ATCC | https://www.atcc.org/Products/All/700603.aspx | NCBI Taxonomy ID: 1276653 |
| 2H7 | — | — | SAMD00083910 |

The bacteria belonging to Klebsiella, the bacteria belonging to Klebsiella aeromobilis, the bacteria belonging to Klebsiella pneumoniae, the 2H7 strain, the 11E12 strain, the 34E1 strain, the BAA-1705 strain, the 700603 strain, and the 40B3 strain can be identified, for example, by determining the nucleotide sequence encoding 16S rRNA. In addition, as will be explained in the test method to be described later, these bacteria can also be identified based on a nucleotide sequence specific thereto, and so forth. Note that the nucleotide sequence specific to the 2H7 strain or the 11E12 strain is not particularly limited. Nevertheless, preferable examples of the nucleotide sequence include nucleotide sequences which the 2H7 strain or the 11E12 strain has, but which are not found in a BAA-2552 strain and a 700721 strain belonging to the same *Klebsiella* as those strains (more preferably, nucleotide sequences not found in the BAA-2552 strain, a KCTC2242 strain, KP-1, the 700721 strain, and a 13882 strain).

Moreover, the examples of the "bacterium capable of inducing Th1 cell proliferation or activation in an intestine" of the present invention include bacteria comprising a DNA containing a nucleotide sequence having a homology or an identity of 70% or more (preferably 80% or more, more preferably 85% or more, further preferably 90% or more, furthermore preferably 95% or more (96% or more, 97% or more, 98% or more, 99% or more) with the nucleotide sequence encoding 16S rRNA of the 2H7 strain, the 11E12 strain, the 34E1 strain, the BAA-1705 strain, the 700603 strain, or the 40B3 strain. The examples further includes bacteria comprising a DNA containing a nucleotide sequence having a homology or an identity of 70% or more (preferably 80% or more, more preferably 85% or more, further preferably 90% or more, furthermore preferably 95% or more (96% or more, 97% or more, 98% or more, 99% or more) with the nucleotide sequence specific to the 2H7 strain, the 11E12 strain, the 34E1 strain, the BAA-1705 strain, the 700603 strain, or the 40B3 strain.

<Composition Etc. For Inducing Th1 Cell Proliferation or Activation>

When colonizing in an intestine, the above-described Th1 cell-inducible bacterium is capable of inducing Th1 cell proliferation or activation. Thus, the present invention can provide a composition or method for inducing Th1 cell proliferation or activation.

Moreover, since Crohn's disease and ulcerative colitis are diseases based on the promotion of an immune response (autoimmune disease), the above-described Th1 cell-inducible bacterium, which may serve as the causative factor, has an immunity activating action. Furthermore, Th1 cells are CD4 positive helper T cells producing IFN-γ, play an important role in defending the infection with pathogens such as *Mycobacterium tuberculosis* and *Listeria*, and also have important actions in monitoring and excluding cancerous cells. Recently, it has also been revealed that the presence of bacteria such as *Bacteroides* and *Bifidobacterium* in an intestine and the induction of Th1 cells by the bacteria influence the anti-tumor effect of immune checkpoint inhibitors (such as anti-CTLA-4 antibody, anti-PD-L1 antibody), which serve as one of immunotherapies against cancers. Thus, the present invention can provide a composition or method for activating immunity.

Note that the "immunity" to be activated or suppressed in the present invention includes not only mucosal immunity (such as intestinal immunity) but also general immunity. Moreover, the "immunity" includes not only cell-mediated immunity but also humoral immunity.

The "bacterium capable of inducing Th1 cell proliferation or activation in an intestine" incorporated as the active ingredient in the composition of the present invention is as described above, and may be living cells or dead cells. Moreover, depending on the usage of the incorporated active ingredient, the bacterium may be modified (for example, genetically modified). Such a modification is not particularly limited. In a case where the composition of the present invention is a vaccine adjuvant to be described later, the modification includes the enhancement of the action of inducing Th1 cell proliferation or activation in an intestine.

Meanwhile, the composition of the present invention should comprise a single strain of the bacterium capable of inducing Th1 cell proliferation or activation in an intestine, but may comprise multiple strains thereof. Alternatively, the composition can be used in combination. As a result of the combinational use, when the composition is provided or absorbed (when the composition is used in combination), the multiple bacterial strains may exist in two or more compositions (for example, the multiple bacterial strains can also exist in separate compositions, respectively).

In the present invention, a "physiologically active substance derived from the bacterium capable of inducing Th1 cell proliferation or activation in an intestine" means to include substances incorporated in the bacterium capable of inducing Th1 cell proliferation or activation in an intestine, secretions from the bacterium, and metabolites by the bacterium. More concretely, the physiologically active substance includes polypeptide fractions, polynucleotide fractions, carbohydrate fractions, lipid fractions, and low-molecular weight metabolite fractions of the bacterium or the culture supernatant. The physiologically active substance further includes outer membrane vesicles (OMV) or OMV-like structures produced by the bacterium capable of inducing Th1 cell proliferation or activation in an intestine. The physiologically active substance according to the present invention is preferably a substance capable of inducing Th1 cell proliferation or activation in an intestine; more preferably, a substance which is recognized by a Toll-like receptor (TLR) involving MyD88/Trif, and which functions as a ligand thereof. In addition, such a physiologically active substance can be identified by purifying an active component from the bacterium, the culture supernatant, a sample (such as feces) in an intestine of a mouse colonized with the bacterium, a sample (such as saliva) in a human oral cavity, a sample in a human urinary bladder, a sample in a human vagina and a sample (such as urine) in a human ureter, a sample in a human intestine, or the like, for example, by a screening method to be described later.

The composition of the present invention may be in the form of a pharmaceutical composition, a food or drink (including an animal feed), or a reagent used for a research purpose (for example, in vitro or in vivo experiment).

As described above, the Th1 cell-inducible bacterium or the physiologically active substance derived from the bacterium, which serve as the active ingredient of the composition of the present invention, induces Th1 cell proliferation or activation in an intestine or activates immunity. Accordingly, the Th1 cell-inducible bacterium or the physiologically active substance is suitably used as: a pharmaceutical composition, food, or drink for treating, preventing, or alleviating an infectious disease such as tuberculosis; a pharmaceutical composition, food, or drink for enhancing the anti-cancer action when used in combination with an anticancer agent or an immune checkpoint inhibitor; further, a pharmaceutical composition (vaccine adjuvant) for enhancing the immune response action when used in combination with a vaccine. Note that, in the present invention, "treat" and related terms include adjuvant therapy.

The composition of the present invention can be formulated by known formulation methods. The composition of the present invention can be used for administration orally, parenterally (for example, intestinally, intramuscularly, intravenously, intratracheally, intranasally, transdermally, intradermally, subcutaneously, intraocularly, intravaginally, intraperitoneally, rectally, or by inhalation), or through multiple routes consisting of a combination of these, in the form of, for example, a capsule, a tablet, a pill, a liquid, a powder, a granule, a fine granule, a film coating agent, a pellet, a troche, a sublingual tablet, masticatory, a buccal, a paste, a syrup, a suspension, an elixir, an emulsion, an endermic liniment, an ointment, a plaster, a poultice, a percutaneous absorption preparation, a lotion, an inhalation, an aerosol, an injection, a suppository, or the like.

When formulated, these can be combined as appropriate with a pharmacologically acceptable carrier or a carrier acceptable as a food or drink: concretely, sterile water or a saline, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a disintegrant, a buffer, a coating agent, a lubricant, a colorant, a sweetener, a viscous agent, a corrigent, a solubilizer, or other additives.

Meanwhile, in these formulations, from the viewpoints such as more efficiently inducing Th1 cell proliferation or activation in an intestine, particularly in formulating a pharmaceutical preparation for oral administration, the composition of the present invention may be combined with a composition which enables an efficient delivery to an intestine. Such a composition enabling the delivery to an intestine is not particularly limited, and known compositions can be employed as appropriate. Examples thereof include pH sensitive compositions, compositions for suppressing the release into the intestinal tract (such as cellulose-based polymers, acrylic acid polymers and copolymers, vinyl acid polymers and copolymers), bioadhesive compositions which specifically adhere to mucosas of the intestinal tract (for example, a polymer described in the specification of U.S. Pat. No. 6,368,586), protease inhibitor-containing compositions, and compositions specifically degraded by enzymes in the intestine).

In addition, in the case where the composition for inducing Th1 cell proliferation or activation of the present invention is used as a pharmaceutical composition, the composition may further comprise a known substance (such as an antiviral agent, an antibacterial agent, an anticancer agent, an immune checkpoint inhibitor) used for treating, preventing, or alleviating an infectious disease or a cancer, or may be used in combination with such a substance. In the case where the composition is used as a vaccine adjuvant, the composition of the present invention may comprise another known vaccine adjuvant or immunostimulant, in addition to an antigen (for example, a bacterium- or virus-specific antigen, a cancer-specific antigen), which serves as the active ingredient of the vaccine, or may be used in combination with these substances.

In the case where the composition of the present invention is used as a food or drink, the food or drink may be, for example, a health food, a functional food, a food for specified health use, a food with nutrient function claims, a function-labeled food, a nutritional supplementary food, a medical food for the ill, or an animal feed. Concrete examples of the food or drink include liquid foods such as fermented drinks, oil-containing products, soups, dairy drinks, refreshing drinks, tea drinks, alcoholic drinks, energy drinks, and jelly drinks; carbohydrate-containing foods; livestock-processed foods; processed seafoods; vegetable-processed foods; semi-solid foods; fermented foods; confectionaries; retort pouch foods; microwave foods; and the like. The examples further include health foods or drinks prepared in the form of powder, granule, tablet, capsule, liquid, paste, or jelly. Note that, in the present invention, the food or drink can be produced by production techniques known in this technical field. To the food or drink, an active ingredient (for example, a nutrient or the like) for alleviating or preventing an infectious disease or a cancer may be added. Moreover, in combination with another ingredient or another functional food which exhibit a function other than the alleviation or the like, multi-functional food or drink can be prepared.

A product (drug, food, drink, vaccine, reagent) of the composition of the present invention or a manual thereof may be provided with an indication stating that the product is used for inducing Th1 cell proliferation or activation or for treating, alleviating, or preventing a disease such as an infectious disease or a cancer. Meanwhile, in the case of the food or drink, the product of the composition or the like of the present invention may be provided with an indication of the health function as a health functional food (a food for specified health use, a food with nutrient function claims, a function-labeled food) to be distinguished from general foods by the appearance, target persons, and so forth. Herein, "a product or a manual provided with an indication" means that the indication is attached to the main body, container, package, or the like of the product, or that the indication is provided in the manual, package insert, advertisement, other printed materials, or the like disclosing information on the product.

Further, the composition of the present invention may be in the form of a kit. The kit includes, for example, an embodiment wherein a bacterium capable of inducing Th1 cell proliferation or activation or a physiologically active substance derived from the bacterium, an antiviral agent, an antibacterial agent, an anticancer agent, an immune checkpoint inhibitor, an antigen, another vaccine adjuvant, and the like are normally present as two or more substances (compositions or the like), and optionally these may be, for example, mixed to prepare a single composition before provided to a subject.

Additionally, the present invention also provides: a method for inducing Th1 cell proliferation or activation in a subject or a method for activating immunity in the subject, the methods characterized in that the subject is provided with a composition for inducing Th1 cell proliferation or activation, or a Th1 cell-inducible bacterium or a physiologically active substance derived from the bacterium, which serve as the active ingredient of the composition.

The composition or the active ingredient of the present invention can be used for animals including human as the subject. The animals other than human are not particularly limited, and various domestic animals, poultry, pet animals, experimental animals, and the like can be the subject. Concretely, the animals include pigs, cattle, horses, sheep, goats, chickens, ducks, ostriches, domesticated ducks, dogs, cats, rabbits, hamsters, mice, rats, monkeys, and the like, but are not limited thereto.

Moreover, the subject to be provided with the composition for inducing Th1 cell proliferation or activation or the active ingredient of the present invention includes animals infected with a virus, a bacterium, or the like, regardless of the disease development. In addition, from the viewpoint of the prevention, animals which are not infected or may be infected with a virus, a bacterium, or the like may be provided with the composition or the like of the present invention. Further, from the viewpoint of preventing the relapse, the composition or the like of the present invention can also be suitably used for animals carrying a virus, a bacterium, or the like without the symptom. In addition, similarly, the composition or the like of the present invention can also be suitably used for not only animals having a cancer, but also animals which may have a cancer and animals after anti-cancer therapy.

The method for providing the composition or the like of the present invention is not particularly limited. The composition may be orally administered, or may be parenterally administered (for example, administered into an intestine). In the case of oral administration, from the viewpoint of further enhancing the effects of the composition or the like of the present invention, the subject to be provided with the composition or the like of the present invention is preferably provided with a proton-pump inhibitor (PPI) or the like in advance to reduce the production of gastric acid, or provided with an antibiotic (for example, ampicillin, tylosin) in advance.

Moreover, when the composition or the like of the present invention is provided, the amount provided can be selected as appropriate by those skilled in the art, depending on the age, body weight, disease symptom, and health state of the subject, the type of the composition (such as drug, food, drink), the providing method, and so forth.

<Vaccine Composition Etc.>

The above-described Th1 cell-inducible bacterium colonizes in an intestine and induces the Th1 cell proliferation or activation, thereby inducing a disease such as Crohn's disease and ulcerative colitis attributable to Th1 cells. Hence, inducing an immune response by targeting the Th1 cell-inducible bacterium and then removing the bacterium from the intestine make it possible to treat, alleviate, or prevent the disease. Thus, the present invention can provide a vaccine composition or method for inducing an immune response to the bacterium to treat, alleviate, or prevent a disease attributable to Th1 cells.

In the present invention, the term "disease attributable to Th1 cells" means a disease induced by the Th1 cell proliferation or activation. Examples of the disease include inflammatory bowel diseases (chronic inflammatory bowel diseases such as Crohn's disease, ulcerative colitis, and inflammatory bowel diseases, and the like), diabetes mellitus type 1, autoimmune diseases such as rheumatoid arthritis, experimental autoimmune encephalomyelitis (EAE), multiple sclerosis, and systemic lupus erythematosus, and chronic inflammatory diseases.

The "bacterium capable of inducing Th1 cell proliferation or activation in an intestine" incorporated as the active ingredient in the composition of the present invention is as described above, and may be living cells or dead cells. Moreover, depending on the usage of the incorporated active ingredient, the bacterium may be modified (for example, genetically modified). Such a modification is not particularly limited. In the case where the composition of the present invention is a vaccine composition, the modification includes the suppression of the action of inducing Th1 cell proliferation or activation in an intestine, thereby preventing the induction of inflammation or the like. Meanwhile, the composition of the present invention should comprise a single strain of the bacterium capable of inducing Th1 cell proliferation or activation in an intestine, but may comprise multiple strains thereof. Alternatively, the composition can be used in combination. As a result of the combinational use, when the composition is provided or absorbed (when the composition is used in combination), the multiple bacterial strains may exist in two or more compositions.

In the present invention, an "antigen specific to the bacterium capable of inducing Th1 cell proliferation or activation in an intestine" means a substance (such as polypeptide, polynucleotide, carbohydrate, lipid) incorporated in the bacterium and also having an antigenicity or an immunogenicity. Herein, the term "immunogenicity" means the ability to activate a primary immune response or a memory immune response. The term "immune response" includes responses of CD4 positive T lymphocytes, CD8 positive T lymphocytes, and B lymphocytes. Such a response of T lymphocytes may be a proliferation type and/or a cytokine (for example, IL-2, IL-3, IL-4, IL-5, IL-6, IL-12, IL-13, IL-15, TNF-α, IFN-γ) production type. Alternatively, these responses may lead to the production of cytotoxic T lymphocytes (CTL). The B lymphocyte reaction may lead to the antibody production by the B lymphocytes thus reacting. Moreover, the term "antigenicity" means the ability to be recognized by an antibody molecule or an antigen-specific T-cell receptor (TCR) on an activated effector T cell (for example, cytokine-producing T cell, CTL, or the like). As described above, the "antigen specific to the bacterium capable of inducing Th1 cell proliferation or activation in an intestine" means to include: substances which are recognized by an antibody capable of specifically recognizing the bacterium or the like, and thus which is capable of binding to the antibody; or substances which, after processing by an appropriate antigen-presenting cell (APC) and binding to an appropriate major histocompatibility complex (MHC) molecule, are recognized by a TCR on an effector T cell induced by the reaction with the bacterium or the like, and thus which is capable of binding to the TCR.

Moreover, such a bacterium-specific antigen can be identified by those skilled in the art based on the reactivity with an antigen-specific antiserum and/or T lymphocytes according to known screening method (for example, Paul WE (editor), Fundamental Immunology, 1993, 3rd edition, pp. 243 to 247, Harlow and Lane, Antibodies, A Laboratory Manual, Cold Spring Harbor Laboratory, 1998). Further, the amino acid sequence of the bacterium-specific antigen (polypeptide) can be estimated by an analysis utilizing a computer program (for example, MHC-THREAD, EpiPredict, HLA-DR4 binding, ProPred, BIMAS, SVMHC, NetMHC, PREDICT, LpPep, SYFPEITHI, RankPep).

The vaccine composition of the present invention can be formulated by known formulation methods. The composition can be used for administration orally, parenterally (for example, intestinally, intramuscularly, intravenously, intratracheally, intranasally, transdermally, intradermally, subcutaneously, intraocularly, intravaginally, intraperitoneally, rectally or by inhalation), or through multiple routes consisting of a combination of these, in the form of, for example, an inhalation, an aerosol, an injection, a powder, a granule, a fine granule, a liquid, a capsule, a tablet, a pill, a film coating agent, a pellet, a troche, a sublingual tablet, a masticatory, a buccal, a paste, a syrup, a suspension, an elixir, an emulsion, an endermic liniment, an ointment, a plaster, a poultice, a percutaneous absorption preparation, a lotion, a suppository, or the like.

When formulated, these can be combined as appropriate with a pharmacologically acceptable carrier or a carrier acceptable as a food or drink: concretely, sterile water or a saline, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a disintegrant, a buffer, a coating agent, a lubricant, a colorant, a sweetener, a viscous agent, a corrigent, a solubilizer, or other additives.

Moreover, the vaccine composition of the present invention may comprise a known vaccine adjuvant or immunostimulant. Examples of the vaccine adjuvant include aluminum hydroxide, KLH, MPL, QS21, complete Freund's adjuvant, incomplete Freund's adjuvant, aluminum phosphate, BCG, alums, CpG DNA, other TLR agonists, and the like, or combinations thereof. Further, as necessary, an auxiliary agent such as an albumin, a wetting agent, and an emulsifier may be added in an embodiment. Moreover, examples of the immunostimulant include various cytokines (for example, IL-12, IL-18, GM-CSF, IFNγ, IFNα, IFNβ, IFNω, Flt3 ligand).

A product (drug, vaccine) of the composition of the present invention or a manual thereof may be provided with an indication stating that the product is used for inducing an immune response to a bacterium capable of inducing Th1 cell proliferation or activation in an intestine to treat, alleviate, or prevent a disease attributable to Th1 cells. Herein, "a product or a manual provided with an indication" means that the indication is attached to the main body, container, package, or the like of the product, or that the indication is provided in the manual, package insert, advertisement, other printed materials, or the like disclosing information on the product.

Moreover, the composition of the present invention may be in the form of a kit. The kit includes, for example, an embodiment wherein a bacterium capable of inducing Th1 cell proliferation or activation or an antigen specific to the bacterium, a vaccine adjuvant, an immunostimulant, and the like are normally present as two or more substances (compositions or the like), and optionally these may be, for example, mixed to prepare a single composition before provided to a subject.

Additionally, the present invention also provides: a method for inducing an immune response to a bacterium in a subject or a method for treating, alleviating, or preventing a disease attributable to Th1 cells in the subject, the methods characterized in that the subject is provided with a vaccine composition, or the bacterium or an antigen specific to the bacterium, which serve as the active ingredient of the composition.

The composition or the active ingredient of the present invention can be used for animals including human as the subject. The animals other than human are not particularly limited, and various domestic animals, poultry, pet animals, experimental animals, and the like can be the subject.

Moreover, the subject to be provided with the vaccine composition or the active ingredient of the present invention includes animals comprising the bacterium capable of inducing Th1 cell proliferation or activation in an intestine, regardless of the development of the disease attributable to Th1 cells. In addition, from the viewpoint of the prevention, animals which do not comprise or may comprise the bacterium may be provided with the composition or the like of the present invention.

The method for providing the composition or the like of the present invention is not particularly limited. The composition may be orally administered, or may be parenterally administered. Further, when the composition or the like of the present invention is provided, the amount provided can be selected as appropriate by those skilled in the art, depending on the age, body weight, disease symptom, and health state of the subject, the dosage form of the composition, the providing method, and so forth.

<Composition Etc. For Suppressing Th1 Cell Proliferation or Activation>

Figure 51:
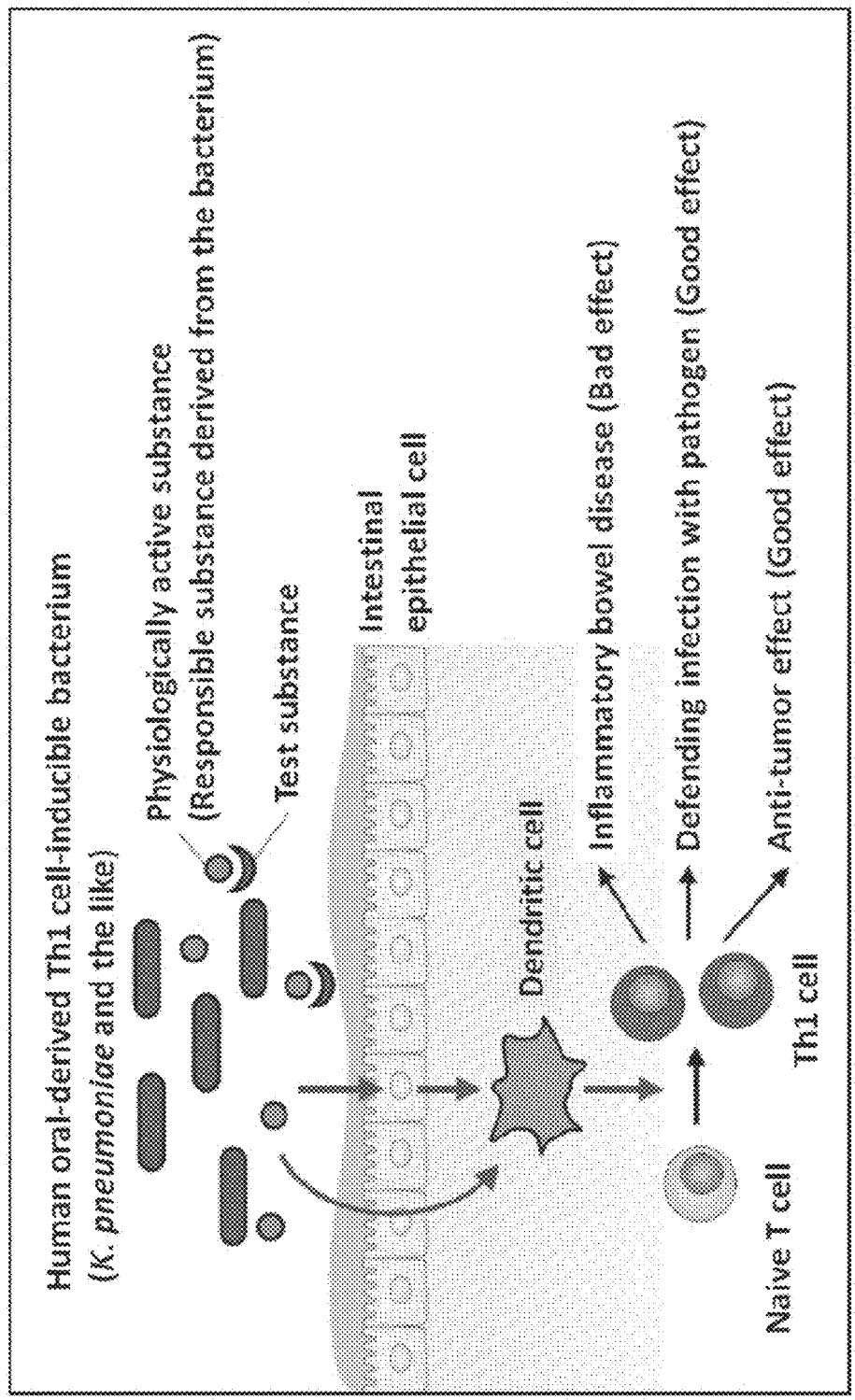
FIG. 51 is a schematic diagram for illustrating an example of an embodiment of the present invention.
Figure 52:
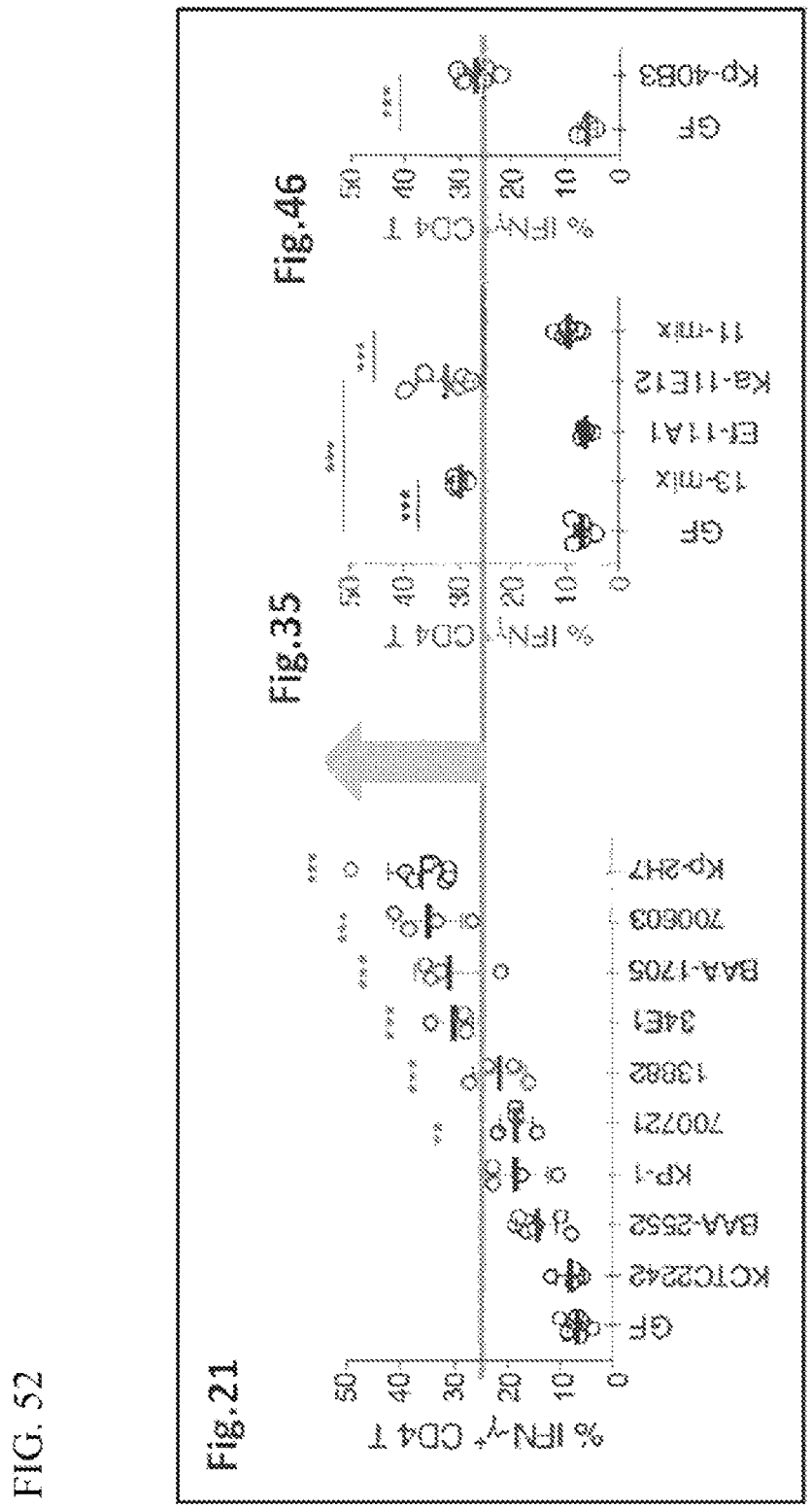
FIG. 52 shows graphs where differences from thresholds at 25% in FIGS. 21, 35, and 46 are defined as relative induction levels.

When colonizing in an intestine, the above-described Th1 cell-inducible bacterium induces Th1 cell proliferation or activation and enhances an immune response, consequently inducing a disease such as Crohn's disease and ulcerative colitis attributable to Th1 cells. Hence, removing the bacterium from the intestine suppresses the Th1 cell induction and suppresses the immune response, thereby leading to the treatment or the like of the disease. Moreover, as shown in FIG. 51, when a physiologically active substance derived from the bacterium, which induces Th1 cells and induces the immunity activation, binds to a substance (which corresponds to the "test substance" in the diagram) capable of binding to the physiologically active substance, if the induction actions are suppressed, the Th1 cell induction is suppressed, and the immune response is suppressed, leading to the treatment or the like of the disease.

Thus, the present invention provides: a composition for suppressing Th1 cell proliferation or activation, a composition for suppressing immunity, or a composition for treating, alleviating, or preventing a disease attributable to Th1 cells, the compositions each comprising, as an active ingredient, a substance having an antibacterial activity against the bacterium capable of inducing Th1 cell proliferation or activation in an intestine or a substance capable of binding to a physiologically active substance derived from the bacterium.

The "substance having an antibacterial activity against the bacterium capable of inducing Th1 cell proliferation or activation in an intestine" incorporated as the active ingredient in the composition of the present invention is not particularly limited, as long as the substance has the aforementioned activity. Examples of the substance include antibiotics, bacterium-lysing substances (such as phages, lysozymes), antibodies capable of specifically recognizing the bacterium, and the above-described bacterium-specific antigen. Moreover, examples of the antibiotics include meropenem, tetracycline, polymyxin-B, trimethoprim, gentamycin, and the like against Kp-2H7 and the like; and meropenem, tetracycline, trimethoprim, ampicillin, gentamycin, streptomycin, spectinomycin, and the like against Ka-11E12 and the like. Besides, the examples further include antibiotics, shown in Tables 12 and 14, to which the bacterium capable of inducing Th1 cell proliferation or activation in an intestine exhibits a susceptibility.

The "physiologically active substance derived from the bacterium capable of inducing Th1 cell proliferation or activation in an intestine" is as described above. Moreover, the substance capable of binding to the physiological activity should be a substance capable of binding to the physiologically active substance so as to suppress the inductions of Th1 cells and immunity activation by the physiologically active substance. Examples of the substance capable of binding to the physiologically active substance include antibodies capable of binding to the physiologically active substance, and low-molecular weight compounds capable of binding to the physiologically active substance. Moreover, as a preferable embodiment, such substances include a substance capable of binding to a binding site to TLR involving MyD88/Trif in the physiologically active substance.

Further, the composition of the present invention may comprise multiple types of the substance having an antibacterial activity and/or the antibody capable of binding to the physiologically active substance. Alternatively, the composition can be used in combination. As a result of the combinational use, when the composition is provided or absorbed (when the composition is used in combination), the multiple substances may exist in two or more compositions.

The composition of the present invention may be in the form of a pharmaceutical composition, a food or drink (including an animal feed), or a reagent used for a research purpose (for example, in vitro or in vivo experiment).

As described above, the composition of the present invention suppresses the immunity and the Th1 induction in an intestine by the bacterium capable of inducing Th1 cell proliferation or activation in an intestine. Accordingly, the composition of the present invention is suitably used as a pharmaceutical composition, food, or drink for treating, preventing, or alleviating the above-described disease attributable to Th1 cells.

The composition of the present invention can be formulated by known formulation methods. The composition can be used for administration orally, parenterally (for example, intestinally, intramuscularly, intravenously, intratracheally, intranasally, transdermally, intradermally, subcutaneously, intraocularly, intravaginally, intraperitoneally, rectally or by inhalation), or through multiple routes consisting of a combination of these, in the form of, for example, a capsule, a tablet, a pill, a liquid, a powder, a granule, a fine granule, a film coating agent, a pellet, a troche, a sublingual tablet, a masticatory, a buccal, a paste, a syrup, a suspension, an elixir, an emulsion, an endermic liniment, an ointment, a plaster, a poultice, a percutaneous absorption preparation, a lotion, an inhalation, an aerosol, an injection, a suppository, or the like.

When formulated, these can be combined as appropriate with a pharmacologically acceptable carrier or a carrier acceptable as a food or drink, concretely, sterile water or a saline, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a disintegrant, a buffer, a coating agent, a lubricant, a colorant, a sweetener, a viscous agent, a corrigent, a solubilizer, or other additives.

Meanwhile, in these formulations, from the viewpoints such as more efficiently suppressing the immunity and the Th1 cell proliferation or activation in an intestine, particularly in formulating a pharmaceutical preparation for oral administration, the composition of the present invention may be combined with a composition which enables an efficient delivery to an intestine. Such a composition enabling the delivery to an intestine is not particularly limited, and known compositions can be employed as appropriate. Examples thereof include pH sensitive compositions, compositions for suppressing the release into the intestinal tract (such as cellulose-based polymers, acrylic acid polymers and copolymers, vinyl acid polymers and copolymers), bioadhesive compositions which specifically adhere to mucosas of the intestinal tract (for example, a polymer described in the specification of U.S. Pat. No. 6,368,586), protease inhibitor-containing compositions, and compositions specifically degraded by enzymes in the intestine).

In addition, in the case where the composition for suppressing Th1 cell proliferation or activation or immunity of the present invention is used as a pharmaceutical composition, the composition may further comprise a known substance (for example, an anti-inflammatory agent, an immunosuppressant) used for treating, preventing, or alleviating a disease attributable to Th1 cells, or may be used in combination with such a substance.

In the case where the composition of the present invention is used as a food or drink, the food or drink may be, for example, a health food, a functional food, a food for specified health use, a food with nutrient function claims, a function-labeled food, a nutritional supplementary food, a medical food for the ill, or an animal feed. Concrete examples of the food or drink include liquid foods such as fermented drinks, oil-containing products, soups, dairy drinks, refreshing drinks, tea drinks, alcoholic drinks, energy drinks, and jelly drinks; carbohydrate-containing foods; livestock-processed foods; processed seafoods; vegetable-processed foods; semi-solid foods; fermented foods; confectionaries; retort pouch foods; microwave foods; and the like. The examples further include health foods or drinks prepared in the form of powder, granule, tablet, capsule, liquid, paste, or jelly. Note that, in the present invention, the food or drink can be produced by production techniques known in this technical field. To the food or drink, an active ingredient (for example, a nutrient or the like) for alleviating or preventing a disease attributable to Th1 disease may be added. Moreover, in combination with another ingredient or another functional food which exhibit a function other than the alleviation or the like, a multi-functional food or drink can be prepared.

A product (drug, food, drink, reagent) of the composition of the present invention or a manual thereof may be provided with an indication stating that the product is used for suppressing Th1 cell proliferation or activation, suppressing immunity, or treating, alleviating, or preventing a disease attributable to Th1 disease. Meanwhile, in the case of the food or drink, the product of the composition or the like of the present invention may be provided with an indication of the health function as a health functional food (a food for specified health use, a food with nutrient function claims, a function-labeled food) to be distinguished from general foods by the appearance, target persons, and so forth. Herein, "a product or a manual provided with an indication" means that the indication is attached to the main body, container, package, or the like of the product, or that the indication is provided in the manual, package insert, advertisement, other printed materials, or the like disclosing information on the product. Further, the composition of the present invention may be in the form of a kit.

Additionally, the present invention also provides: a method for suppressing Th1 cell proliferation or activation in a subject, a method for suppressing immunity in the subject, or a method for treating, alleviating, or preventing a disease attributable to Th1 cells in the subject, the methods characterized in that the subject is provided with a composition for suppressing Th1 cell proliferation or activation, a composition for suppressing immunity, or a substance having an antibacterial activity against a Th1 cell-inducible bacterium or a substance capable of binding to a physiologically active substance derived from the bacterium, which serve as the active ingredient of these compositions.

The composition or the active ingredient of the present invention can be used for animals including human as the subject. The animals other than human are not particularly limited, and various domestic animals, poultry, pet animals, experimental animals, and the like can be the subject.

Moreover, the subject to be provided with the composition for inducing Th1 cell proliferation or activation or the like of the present invention or the active ingredient thereof includes animals comprising the bacterium capable of inducing Th1 cell proliferation or activation in an intestine, regardless of the development of the disease attributable to Th1 cells. In addition, from the viewpoint of the prevention, animals which do not comprise or may comprise the bacterium may be provided with the composition or the like of the present invention.

The method for providing the composition or the like of the present invention is not particularly limited. The composition may be orally administered, or may be parenterally administered (for example, administered into an intestine). In the case of oral administration, from the viewpoint of further enhancing the effects of the composition or the like of the present invention, the subject to be provided with the composition or the like of the present invention is preferably provided with a proton-pump inhibitor (PPI) or the like in advance to reduce the production of gastric acid.

Moreover, when the composition or the like of the present invention is provided, the amount provided can be selected as appropriate by those skilled in the art, depending on the age, body weight, disease symptom, and health state of the subject, the type of the composition (such as drug, food, drink), the providing method, and so forth.

<Screening Method 1 for Bacterium Capable of Inducing or Suppressing Th1 Cells in Intestine>

In the present invention, as a result of providing germ-free mice with human saliva, bacteria capable of inducing Th1 cell proliferation or activation in an intestine have been successfully identified. Thus, the present invention provides the following screening method.

A screening method for a bacterium capable of inducing Th1 cell proliferation or activation in an intestine, the method comprising the steps of:
    providing a non-human germ-free animal with a test sample;
    detecting the number or activity of Th1 cells in an intestine of the non-human germ-free animal; and
    isolating a bacterium from a sample in the intestine of the non-human germ-free animal from which Th1 cell proliferation or activation is detected in the previous step.

In the present invention, the "test sample" should be a sample derived from human. Examples thereof include samples (such as saliva) in human oral cavities, samples in human urinary bladders, samples in human vaginas, and samples (such as urine) in human ureters, samples in human intestines, or cultures thereof. Moreover, from the viewpoint of enhancing the screening efficiency, samples in oral cavities derived from human having a disease attributable to Th1 cells are suitably used.

In the present invention, the "non-human germ-free animal" means an animal born and grown under a germ-free condition, excluding human. Examples of the animals other than human include mice, rats, monkeys, pigs, cattle, horses, sheep, goats, chickens, ducks, ostriches, domesticated ducks, dogs, cats, rabbits, hamsters, and the like, but are not limited thereto. Additionally, among these animals, mice are suitably used.

In the present invention, the method for "providing" a non-human germ-free animal with a test sample is not particularly limited, but the test sample is normally orally administered.

Further, the Th1 cell proliferation or activation in an intestine is "detected" by detecting a marker (for example, CD4 and IFN-γ) specific to Th1 cells. The detection can be performed by known methods. Examples thereof include detection methods using an antibody (immunological methods) such as flow cytometry, imaging cytometry, ELISA methods, radioimmunoassay, immunohistochemical staining, immunoprecipitation, immunoblotting, and antibody array analyses. Moreover, the timing of the detection is not particularly limited, and can be adjusted as appropriate by those skilled in the art, depending on the type of the animal used, and so forth. Further, in the immunological methods, if a significant increase in the marker specific to Th1 cells is found in comparison with a control (for example, a non-human germ-free animal not provided with the test sample), it can be determined that the Th1 cell proliferation or activation is detected. The control and the determination method are not limited thereto.

In the present invention, the "sample in the intestine" should be a sample containing the Th1 cell-inducible bacterium colonized in the non-human germ-free animal. Examples of the sample include fecal samples of the animal, or cultures thereof. Moreover, the method for "isolating" the bacterium from the sample in the intestine is not particularly limited, and includes known methods (dilution culturing, single-colony culturing by culturing on a plate).

Note that if the bacterium capable of inducing Th1 cell proliferation or activation in an intestine cannot be obtained by performing the screening method of the present invention one time, the obtained bacterium-containing sample in the intestine is provided instead of the test sample to another non-human germ-free animal, and the above-described screening is performed multiple times, so that the bacterium capable of inducing Th1 cell proliferation or activation in an intestine can be isolated.

Additionally, as an application of the above-described method, the present invention can also provide the following screening method.

A screening method for a bacterium capable of suppressing Th1 cell proliferation or activation in an intestine, the method comprising the steps of:
    providing a non-human germ-free animal with a test sample;
    detecting the number or activity of Th1 cells in an intestine of the non-human germ-free animal; and
    isolating a bacterium from a sample in the intestine of the non-human germ-free animal from which suppression of Th1 cell proliferation or activation is detected in the previous step.

<Screening Method 1 for Physiologically Active Substance Capable of Inducing or Suppressing Th1 Cells in Intestine>

According to the present invention, a bacterium capable of inducing Th1 cell proliferation or activation in an intestine can be further screened for a physiologically active substance responsible for the induction. Accordingly, the present invention also provides the following screening method.

A screening method for a physiologically active substance capable of inducing Th1 cell proliferation or activation in an intestine, the method comprising the steps of:
    providing a non-human germ-free animal with physiologically active substance derived from a bacterium capable of inducing Th1 cell proliferation or activation in an intestine;
    detecting the number or activity of Th1 cells in an intestine of the non-human germ-free animal; and
    determining that the physiologically active substance is a physiologically active substance capable of inducing Th1 cell proliferation or activation in an intestine, if Th1 cell proliferation or activation is detected in the previous step.

The "physiologically active substance" used in the method means a substance incorporated in the bacterium capable of inducing Th1 cell proliferation or activation in an intestine, a secretion from the bacterium, or a metabolite by the bacterium, and may a single substance isolated when used in the method, or may be a fraction (for example, polypeptide fraction, polynucleotide fraction, carbohydrate fraction, lipid fraction, or low-molecular weight metabolite fraction of the bacterium or the culture supernatant) containing multiple substances. Note that when such a fraction containing multiple substances is used in the method, it is also possible to identify a single physiologically active substance capable of inducing Th1 cell proliferation or activation in an intestine by further fractionating a fraction determined to be the physiologically active substance capable of inducing Th1 cell proliferation or activation in an intestine, and then further performing the method (the method is repeated multiple times as necessary).

Note that other features of the screening method (such as the non-human germ-free animal, methods, conditions) are the same as those in <Screening Method 1 for Bacterium capable of Inducing or Suppressing Th1 Cells in Intestine> described above.

Additionally, as an application of the above-described method, the present invention can also provide the following screening method.

A screening method for a physiologically active substance capable of suppressing Th1 cell proliferation or activation in an intestine, the method comprising the steps of:
  providing a non-human germ-free animal with physiologically active substance derived from a bacterium capable of suppressing Th1 cell proliferation or activation in an intestine;
  detecting the number or activity of Th1 cells in an intestine of the non-human germ-free animal; and
  determining that the physiologically active substance is a physiologically active substance capable of suppressing Th1 cell proliferation or activation in an intestine, if suppression of Th1 cell proliferation or activation is detected in the previous step.

<Model Animal>

As described above, the present invention has revealed that, as a result of orally providing mice with bacteria capable of inducing Th1 cell proliferation or activation in an intestine, the bacteria colonize in the intestines, induce Th1 cells, and cause inflammation.

Thus, the present invention provides a non-human animal or a non-human model animal of a disease attributable to Th1 cells, the animals comprising the bacterium capable of inducing Th1 cell proliferation or activation in an intestine and colonized in intestines of the animals.

Moreover, as described above, such animals can be produced by providing a non-human animal with the bacterium capable of inducing Th1 cell proliferation or activation in an intestine to allow the bacterium to colonize in an intestine of the animal. Thus, the present invention also provides the production method.

The "bacterium capable of inducing Th1 cell proliferation or activation in an intestine" to be provided to a non-human animal is as described above, and may be living cells or dead cells. Moreover, depending on the usage of the incorporated active ingredient, the bacterium may be modified (for example, genetically modified). Such a modification is not particularly limited. An example of the modification includes the enhancement of the action of inducing Th1 cell proliferation or activation in an intestine.

The "non-human animal" to be provided with the above-described bacterium is not particularly limited. Examples of the non-human animal include mice, rats, monkeys, pigs, cattle, horses, sheep, goats, chickens, ducks, ostriches, domesticated ducks, dogs, cats, rabbits, hamsters, and the like, but are not limited thereto. Additionally, among these animals, mice are suitably used. Further, the "non-human animal" is preferably a non-human germ-free animal born and grown under a germ-free condition from the viewpoints such as facilitating the colonization by the bacterium. Furthermore, from the viewpoint that inflammation is more likely to occur, the "non-human animal" is preferably a non-human animal in which the IL-10 activity is suppressed.

Note that the suppression of the IL-10 activity includes not only the suppression of the function, but also the suppression of the expression (expression at the translation level or the transcription level). The function can be suppressed by administering an IL-10 specific antibody, aptamer, or the like to the non-human animal. Moreover, the expression can be suppressed by gene recombination (what is called, knock-out), genome editing, or by administering siRNA, shRNA, or antisense RNA.

In the present invention, the method for "providing" a non-human animal with the bacterium is not particularly limited. Normally, the bacterium is orally administered, but may be parenterally administered (for example, administered into an intestine). In the case of oral administration, from the viewpoints such as facilitating the colonization by the bacterium, the non-human animal is preferably provided with a proton-pump inhibitor (PPI) or the like in advance to reduce the production of gastric acid, or provided with an antibiotic in advance. Moreover, the non-human animal should be provided with a single strain of the bacterium, but may be provided with multiple strains thereof.

<Screening Method 1 for Substance Capable of Inducing or Suppressing Th1 Cells in Intestine>

As described above, in a non-human animal comprising the bacterium capable of inducing Th1 cell proliferation or activation in an intestine and colonized in an intestine of the animal, the Th1 cell proliferation or activation is induced in the intestine. Hence, such a non-human animal can be suitably used as a non-human model animal of a disease attributable to Th1 cells. Thus, the present invention also provides the following screening method using the model animal.

A screening method for a substance capable of inducing Th1 cell proliferation or activation in an intestine, the method comprising the steps of:
  providing a test substance to a non-human animal comprising the bacterium capable of inducing Th1 cell proliferation or activation in an intestine and colonized in an intestine of the animal;
  detecting the number or activity of Th1 cells in the intestine of the non-human animal; and
  determining that the test substance is a substance capable of inducing Th1 cell proliferation or activation in an intestine, if the number or activity of the Th1 cells detected in the previous step is more than that in a case without the test substance provided.

The "test substance" used in the method is not particularly limited. Examples thereof include synthetic low-molecular-weight compounds, antibodies, polypeptides, polynucleotides, lipids, sugars (such as monosaccharides, disaccharides, oligosaccharides, carbohydrates), libraries constituted of these substances, liquid extracts and cultures (such as culture supernatants) of cells (bacteria, plant cells, animal cells), secretions from bacteria, metabolites by bacteria, extracts derived from marine organisms, plants, or animals, soils, and random phage peptide display libraries.

The "bacterium capable of inducing Th1 cell proliferation or activation in an intestine" is as described above.

In the present invention, the method for "providing" the non-human animal with a test substance is not particularly limited. Normally, the test substance is orally administered, but may be parenterally administered (for example, administered into an intestine). In the case of oral administration, from the viewpoints such as facilitating the delivery of the test substance to an intestine, the non-human animal is preferably provided with a proton-pump inhibitor (PPI) or the like in advance to reduce the production of gastric acid.

Note that other features of the screening method (such as the non-human germ-free animal, methods, conditions) are the same as those in <Screening Method 1 for Bacterium capable of Inducing or Suppressing Th1 Cells in Intestine> described above.

Additionally, as an application of the above-described method, the present invention can also provide the following screening methods.

A screening method for a substance having an activity of inducing or worsening a disease attributable to Th1 cells, the method comprising the steps of:

providing a test substance to a non-human model animal of a disease attributable to Th1 cells, the animal comprising the bacterium capable of inducing Th1 cell proliferation or activation in an intestine and colonized in an intestine of the animal;

detecting a degree of a lesion of the disease attributable to Th1 cells in the non-human animal; and determining that the test substance is a substance having an activity of inducing or worsening a disease attributable to Th1 cells, if the degree of the lesion detected in the previous step is more than that in a case without the test substance provided.

A screening method for a substance capable of suppressing Th1 cell proliferation or activation in an intestine, the method comprising the steps of:

providing a test substance to a non-human animal comprising the bacterium capable of inducing Th1 cell proliferation or activation in an intestine and colonized in an intestine of the animal;

detecting the number or activity of Th1 cells in the intestine of the non-human animal; and determining that the test substance is a substance capable of suppressing Th1 cell proliferation or activation in an intestine, if the number or activity of the Th1 cells detected in the previous step is less than that in a case without the test substance provided.

A screening method for a substance having an activity of treating, alleviating, or preventing a disease attributable to Th1 cells, the method comprising the steps of:

providing a test substance to a non-human model animal of a disease attributable to Th1 cells, the animal comprising the bacterium capable of inducing Th1 cell proliferation or activation in an intestine and colonized in an intestine of the animal;

detecting a degree of a lesion of the disease attributable to Th1 cells in the non-human animal; and determining that the test substance is a substance having an activity of treating, alleviating, or preventing a disease attributable to Th1 cells, if the degree of the lesion detected in the previous step is less than that in a case without the test substance provided.

Figure 13:
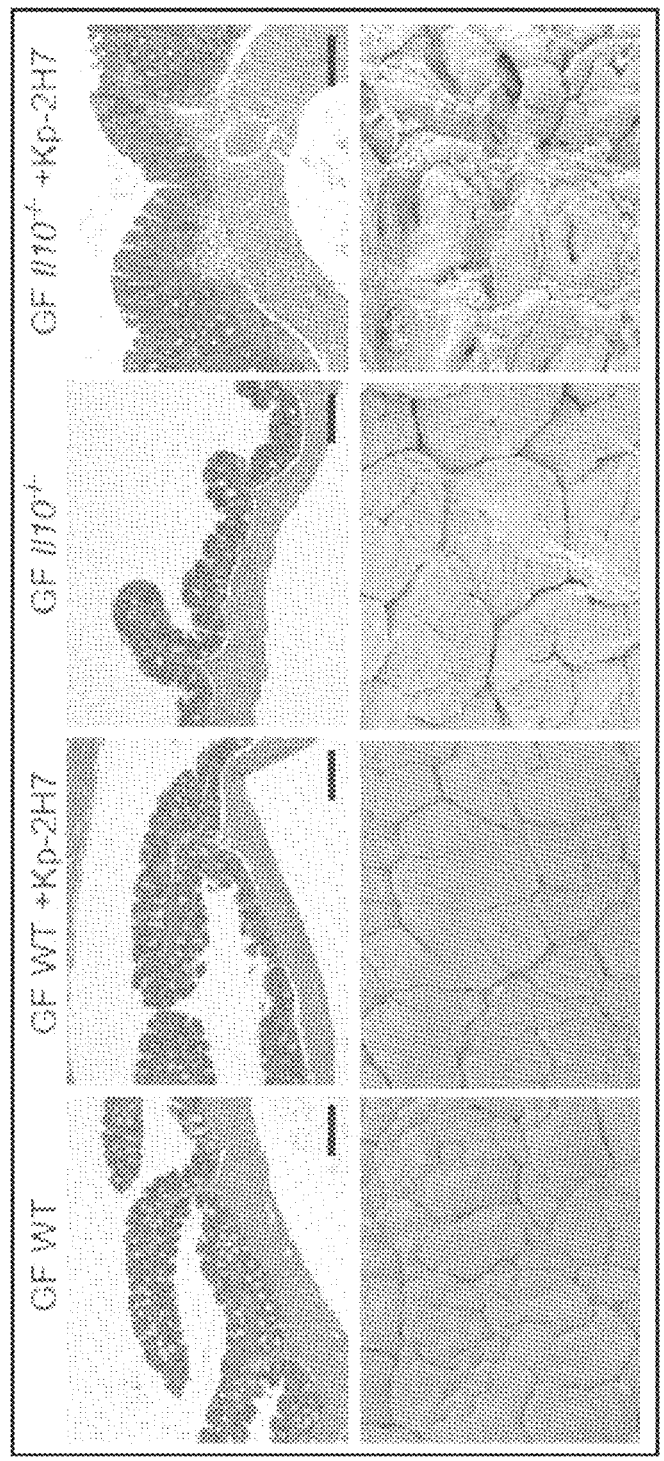
FIG. 13 shows photographs for illustrating the results of microscope observation of the proximal colons of Kp-2H7-colonized GF wildtype or GF Il10⁻/⁻ mice. In the figure, "GF WT" and "GF Il10⁻/⁻" respectively indicate the results of the GF wildtype and GF Il10/mice. "GF WT+Kp-2H7" and "GF Il10⁻/⁻+Kp-2H7" respectively indicate the results of individual GF wildtype and GF Il10⁻/⁻ mice monocolonized with Kp-2H7. Moreover, representative examples of the H&E staining analysis result are shown at the top, and representative examples of the scanning electron microscope analysis result are shown at the bottom. The scale bars represent 200 μm
Figure 14:
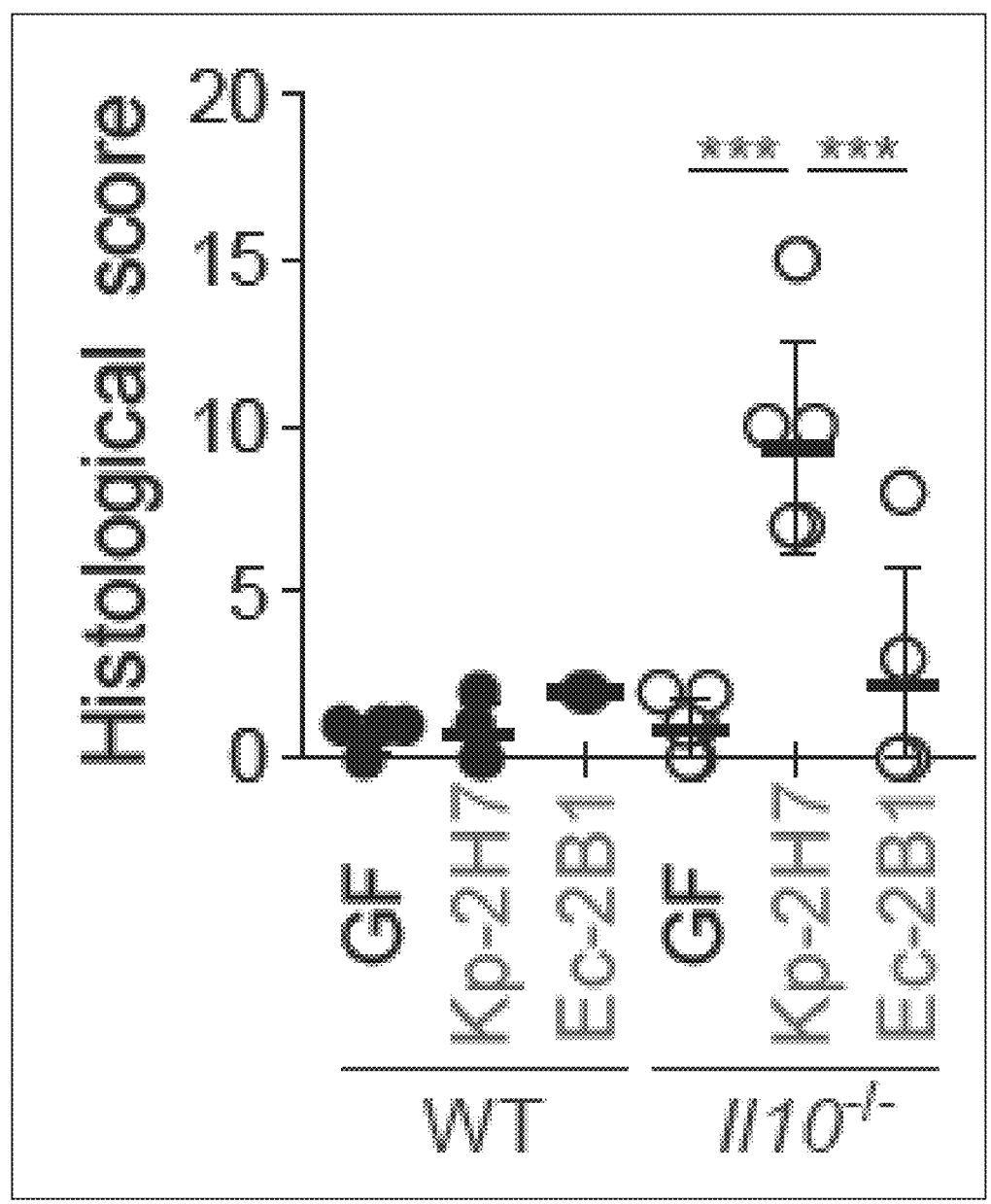
FIG. 14 is a graph for illustrating the result of analyzing the histological colitis scores of the proximal colons of Kp-2H7- or Ec-2B1-monocolonized GF wildtype or GF Il10⁻/⁻ mice. In the graph, "GF" indicates the result of a bacterium-unadministered group. Each point represents data on an individual mouse. Error bars indicate means±standard deviations. *** indicates $P<0.001$ (based on one-way analysis of variance (ANOVA) followed by Tukey's post hoc test).
Figure 15:
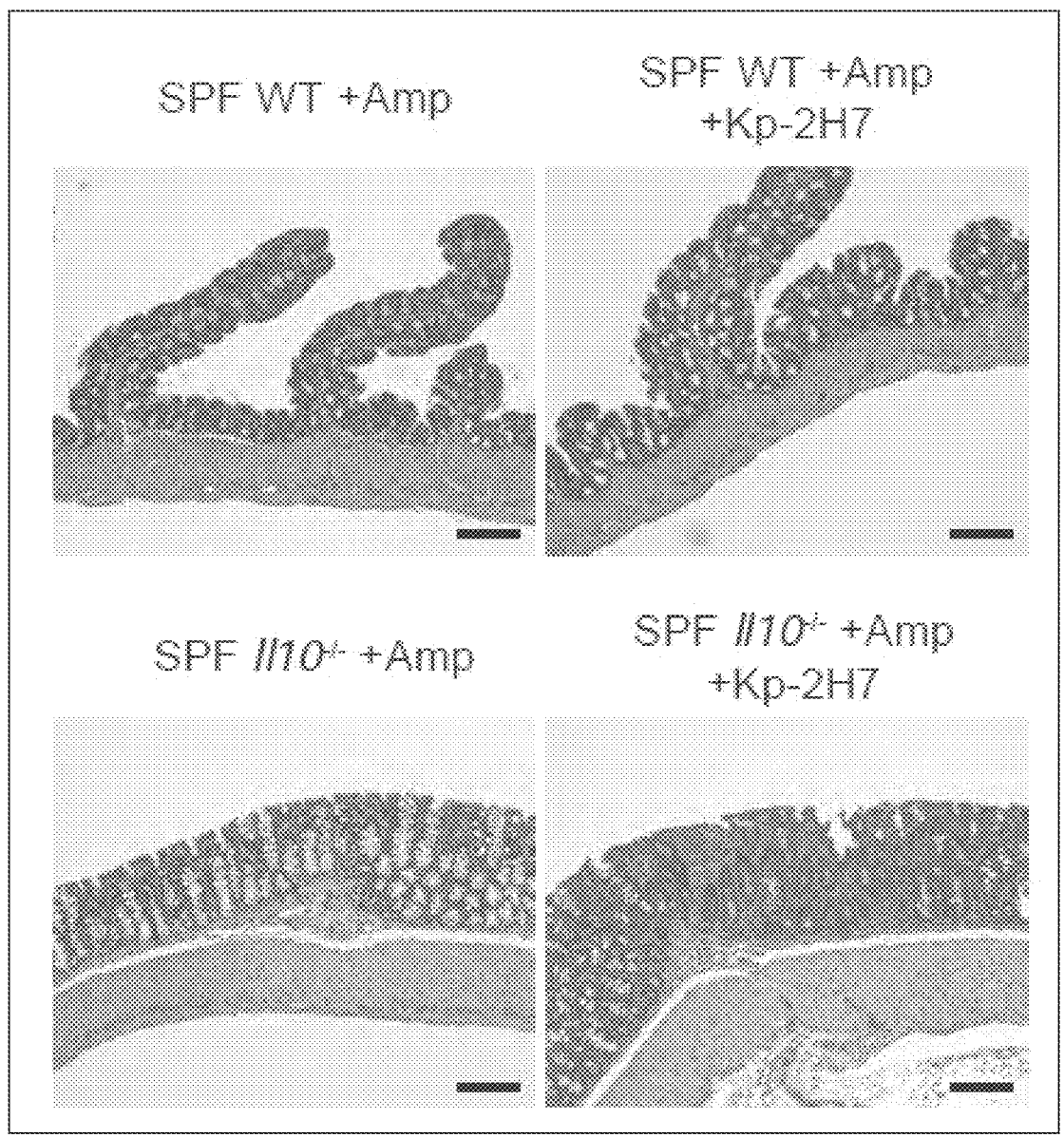
FIG. 15 shows photographs for illustrating the result of microscope observation of the proximal colons of SPF B6 mice (SPF WT) or SPF Il10⁻/⁻ mice continuously treated with an antibiotic (Amp: 200 mg/L ampicillin) via the drinking water, starting 4 days before oral administration of 2×10⁸ CFU Kp-2H7, or not subjected to the administration. The figure shows representative examples of the H&E staining analysis result obtained 3 weeks after the Kp-2H7 inoculation. The scale bars represent 200 μm.
Figure 16:
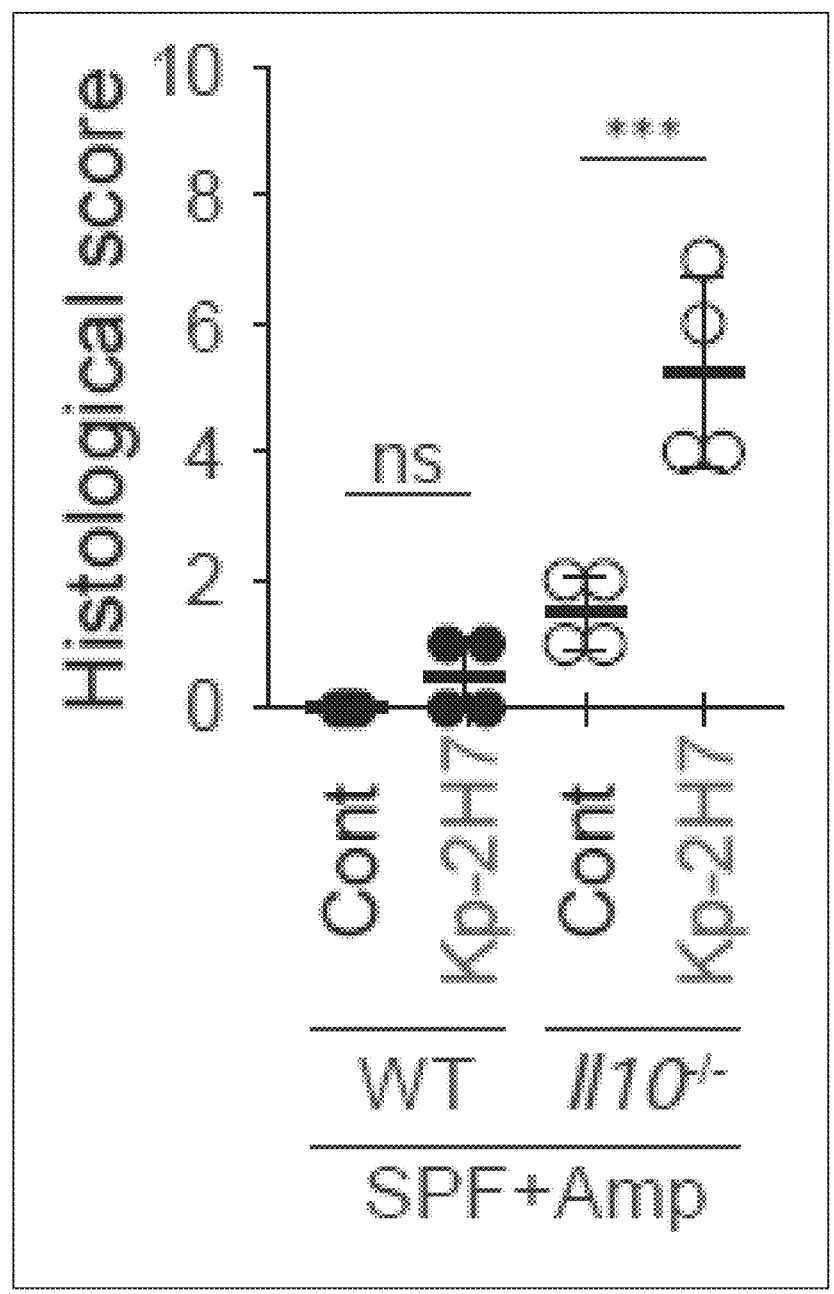
FIG. 16 is a graph for illustrating the result of analyzing the histological colitis scores of the proximal colons of the SPF B6 mice or SPF Il10$^{-/-}$ mice continuously treated with an antibiotic (Amp: 200 mg/L ampicillin) via the drinking water, starting 4 days before the oral administration of 2×10⁸ CFU Kp-2H7, or not subjected to the administration. In the graph, "Cont" indicates the Kp-2H7-unadministered group. Each point represents data on an individual mouse. Error bars indicate means±standard deviations. ns indicates that no significant difference was found (P>0.05), and indicates P<0.001 (based on one-way analysis of variance (ANOVA) followed by Tukey's post hoc test).
Figure 17:
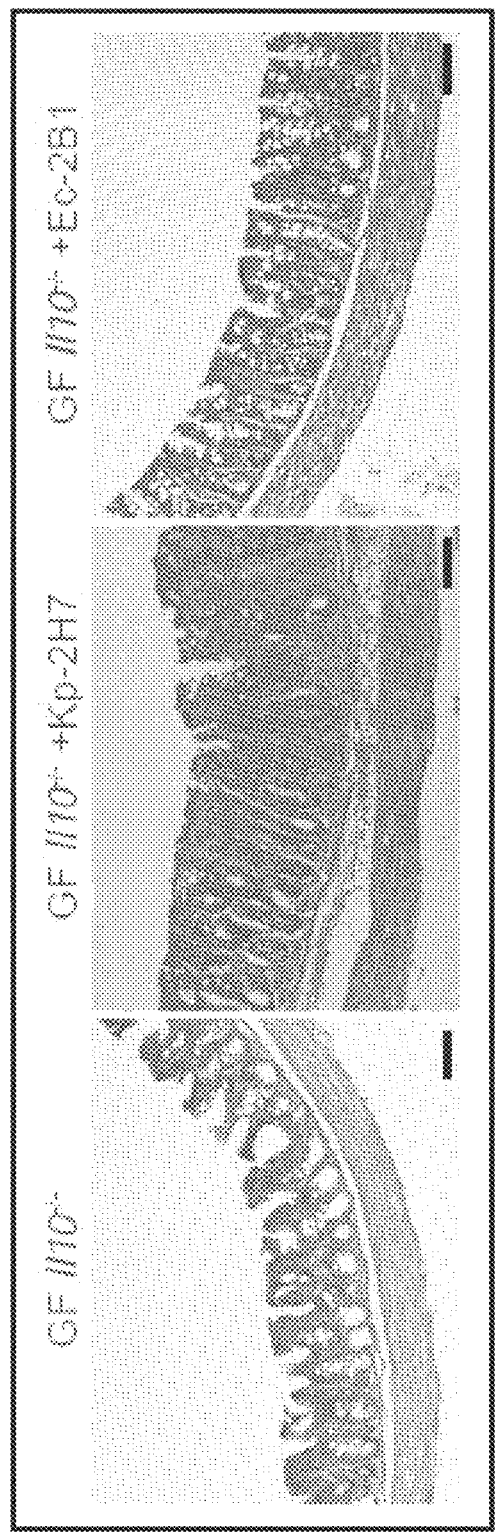
FIG. 17 shows photographs for illustrating the result of microscope observation of the proximal colons of unmonocolonized, Kp-2H7-monocolonized, and EC-2B1-monocolonized GF Il10$^{-/-}$ mice. The figure shows representative examples of the H&E staining analysis result. The scale bars represent 200 μm

Note that, in the present invention, the "lesion" of the disease attributable to Th1 cells is not particularly limited, and can be selected as appropriate by those skilled in the art, depending on the disease of the subject. For example, in a case where the disease is an inflammatory bowel disease such as Crohn's disease and ulcerative colitis, the lesion can be evaluated by observing the degree of inflammation in the intestine as shown in FIGS. 13, 15, and 17. Moreover, the lesion can also be evaluated based on a disease score set for each disease (for example, for ulcerative colitis and the like, "disease activity index (DAI)," see S. Wirtz, C. Neufert, B. Weigmann, M. F. Neurath, Nat Protoc 2, 541 (2007)).

<Screening Method 2 for Bacterium Capable of Inducing or Suppressing Th1 Cells in Intestine>

With respect to the present invention, in an intestine, it is assumed as shown in FIG. 51 that a Th1 cell-inducible bacterium or a physiologically active substance derived from the bacterium is incorporated by an intestinal epithelial cell and passed to a dendritic cell, or that the physiologically active substance is directly trapped by a dendritic cell. Furthermore, it is assumed that a cytokine produced by a dendritic cell presenting the physiologically active substance as an antigen induces differentiation from a naive T cells to Th1 cells.

Hence, constructing such a system in an intestine makes it possible to evaluate the activity of inducing Th1 cells, without using animals as described above. Thus, the present invention also provides the following screening method.

A screening method for a bacterium capable of inducing Th1 cell proliferation or activation in an intestine, the method comprising the steps of:

adding a test bacterium to an intestinal epithelial cell in a system containing the intestinal epithelial cell and a peripheral blood mononuclear cell;

detecting the number or activity of Th1 cells in the system; and determining that the test bacterium is a bacterium capable of inducing Th1 cell proliferation or activation in an intestine, if the induction of Th1 cell proliferation or activation is detected in the previous step.

In the present invention, the "test bacterium" is not particularly limited. Examples thereof includes human oral bacteria, bacteria in human urinary bladders, bacteria in human vaginas, bacteria in human ureters, bacteria in human urines, and bacteria in human intestines.

In the present invention, the "intestinal epithelial cell" means a cell present at the luminal surface in an intestine, and the cell is involved in nutrient absorption and immune response in the intestinal tract. The "peripheral blood mononuclear cell" means a cell group (PBMC) including lymphocytes and monocytes derived from peripheral blood. In the present invention, the peripheral blood mononuclear cell may be peripheral blood itself. Moreover, the origins of the intestinal epithelial cell and the peripheral blood mononuclear cell are not particularly limited, and include animals including human (humans, mice, rats, monkeys). Human-derived cells are suitably used.

The "system containing an intestinal epithelial cell and a peripheral blood mononuclear cell" should be a culture system containing these cells. The intestinal epithelial cell is preferably in contact with the peripheral blood mononuclear cell. Moreover, the system is more preferably a culture system in which a layer containing the peripheral blood mononuclear cell serves as a lower layer while a layer containing the intestinal epithelial cell serves as an upper layer. The culture system can be constructed, for example, by stacking the intestinal epithelial cell on the peripheral blood mononuclear cell. Alternatively, the culture system can also be constructed, for example, by using commercially available co-culture systems (such as Transwell (registered trademark) culture system) such that monolayers of the intestinal epithelial cell and the peripheral blood mononuclear cell are cultured in an upper compartment and a lower compartment, respectively.

Note that other features of the screening method (such as methods, conditions) are the same as those in <Screening Method 1 for Bacterium capable of Inducing or Suppressing Th1 Cells in Intestine> described above.

Additionally, as an application of the above-described method, the present invention can also provide the following screening method.

A screening method for a bacterium capable of suppressing Th1 cell proliferation or activation in an intestine, the method comprising the steps of:
  adding a test bacterium to an intestinal epithelial cell in a system containing the intestinal epithelial cell and a peripheral blood mononuclear cell;
  detecting the number or activity of Th1 cells in the system; and
  determining that the test bacterium is a bacterium capable of suppressing Th1 cell proliferation or activation in an intestine, if suppression of Th1 cell proliferation or activation is detected in the previous step.

<Screening Method 2 for Physiologically Active Substance Capable of Inducing or Suppressing Th1 Cells in Intestine>

According to the present invention, a bacterium capable of inducing Th1 cell proliferation or activation in an intestine can be further screened for a physiologically active substance responsible for the induction. Accordingly, the present invention also provides the following screening method.

A screening method for a physiologically active substance capable of inducing Th1 cell proliferation or activation in an intestine, the method comprising the steps of:
  adding a physiologically active substance derived from a bacterium capable of inducing Th1 cell proliferation or activation in an intestine to an intestinal epithelial cell in a system containing the intestinal epithelial cell and a peripheral blood mononuclear cell;
  detecting the number or activity of Th1 cells in the system; and
  determining that the physiologically active substance is a physiologically active substance capable of inducing Th1 cell proliferation or activation in an intestine, if Th1 cell proliferation or activation is detected in the previous step.

Note that the "physiologically active substance" used in the method is as described in <Screening Method 1 for Physiologically Active Substance capable of Inducing or Suppressing Th1 Cells in Intestine>. Moreover, other features of the screening method (such as methods, conditions) are the same as those in <Screening Method 1 for Bacterium capable of Inducing or Suppressing Th1 Cells in Intestine> described above.

Further, as an application of the above-described method, the present invention can also provide the following screening method.

A screening method for a physiologically active substance capable of suppressing Th1 cell proliferation or activation in an intestine, the method comprising the steps of:
  adding a physiologically active substance derived from a bacterium capable of suppressing Th1 cell proliferation or activation in an intestine to an intestinal epithelial cell in a system containing the intestinal epithelial cell and a peripheral blood mononuclear cell;
  detecting the number or activity of Th1 cells in the system; and
  determining that the physiologically active substance is a physiologically active substance capable of suppressing Th1 cell proliferation or activation in an intestine, if suppression of Th1 cell proliferation or activation is detected in the previous step.

<Kit for Evaluating Th1 Cell Proliferation or Activation>

As described above, according to the present invention, the Th1 cell induction in an intestine can be replicated in vitro.

Thus, the present invention also provides a kit for evaluating Th1 cell proliferation or activation, the kit comprising: an intestinal epithelial cell; and a peripheral blood mononuclear cell, or a kit for evaluating Th1 cell proliferation or activation, the kit comprising: the bacterium capable of inducing Th1 cell proliferation or activation in an intestine; an intestinal epithelial cell; and a peripheral blood mononuclear cell.

Note that the bacterium, the intestinal epithelial cell, and the peripheral blood mononuclear cell are as described in <Screening Method 2 for Bacterium capable of Inducing or Suppressing Th1 Cells in Intestine>. Additionally, the evaluation kit may comprise, in addition to the bacterium and the cells, a medium or a culture system (such as plates) for maintaining or culturing these, and a reagent (CD4 antibody, IFN-γ antibody, secondary antibody, labeling substance, or the like) for detecting Th1 cells. Further, the evaluation kit may comprise an instruction for the kit.

<Screening Method 2 for Substance Capable of Inducing or Suppressing Th1 Cells in Intestine>

As described above, the system containing an intestinal epithelial cell and a peripheral blood mononuclear cell, or the system further containing the bacterium capable of inducing Th1 cell proliferation or activation in an intestine, can be suitably used to evaluate Th1 cell proliferation or activation. Thus, the present invention also provides the following screening methods using such a system.

A screening method for a substance capable of inducing Th1 cell proliferation or activation in an intestine, the method comprising the steps of:
  adding a test substance and a bacterium capable of inducing Th1 cell proliferation or activation in an intestine to an intestinal epithelial cell in a system containing the intestinal epithelial cell and a peripheral blood mononuclear cell;
  detecting the number or activity of Th1 cells in the system; and
  determining that the test compound is a substance capable of inducing Th1 cell proliferation or activation in an intestine, if the number or activity of the Th1 cells detected in the previous step is more than that in a case without the test substance added.

A screening method for a substance capable of suppressing Th1 cell proliferation or activation in an intestine, the method comprising the steps of:
  adding a test substance and a bacterium capable of inducing Th1 cell proliferation or activation in an intestine to an intestinal epithelial cell in a system containing the intestinal epithelial cell and a peripheral blood mononuclear cell;
  detecting the number or activity of Th1 cells in the system; and
  determining that the test substance is a substance capable of suppressing Th1 cell proliferation or activation in an intestine, if the number or activity of the Th1 cells detected in the previous step is less than that in a case without the test compound added.

Note that the materials (system, bacterium, test substance), methods, conditions, and so forth used in these methods are as described in <Screening Method 2 for Bacterium capable of Inducing or Suppressing Th1 Cells in Intestine> and <Screening Method 1 for Substance capable of Inducing or Suppressing Th1 Cells in Intestine>.

<Composition 1 for Testing Disease Attributable to Th1 Cells>

As described above, the present invention has revealed that when the bacterium capable of inducing Th1 cell proliferation or activation in an intestine colonizes in an intestine, Th1 cells are induced, inducing a disease attributable to the Th1 cells. Hence, a disease attributable to Th1 cells can be tested by detecting the presence of the bacterium.

Thus, the present invention provides the following compositions for testing a disease attributable to Th1 cells.

A composition for testing a disease attributable to Th1 cells, the composition comprising an antibody capable of specifically recognizing the bacterium capable of inducing Th1 cell proliferation or activation in an intestine.

A composition for testing a disease attributable to Th1 cells, the composition comprising a polynucleotide for detecting a nucleotide sequence specific to the bacterium capable of inducing Th1 cell proliferation or activation in an intestine.

In the present invention, the "antibody capable of specifically recognizing a bacterium capable of inducing Th1 cell proliferation or activation in an intestine" may be a polyclonal antibody, a monoclonal antibody, or a functional fragment of an antibody (for example, Fab, Fab', F(ab')2, a variable region fragment (Fv), a disulfide-stabilized Fv, a single-chain Fv (scFv), sc (Fv)2, a diabody, a polyspecific antibody, or polymers thereof), as long as it is possible to specifically recognize the bacterium. If the antibody of the present invention is a polyclonal antibody, the polyclonal antibody can be obtained as follows. Concretely, a host animal is immunized with an antigen (such as the bacterium capable of inducing Th1 cell proliferation or activation in an intestine; a polypeptide, a polynucleotide, a carbohydrate, or a lipid derived from the bacterium). Then, an antiserum from the animal is purified by conventional means (for example, salting-out, centrifugation, dialysis, column chromatography, or the like). Thus, the polyclonal antibody can be obtained. Meanwhile, a monoclonal antibody can be prepared by a hybridoma method or a recombinant DNA method.

Moreover, as the antibody used in the test of the present invention, an antibody bound to a labeling substance can be used. Detecting the labeling substance enables direct measurement of the amount of the antibody bound to the bacterium or a substance derived from the bacterium. The labeling substance is not particularly limited, as long as the labeling substance can bind to the antibody and can be detected by a chemical or optical method. Examples of the labeling substance include fluorescent dyes (such as GFP), enzymes (such as HRP), and radioactive substances.

The testing composition of the present invention may comprise other ingredients acceptable as a composition than the antibody ingredient. Examples of such other ingredients includes carriers, excipients, disintegrants, buffers, emulsifiers, suspensions, stabilizers, preservatives, antiseptics, physiological salts, labeling substances, and secondary antibodies. Further, besides the testing composition, a substrate necessary for detection of the labeling substance, a positive control or a negative control, a buffer solution used to dilute or wash a sample, a tube or a plate used for the reaction between the sample and the antibody of the present invention, or the like can be combined, so that a kit for testing a disease attributable to Th1 cells can also be provided. Meanwhile, in a case where the antibody preparation is an unlabeled antibody, a labeled substance (for example, secondary antibody, Protein G, Protein A, or the like) capable of binding to the antibody can be combined. Additionally, the kit for testing a disease attributable to Th1 cells may comprise an instruction for the kit.

Further, the testing composition of the present invention can also be combined with a device for detecting the antibody of the present invention. Examples of the device include flow cytometers and microplate readers.

In the present invention, the "polynucleotide for detecting a nucleotide sequence specific to the bacterium capable of inducing Th1 cell proliferation or activation in an intestine" is not particularly limited, as long as the sequence specific to the bacterium is detected. Examples of the polynucleotide include any polynucleotides according to the following (a) and (b) each of which has a chain length of at least 15 nucleotides:

(a) a polynucleotide that is a pair of primers designed to flank the specific nucleotide sequence; and
(b) a polynucleotide that is a primer or a probe capable of hybridizing to a nucleotide sequence containing the specific nucleotide sequence.

The polynucleotide of the present invention has a base sequence complementary to a nucleotide sequence of the bacterium capable of inducing Th1 cell proliferation or activation in an intestine. Herein, being "complementary" does not always have to be completely complementary, as long as the hybridization is possible. These polynucleotides have a homology of normally 80% or more, preferably 90% or more, more preferably 95% or more, and particularly preferably 100%, with the nucleotide sequence.

The "chain length" of the polynucleotide of the present invention is normally 15 to 100 nucleotides, preferably 17 to 30 nucleotides, and more preferably 20 to 25 nucleotides, in the case where the polynucleotide is used as the primer. Meanwhile, in the case where the polynucleotide is used as the probe, the chain length is normally 15 to 1000 nucleotides, and preferably 20 to 100 nucleotides.

Note that concrete embodiments of the polynucleotide of the present invention include the following polynucleotides (pairs of primers) for detecting a nucleotide sequence specific to the 2H7 strain belonging to *Klebsiella pneumonia*:

a combination of a scaffold00004_68_F primer (sequence: AATCAAGGGCCCGAGTAAGT [SEQ ID NO: 1]) and a scaffold00004_68_R primer (sequence: CCAAACGCTACGCCATTTAT [SEQ ID NO: 2]); a combination of a scaffold00004_298_F primer (sequence: AGCACTAGCGGCTCTCCTAT [SEQ ID NO: 3]) and a scaffold00004_298_R primer (sequence: ACTTACTCGGGCCCTTGATT [SEQ ID NO: 4]); and a combination of a scaffold00004_307_F primer (sequence: AATCAAGGGCCCGAGTAAGT [SEQ ID NO: 5]) and a scaffold00004_307_R primer (sequence: ATTCAGGGGCTGAAGGAGTT [SEQ ID NO: 6]).

The polynucleotide of the present invention may be a DNA or an RNA, or may have part or all of the nucleotide substituted with an artificial nucleic acid such as LNA (registered trademark, locked nucleic acid), ENA (registered trademark, 2'-O, 4'-C-Ethylene-bridged nucleic acids), GNA (glycerol nucleic acid), TNA (threose nucleic acid), or PNA (peptide nucleic acid).

Note that the polynucleotide of the present invention can be chemically synthesized by using a commercially-available automated nucleotide synthesizer or the like.

Moreover, as the polynucleotide used in the test of the present invention, a polynucleotide bound to a labeling substance can be used. The labeling substance is not particularly limited, as long as the labeling substance can bind to the polynucleotide and can be detected by a chemical or optical method. Examples of the labeling substance include fluorescent dyes (such as DEAC, FITC, R6G, TexRed, Cy5), dyes (chromogens) such as DAB other than the fluorescent dyes, enzymes, and radioactive substances.

The testing composition of the present invention may comprise other pharmacologically acceptable ingredients than the above-described polynucleotide. Examples of such other ingredients include buffers, emulsifiers, suspensions, stabilizers, antiseptics, physiological salts, and the like.

Further, besides composition, a preparation such as a substrate necessary for detection of the labeling substance added to the polynucleotide, a positive control or a negative control, or a buffer solution used to dilute or wash a sample can be combined, and a tube or a plate used for the reaction between the sample and the polynucleotide of the present invention, or the like can be combined, so that a kit for testing a disease attributable to Th1 cells can also be provided. Furthermore, the kit for testing a disease attributable to Th1 cells may comprise an instruction for the kit.

Further, the testing composition of the present invention can also be combined with a device for detecting the nucleotide sequence specific to the bacterium capable of inducing Th1 cell proliferation or activation in an intestine. Examples of the device include PCR systems, sequencers, and microarrays.

Additionally, the present invention also provides a method for testing a disease attributable to Th1 cells by using the above-described antibody, polynucleotide, or testing composition. To be more specific, the present invention provides a method for testing a disease attributable to Th1 cells, the method comprising the steps of:
  bringing the antibody, polynucleotide, or testing composition into contact with a sample isolated from a subject; and
  detecting the presence or absence of the bacterium capable of inducing Th1 cell proliferation or activation in an intestine, as a result of the contact.

The subject is not particularly limited, and includes animals, such as human, which may have a disease attributable to Th1 cells. Moreover, the sample isolated from such a subject is not particularly limited, either, and a fecal sample of the subject, a culture thereof, a polypeptide, a polynucleotide, a carbohydrate, or a lipid extracted therefrom, or the like is suitably used in the method of the present invention.

Examples of the method for detecting the presence or absence of the bacterium capable of inducing Th1 cell proliferation or activation in an intestine by bringing the antibody of the present invention or the testing composition comprising the antibody into contact with the sample include detection using an antibody (immunological methods) such as ELISA methods, immunoblotting, antibody array analyses, immunohistochemical staining, flow cytometry, imaging cytometry, radioimmunoassay, and immunoprecipitation.

Meanwhile, as the method for detecting the presence or absence of the bacterium capable of inducing Th1 cell proliferation or activation in an intestine by bringing the polynucleotide of the present invention or the testing composition comprising the polynucleotide into contact with the sample, it is possible to employ, for example, PCR (RT-PCR, real-time PCR, quantitative PCR), DNA microarray analysis, northern blotting, a new generation sequencing method (sequencing-by-synthesis, for example, sequencing using Solexa genome analyzer or Hiseq (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SoliD (registered trademark) or 5500x1 manufactured by Life Technologies Corporation), bead array method, in situ hybridization, dot blot, RNase protection assay, mass spectrometry, genomic PCR, or Southern blotting.

In the present invention, "testing" a disease attributable to Th1 cells includes testing not only whether the disease has developed or not, but also the risk of the development. If the presence of the bacterium capable of inducing Th1 cell proliferation or activation in an intestine is detected by the above-described method, it can be determined that a disease attributable to Th1 cells has developed or that the risk of the development is high.

A disease attributable to Th1 cells in a subject is normally diagnosed by a doctor (including one instructed by the doctor). The data obtained by the method of the present invention are useful in the diagnosis by a doctor. Thus, the method of the present invention can also be described as a method for collecting and presenting data useful in a diagnosis by a doctor.

Additionally, the present invention can also provide a companion diagnostic method utilizing the above-described test method and a drug used in the companion diagnostic method. Accordingly, the present invention also provides the following.

A method for determining effectiveness of a substance having an antibacterial activity against the bacterium capable of inducing Th1 cell proliferation or activation in an intestine in treating, alleviating, or preventing a disease attributable to Th1 cells, the method comprising the steps of:
  bringing the antibody, polynucleotide, or testing composition into contact with a sample isolated from a subject;
  detecting the presence or absence of the bacterium capable of inducing Th1 cell proliferation or activation in an intestine, as a result of the contact; and
  determining that the effectiveness of the substance in treating, alleviating, or preventing the disease is high for the subject, if the presence of the bacterium is detected in the previous step.

A method for treating, alleviating, or preventing a disease attributable to Th1 cells, the method comprising the step of providing a substance having an antibacterial activity against the bacterium capable of inducing Th1 cell proliferation or activation in an intestine to a patient for whom the effectiveness of the substance has been determined to be high according to the above-described determination method.

A composition for treating, alleviating, or preventing a disease attributable to Th1 cells, the composition comprising, as an active ingredient, a substance having an antibacterial activity against the bacterium capable of inducing Th1 cell proliferation or activation in an intestine, wherein the composition is provided to a subject for whom/which the effectiveness has been determined to be high according to the above-described determination method.

EXAMPLES

Hereinafter, the present invention will be described more specifically based on Examples. However, the present invention is not limited to the following Examples. In addition, Examples of the present invention were carried out using materials and methods described below.

<Mice>

C57BL/6 mice, BALB/c mice, and IQI mice maintained under SPF or GF conditions were purchased from Sankyo Labo Service Corporation, Inc. (Japan), Japan SLC, Inc. (Japan), or CLEA Japan, Inc. (Japan).

Note that "SPF" and "GF" respectively denote specific pathogen free and germ-free conditions.

GF mice and gnotobiotic group (gnotobiotic) mice were raised and maintained within the gnotobiotic facility of Keio University School of Medicine or RIKEN Center for Integrative Medical Sciences (IMS).

Il10$^{-/-}$ mice and Ifngr1$^{-/-}$ mice were purchased from the Jackson Laboratories. Myd88$^{-/-}$ mice, Tlr4$^{-/-}$ mice, and Myd88$^{-/-}$Trif$^{-/-}$ mice were purchased from Oriental Bio Service, Inc. (Japan).

All the animal experiments were approved by the Animal Experiments Committees of Keio University and RIKEN Yokohama Institute.

<16S rRNA Gene Pyrosequencing>

The feces from the mice were suspended in 20% glycerol/PBS containing 10 mM Tris HCl (pH 8.0) to a final concentration of 10% (w/v) and stored at −80° C. until the analysis.

When analyzed, each frozen sample was thawed, and 100 μL of the suspension was mixed with 900 μL of TE10 (10 mM Tris-HCl, 10 mM EDTA) buffer containing RNaseA (final concentration of 100 μg/mL, manufactured by Invitrogen) and lysozyme (final concentration of 3.0 mg/mL, manufactured by Sigma).

The resulting suspension was incubated at 37° C. for 1 hour with gentle mixing. Purified achromopeptidase (manufactured by Wako) was added to a final concentration of 2000 unit/mL, and the sample was further incubated at 37° C. for 30 minutes. Then, sodium dodecyl sulfate (final concentration of 1%) and a proteinase (final concentration of 1 mg/mL, manufactured by Nacalai) were added to the suspension, followed by incubation at 55° C. for 1 hour. Subsequently, high-molecular mass DNA was extracted with phenol-chloroform-isoamyl alcohol (25:24:1), precipitated with isopropanol, washed with 70% ethanol, and re-suspended in 200 μL of TE.

Next, to amplify the V1-V2 region of 16S rRNA, PCR was performed using ExTaq (manufactured by Takara) and the following primer set.

(1) The 454 primer A [5'-CCATCT-CATCCCTGCGTGTCTCCGACTCAG [SEQ ID NO: 7] (454 adaptor sequence)+barcode (10 bases)+AGRGTTTGATYMTGGCTCAG [SEQ ID NO: 8]-3' (27Fmod)], and (2) the 454 primer B [5'-CC-TATCCCCTGTGTGCCTTGGCAGTCTCAG [SEQ ID NO: 35] (454 adaptor sequence)+TGCTGCCTCCCGTAGGAGT [SEQ ID NO: 9]-3' (338R)].

Thereafter, amplicons (approximately 330 bp) obtained from each sample were purified using AMPure XP (manufactured by Beckman Coulter). DNA was quantified using a Quant-iT Picogreen dsDNA assay kit (manufactured by Invitrogen) and a TBS-380 Mini-Fluorometer (manufactured by Turner Biosystems).

Then, the amplified DNA was used as template for 454 GS Junior (manufactured by Roche) pyrosequencing using GS Junior Titanium emPCR kit-Lib-L, GS Junior Titanium Sequencing Kit, and GS Junior Titanium PicoTiterPlate Kit (all manufactured by Roche) according to the manufacturer's instructions.

Quality filter-passed reads were obtained by removing reads that did not have both primer sequences, had an average quality value of <25, and were possibly chimeric. Of the filter-passed reads, 3000 reads were used after trimming off of both primer sequences for each sample and subjected to OTU analysis with the cutoff similarity of 96% identity.

Representative sequences from each OUT were subjected to a BLAST search using a database from the Ribosomal Database Project (RDP) and a genome database constructed by the present inventors from publicly available genome sequences in NCBI and Human Microbiome Project.

<Preparation of Human Saliva Samples, Bacterial Culture, and Gnotobiotic Animals>

Human saliva samples were obtained at the Hospital of University of the Ryukyus according to the study protocol approved by the institutional review board as described in H. S. Said et al., DNA research: an international journal for rapid publication of reports on genes and genomes 21, 15-25 (2014). In addition, informed consent was obtained from each test subject.

Saliva samples from the following humans were selected as representative examples of each group (healthy, CD, and UC) on the basis of the principal coordinate analysis result of 16S rRNA sequences of saliva microbiotas.

CD #1 patient: IBD029, 50-year-old, Japanese man, IOIBD score 3 (active-phase)

CD #2 patient: IBD121, 52-year-old, Japanese man, IOIBD score 1 (remission-phase)

UC #1 patient: IBD096, 23-year-old, Japanese woman, UC-DAI mild

UC #2 patient: IBD118, 65-year-old, Japanese man, UC-DAI moderate

Healthy donor #1: S-AKO07, 37-year-old, Japanese man

Healthy donor #2: S-AKO17, 39-year-old, Japanese woman.

The saliva samples were suspended in equal volume (w/v) of PBS containing 20% glycerol/PBS. The samples were snap-frozen in liquid nitrogen and stored at −80° C. until use.

When used, the frozen stocks were thawed, centrifuged at 3300 g at 4° C. for 10 minutes, suspended in PBS, and then orally administered to GF mice (100 μL per mouse). To isolate Th1-inducing bacterial strains, cecal contents from GF+CD #2 and GF+UC #2 were serially diluted with PBS and seeded onto nonselective and selective agar plates. Then, after culturing under anaerobic conditions (80% $N_2$, 10% H2, 10% $CO_2$) in an anaerobic chamber (Coy Laboratory Products) at 37° C. for 2 or 4 days, individual colonies were picked.

The 16S rRNA gene region was amplified with the following universal primer set to determine the sequence. (27F: 5'-AGRGTTTGATYMTGGCTCAG-3' [SEQ ID NO: 8], 1492R: 5'-GGYTACCTTGTTACGACTT-3' [SEQ ID NO: 10]) The samples thus sequenced in the culture collection were grouped into "strains" if their 16S rRNA gene sequences had 100% identity.

The resulting strain sequences were compared to those in the RDP database and to OTUs detected from fecal samples of the GF+CD #2 and GF+UC #2 to determine closely related species or strains and corresponding OTUs.

To prepare the bacterial mixture solution, the bacterial strains were individually cultured to confluence and mixed at equal volumes of the media. Note that Kp-2H7 and Ec-2B1 were individually cultured in Schaedler broth; 2D5, Ve-2E1, 2G7, and 2E4 were individually cultured in PYG broth; Fu-21f and 2B11 were individually cultured in EGF broth.

The isolate mixture was orally administered to GF mice (200 µL of the medium containing approximately 1 to 2×10$^8$ CFU of the total bacteria was administered per mouse). Moreover, all the mice receiving the mixture were maintained in a single gnotobiotic isolator.

*K. pneumoniae* bacterial strains, BAA-2552, BAA-1705, 700721, 700603, and 13882 were purchased from American Type Culture Collection (Manassas, VA, USA).

*K. pneumoniae* KP-1 was isolated at the Scott A. Rice Laboratory (see K. W. Lee et al., The ISME journal 8, 894 (April 2014)).

KCTC2242 was obtained from the Korean Collection for Type Cultures (KCTC, Daejeon, Korea).

*K. pneumoniae* 34E1 was isolated from cecal contents of ampicillin-treated SPF mice in the laboratory of Kenya Honda, one of the present inventors.

The *K. pneumonia* strains were cultured at 37° C. in Schaedler broth, Luria Bertani (LB) broth or on LB agar plates.

For administration of heat-killed bacteria, Kp-2H7 was cultured overnight, washed with autoclaved water, and heat-killed at 105° C. for 30 minutes. The heat-killed cells were given to GF mice via drinking water (5×10$^7$ equivalent CFU/mL) for 3 weeks.

<Intratracheal Injection of *Klebsiella*>

SPF B6 mice were anesthetized with isoflurane and placed in supine position. Under anesthesia condition, each trachea was opened in midline by about 2 cm vertical incision, and either sterile PBS or *Klebsiella* suspension (1×10$^6$/10 µL) was injected into the trachea with a sterile 30-gauge needle. The mice were sacrificed 7 days after the bacterial inoculation. The lungs were collected for isolation of lymphocytes and histological examination.

<Isolation of Lymphocytes and Flow Cytometry>

Small and large intestines, lungs, and palates were collected. The intestines were opened longitudinally and washed with PBS to remove all the luminal contents. All the samples were incubated in 20 mL of Hanks' balanced salt solution (HBSS) containing 5 mM EDTA for 20 minutes in a shaking water bath set at 37° C. to remove epithelial cells.

After removal of remaining epithelial cells, muscular layers, and fat tissues using forceps, the samples were cut into small pieces and incubated in 10 mL of RPMI1640 containing 4% fetal bovine serum, 0.5 mg/mL collagenase D, 0.5 mg/ml dispase II, and 40 µg/mL DNaseI (all manufactured by Roche Diagnostics) for 45 minutes in a shaking water bath set at 37° C.

The digested tissues were washed with HBSS containing 5 mM EDTA, re-suspended in 5 mL of 40% Percoll (manufactured by GE Healthcare), and underlaid with 2.5 mL of 80% Percoll in a 15 mL Falcon tube. Then, Percoll gradient separation was performed by centrifugation at 850 g at 25° C. for 25 minutes. The lymphocytes were collected from the interface of the Percoll gradient, washed with RPMI1640 containing 10% FBS, and stimulated with 50 ng/ml PMA and 750 ng/ml ionomycin (both manufactured by Sigma) in the presence of Golgistop (registered trademark, manufactured by BD Biosciences) at 37° C. for 4 hours.

After the dead cells were labeled with Ghost Dye 780 (manufactured by Tonbo Biosciences), the cells were permeabilized and stained with an anti-CD3e antibody (BV605; manufactured by Biolegend), an anti-CD4 antibody (BV510; manufactured by Biolegend), an anti-CD8a antibody (PE/Cy7; manufactured by Biolegend), an anti-TCRβ antibody (BV421; manufactured by Biolegend), an anti-TCRgd antibody (PE; manufactured by Bioledgend), an anti-CD44 antibody (BV785; manufactured by Bioledgend), an anti-IFN-γ antibody (FITC or PE/Cy7; manufactured by Biolegend), an anti-IL-17A antibody (eFluor660; manufactured by eBioscience), an anti-T-Bet antibody (PE/Cy7; manufactured by Bioledgend), an anti-RORγt antibody (PE or APC; manufactured by eBioscience), and an anti-Foxp3 antibody (PerCPCy5.5; manufactured by eBioscience) using the Foxp3/Transcription Factor Staining Buffer Kit (manufactured by Tonbo Biosciences).

All the data were obtained with a BD LSRFortessa or FACSAria II (manufactured by BD Biosciences), and analyzed with Flowjo software (manufactured by TreeStar). Note that CD4$^+$ T cells were defined as a CD4$^+$TCRβ$^+$ CD3e$^+$ subset within the live lymphocyte gate.

<Scanning Electron Microscopy>

Intestines were washed with PBS, fixed with 50 mM phosphate buffer (pH 7.2) containing 2.5% glutaraldehyde, and post-fixed with 50 mM phosphate buffer (pH 7.2) containing 1% osmium tetroxide. The samples were dehydrated in an ethanol series and substituted with isoamyl acetate. After the dehydration, the sample was put in a critical point dryer (CPD 030; Leica Microsystems), coated with platinum, and observed using a scanning electron microscope (SU-1510; Hitachi High-Technologies) at 5 or 10 kV. For all the scanning microscopy analyses, at least 10 areas were examined per animal. Note that each group consisted of 3 to 5 animals.

<Transmission Electron Microscopy>

To visualize the bacterial structure, metal contact freezing and freeze substitution were used. The freezing device used was type VFZ-101 (manufactured by Vacuum Device, Ibaraki, Japan) with liquid nitrogen as the cryogen. The freeze substitution was carried out in acetone containing 2% OsO$_4$ at −80° C. for 120 hours, and the temperature was gradually brought back to room temperature (the temperature was increased from −80° C. to −55° C. over 12.5 hours, and then held at −55° C. for 8 hours. After increased from −55° C. to −25° C. over 10 hours, the temperature was held at −25° C. for 8 hours. Subsequently, the temperature was increased from −25° C. to 0° C. over 5 hours).

The bacterial cells were embedded in a low-viscosity epoxy resin (Nisshin EM), and ultra-thin sections were prepared using an ultramicrotome (EM-UC7; Leica Microsystems)

The sections were stained with a 4% aqueous solution of uranyl acetate for 12 minutes and with Reynolds' lead citrate solution (see E. S. Reynolds, The Journal of cell biology 17, 208 (April 1963)) for 1 minute. Then, the sections were observed using a transmission electron microscope (JEM-1400; Jeol, Tokyo, Japan) at 80 kV.

For negative staining electron microscope observation, the bacteria were cultured on an agar plate and fixed with 1% ammonium acetate containing 2.5% glutaraldehyde. Samples were placed on a Formvar-coated pre-hydrophilized copper grid (200 mesh), and the grid was immediately touched to filter paper by the edge to remove excess sample. The sample was stained with phosphotungstic acid (pH 7.0) for 10 to 20 seconds, blotted to dry, and observed with JEM-1400.

<Bacterial Colonization of Antibiotic-Treated Mice>

Prior to bacterial gavage, the following antibiotics were administered to SPF mice (WT B6, Il10$^{-/-}$ or Ifngr1$^{-/-}$) through the drinking water for 4 days. Moreover, mice without these antibiotics administered were also prepared.

Antibiotics: ampicillin (200 mg/L), tylosin (500 mg/L), metronidazole (500 mg/L), spectinomycin (200 mg/L), vancomycin (200 mg/L).

Kp-2H7 or Ka-11E12 was cultured to log phase in LB broth, and 1 to $2\times10^8$ CFUs were used to inoculate the mice.

Feces were collected 1, 3, 7, 14, and 21 days after the bacterial gavage. Then, DNA was extracted therefrom for 16S rRNA gene pyrosequencing. The bacterial colonization was confirmed by qPCR using the following primers specific to each strain.

Klebsiella (ompK36-3_F: 5'-GCGACCAGACCTA-CATGCGT-3' [SEQ ID NO: 11], ompK36-3_R: 5'-AGTCGAAAGAGCCCGCGTC-3' [SEQ ID NO: 12]), Kp-2H7 (sca4_298_F: 5'-AGCACTAGCGGCTGTGGTAT-3' [SEQ ID NO: 13], sca4_298_R: 5'-ACTTACTCGGGCCCTTGATT-3' [SEQ ID NO: 14]), Ka-11E12 (group_4037_F: 5'-CTTCGCCTT-CATCAGCTTCA-3' [SEQ ID NO: 15], group_4037_R: 5'-TCATCATTAACGCGGGTCAG-3' [SEQ ID NO: 16]).

At the end of the experiment, the colon tissues were collected and examined for Th1 cell frequency.

<Preparation of Colonic ECs and DCs>

The colon tissues were collected, cut open longitudinally, and washed well with ice-cold PBS. Epithelial cells (ECs) were scraped using a glass slide, immediately frozen in liquid nitrogen, and stored at −80° C. until the analysis.

The residual tissues were incubated with HBSS containing 5 mM EDTA at 37° C. for 20 minutes with shaking to completely remove ECs. Then, the tissues were cut into small pieces and incubated with RPMI1640 containing 4% fetal bovine serum, 0.5 mg/mL collagenase D, 0.5 mg/mL dispase II, and 40 µg/mL DNaseI for 45 minutes at 37° C. in a shaking water bath.

CD11 positive cells were stained with an anti-CD11c antibody (APC; manufactured by Biolegend) and enriched by MACS using anti-APC beads (manufactured by Miltenyi Biotec). Positively selected cells were further sorted on FACSAriaII, with a resulting purity of around 97%.

<RNA-Seq and qPCR Analysis>

Total RNA was isolated from the colonic ECs and DCs using TRIzol reagent (manufactured by Invitrogen) according to instructions thereof.

For real-time qPCR, cDNA was synthesized using Rever-Tra Ace (registered trademark) qPCR RT Master Mix (manufactured by TOYOBO). qPCR was performed using Thunderbird (registered trademark) SYBR qPCR Mix (manufactured by TOYOBO) on a LightCycler 480 (Roche). The following primers were used:

Gapdh, 5'-CTCATGACCACAGTCCATGC-3' [SEQ ID NO: 17] and 5'-CACATTGGGGGTAGGAACAC-3' [SEQ ID NO: 18];

Gbp2, 5'-TGCTGGATCTTTGCTTTGGC-3' [SEQ ID NO: 19] and 5'-AGTTAGCTCCGTCACATAGTGC-3' [SEQ ID NO: 20];

Gbp6, 5'-AATGCCTTGAAGCTGATCCC-3' [SEQ ID NO: 21] and 5'-GTTCTTTGTCATGCGTTGGC-3' [SEQ ID NO: 22];

Ifi47, 5'-GGCTCATTGCTTCAGACTTTCC-3' [SEQ ID NO: 23] and 5'-ACTGATCCATGGCAGTTACCAG-3' [SEQ ID NO: 24];

Cxc19, 5'-ATCATCTTCCTGGAGCAGTGTG-3' [SEQ ID NO: 25] and 5'-TTGTTGCAATTGGGGCTTGG-3' [SEQ ID NO: 26];

H2-Ab1, 5'-TTGGCCTTTTCATCCGTCAC-3' [SEQ ID NO: 27] and 5'-ATTCGGAGCAGAGACATTCAGG-3' [SEQ ID NO: 28];

H2-DMb1, 5'-TCTCCAGCGTTTGCAAAACG-3' [SEQ ID NO: 29] and 5'-AAAGGTGTGGTTTGGGCTAC-3' [SEQ ID NO: 30];

Ifi208, 5'-AGAACTTGCAGCTCGTGTTG-3' [SEQ ID NO: 31] and 5'-TGGTTCTACTTCCCAAGCTTCC-3' [SEQ ID NO: 32]; and Ifng, 5'-ACGGCACAGTCATTGAAAGC-3' [SEQ ID NO: 33] and 5'-ACCATCCTTTTGCCAGTTCC-3' [SEQ ID NO: 34].

For RNA-seq, RNA library was prepared using a NEB-Next Ultra RNA Library Preparation Kit for Illumina (manufactured by New England Biolabs) according to the manufacturer's instructions.

For assessing the library quality, sequencing was carried out on a HiSeq 1500 system (manufactured by Illumina) using single-ended 50-bp reads.

The sequenced reads were mapped to the mouse reference genome (mm9, NCBI build 37) and normalized to fragments per kbp per million reads (FPKM) values using the Tophat & Cufflinks software pipeline.

Figure 25:
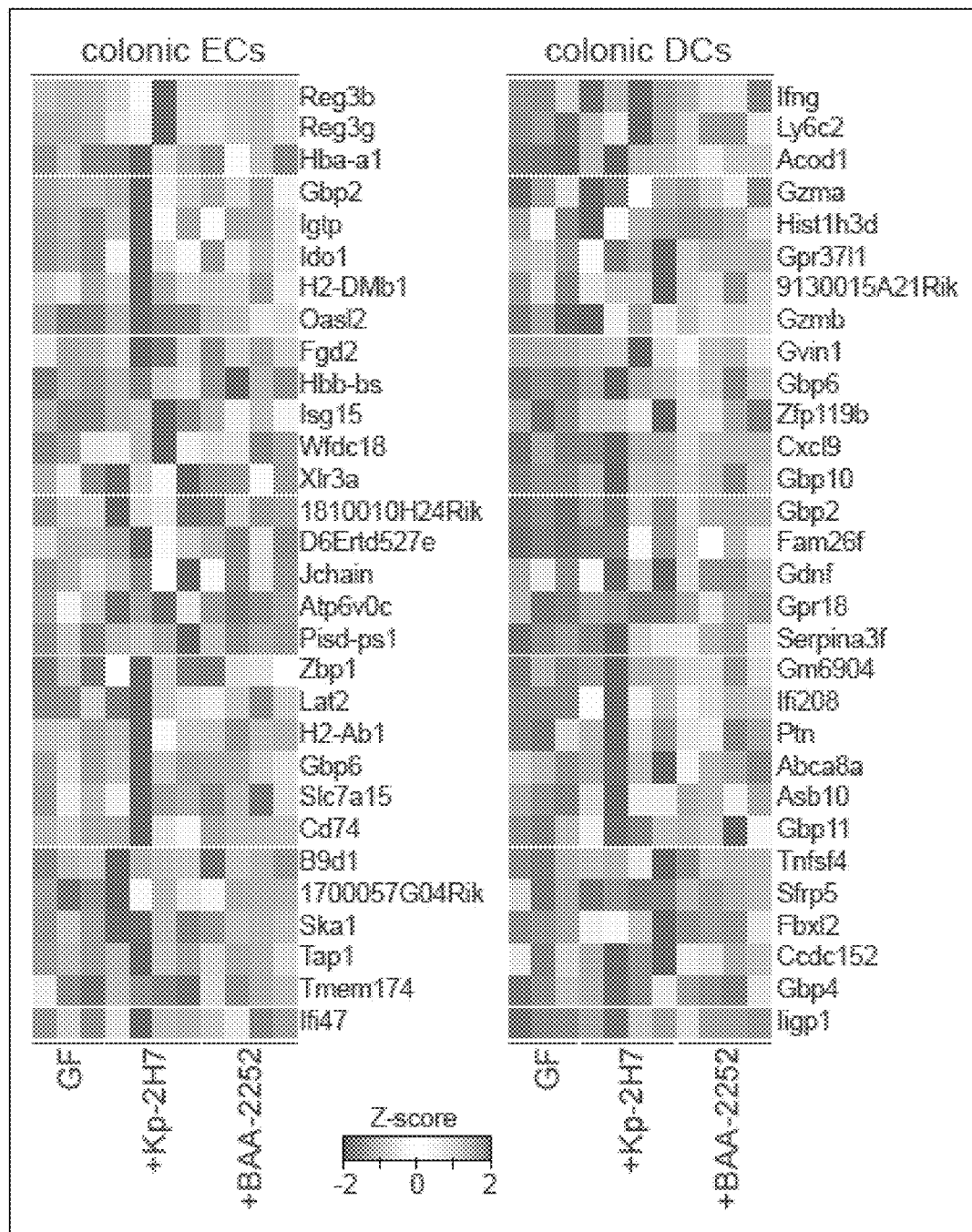
FIG. 25 is a heatmap showing differential gene expressions in colonic epithelial cells (ECs) and dendritic cells (DCs) from wildtype mice monocolonized with Kp-2H7 or BAA-2552 for 1 week. In the figure, the heatmap colors represent z-scores normalized to FPKM values for each gene.

The heatmap in FIG. 25 shows the relative abundance (Z-score) of genes that were upregulated (>2-fold, FPKM value of 0.1 or more) in Kp-2H7-monocolonized mice in comparison with GF mice and BAA2552-monocolonized with mice.

Figure 27:
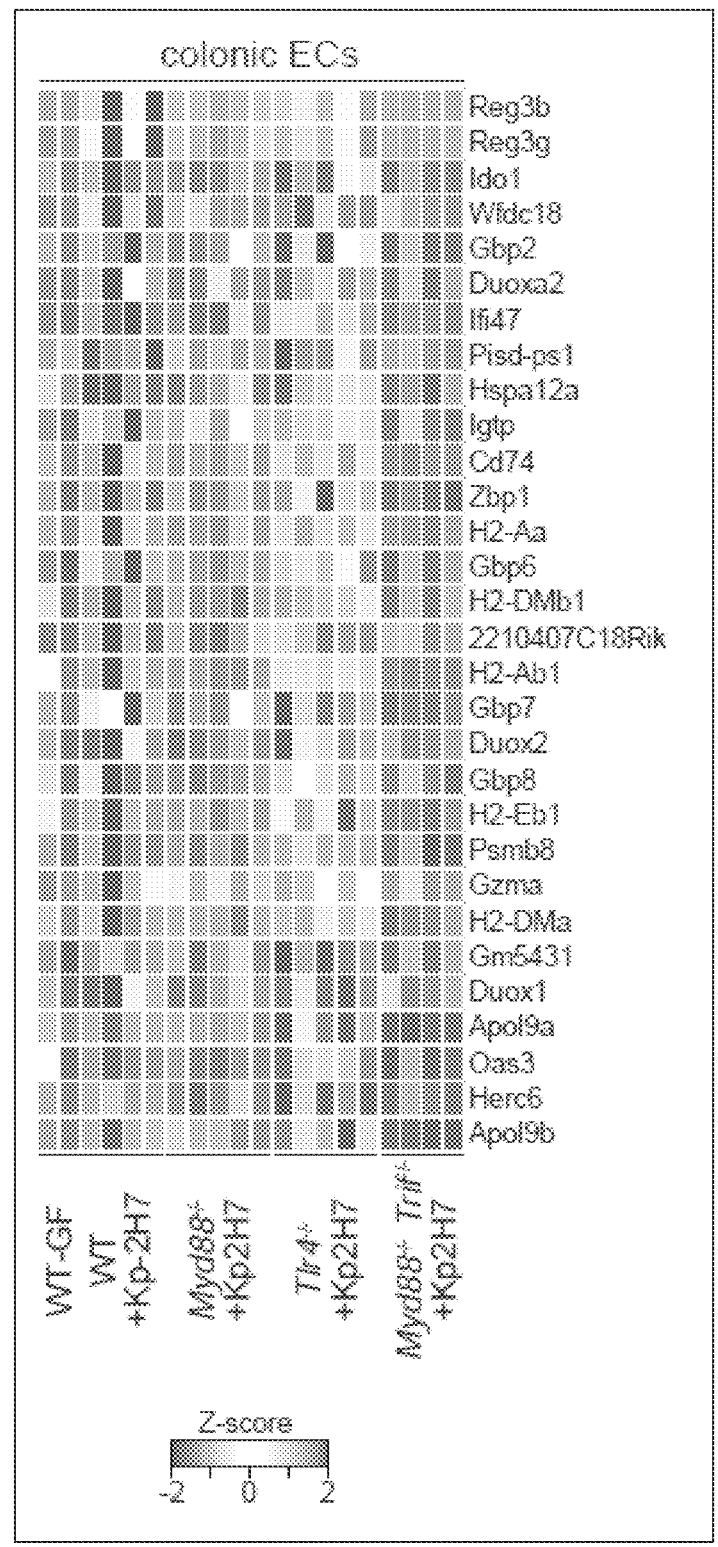
FIG. 27 is a heatmap showing differential gene expressions in colonic epithelial cells from WT mice, Myd88$^{-/-}$ mice, Tlr4$^{-/-}$ mice, and Myd88$^{-/-}$Trif$^{-/-}$ mice monocolonized with Kp-2H7 for 3 weeks. In the figure, heatmap colors represent z-scores normalized to FPKM values for each gene.

The heatmap in FIG. 27 shows the relative abundance (Z-score) of genes that were commonly upregulated (>2-fold, FPKM value of 0.1 or more) in Kp-2H7-monocolonized mice in comparison with Kp-2H7-monocolonized Myd88$^{-/-}$ mice.

Figure 26:
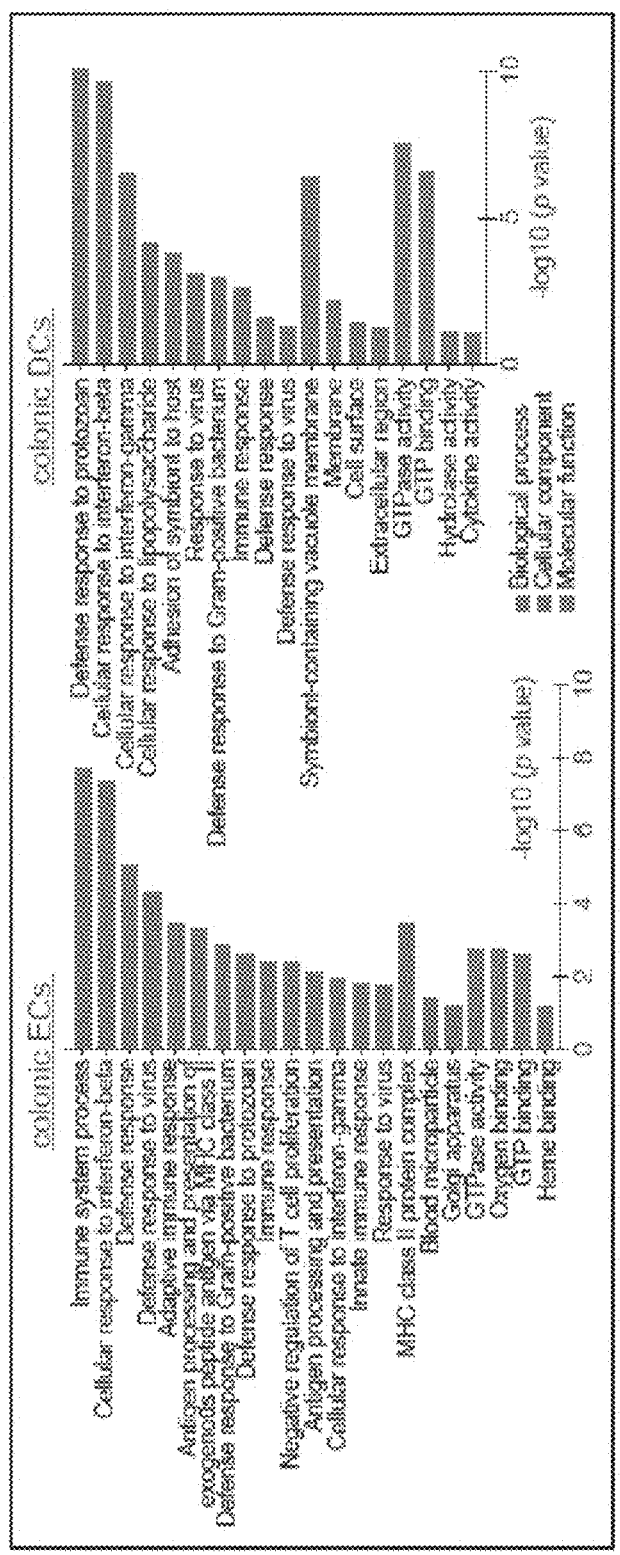
FIG. 26 shows graphs for illustrating terms defined by gene ontology (GO) which were significantly enriched in the gene set upregulated in the colonic epithelial cells and dendritic cells of the wildtype mice monocolonized with Kp-2H7 for 1 week.
Figure 28:
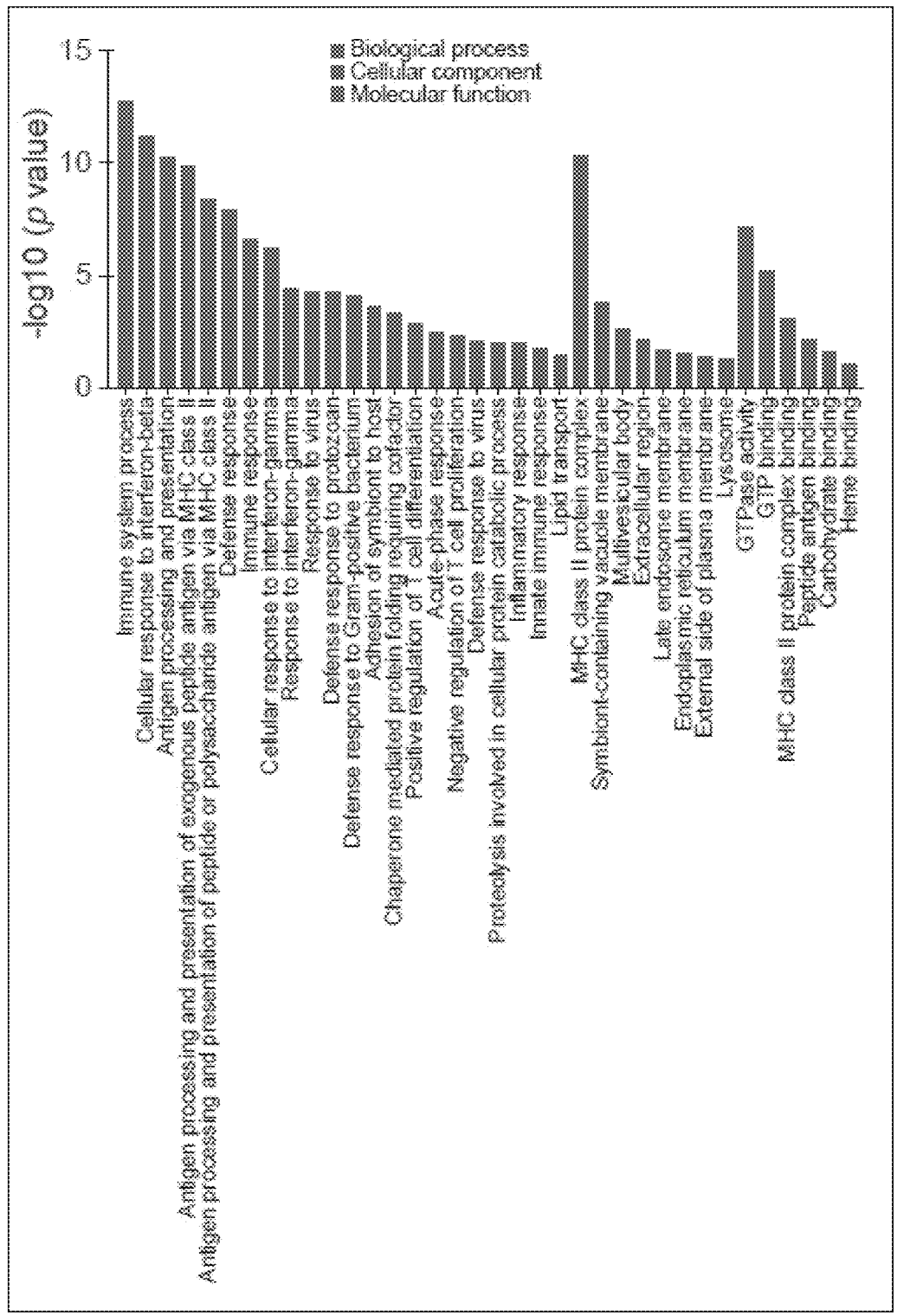
FIG. 28 is a graph for illustrating terms defined by gene ontology (GO) which were significantly enriched in the gene set upregulated in the colonic epithelial cells and dendritic cells of the wildtype mice monocolonized with Kp-2H7 for 3 weeks.

The upregulated genes (genes shown in the left of FIG. 26, genes shown in the right of FIG. 26, or genes shown in FIG. 28) were subjected to gene ontology enrichment analysis using the DAVID Bioinformatics Resources 6.8 (W. Huang da et al., Nature protocols 4, 44 (2009)).

<Histological Analysis>

For fluorescence in situ hybridization (FISH) of Kp-2H7 and Ka-11E12 as the targets, colon tissues were fixed with a methanol-Carnoy's solution and embedded in paraffin. The sections were treated with 0.1 M HCl, hybridized with the 5' Alexa488-labeled EUB338 (5'-GCTGCCTCCCGTAG-GAGT-3') probe, and stained with rhodamine labeled Ulex Europaeus Agglutinin I (UEA1, manufactured by Vector Laboratories). All the sections were counterstained with DAPI, mounted on Fluoromount/Plus (manufactured by Diagnostic BioSystems), and visualized using a TCS SP5 confocal microscope manufactured by Leica Camera AG.

To evaluate the development and severity of colitis and pneumonia, mice were sacrificed 5 weeks after oral inoculation or 7 days after intratracheal injection. Colons and lungs were fixed with 4% paraformaldehyde, embedded in paraffin, and stained with hematoxylin and eosin.

The degree of colitis was graded based on the following criteria:

inflammatory cell infiltration (score: 0 to 4),
mucosa thickening (score: 0 to 4),
goblet cell depletion (score: 0 to 4),
crypt abscess (score: 0 to 4), and
Destruction of architecture (score: 0 to 4).

The final histological score was determined as the sum of the scores of these parameters.

The pneumonia score was determined as the sum of the scores of the following two sections:

alveoli (no change: 0, edema: 1, detecting inflammatory cells in alveolar lumina: 2, inflammatory destruction of alveoli with lung abscess), and bronchioles (no change: 0, mild inflammation in the wall: 1, severe inflammation in the wall with luminal slough: 2, severe inflammation with luminal slough and peribronchial inflammation: 3).

<Bacterial Genome Sequencing>

The genomes of *Klebsiella* strains were extracted by a similar method to the method described above in 16S rRNA Gene Pyrosequencing. Then, the genome sequences were determined by the whole-genome shotgun sequencing using PacBio RSII and Illumina MiSeq sequencers.

The genomic DNA was sheared to obtain DNA fragments. Template DNA was prepared according to each supplier's protocol. The obtained RSII reads were subjected to de novo-assembly using HGAP3. MiSeq reads (2×300 nt) were mapped onto the RSII assembled contigs to correct the sequences of low quality regions.

To evaluate the phylogeny of the isolated strains, 54 complete genomes and 15 draft genomes were downloaded from NCBI. These genomes include 59 *K. pneumoniae* strains, three *K. variicola* strains, one *K. michiganensis* strain, three *K. oxytoca* strains, one *K. quasipneumoniae* strain, and two *K. aeromobilis* (*E. aerogenes*) stains. Moreover, phylogenetic trees were constructed based on the Mash distance (see B. D. Ondov et al., Genome biology 17, 132 (Jun. 20, 2016)) using neighbor-joining method.

<MLST, wzi and wzc Sequence Typing>

The genome sequence of each strain was aligned against MLST database (http://bigsdb.pasteur.fr/klebsiella/klebsiella.html). Then, sequence-based capsular (K) typing was carried out based on sequencing of wzi or wzc genes.

<Bacterial Motility Assay>

Bacterial motility assay was performed using semi-solid LB medium containing 0.25% in a 14-mL tube. Bacteria cultured in LB broth media were each inoculated into a semi-solid LB medium using a straight wire by making a single stab down the center of the tube to half the depth of the medium. After the incubation at 37° C. for 24 hours, bacteria which showed diffuse and hazy spread throughout the medium were determined as motile bacteria. The bacterial flagella were detected using HEK-Blue mTLR5 cells (manufactured by InvivoGen), following the manufacturer's protocol.

<Statistical Analysis>

All the statistical analyses were performed using GraphPad Prism software (GraphPad Software, Inc.) or JMP software v.12 (SAS Institute, Inc.) with two-tailed unpaired Student's t-test (parametric), Wilcoxon rank-sum test (non-parametric), and one-way analysis of variance (ANOVA) followed by Tukey's post hoc test (3 or more groups, parametric).

Using the above-described materials and methods, first, efforts were made to identify oral bacteria which caused a strong immunostimulation upon intestinal colonization and consequently induced Crohn's disease or the like, using gnotobiotes (gnotobiotic group).

Example 1

The present inventors prepared gnotobiotic mice by orally gavaging saliva samples of two Crohn's disease (CD) patients into C57BL/6 (B6) germ-free (GF) mice. Then, the mice in each group were raised in a gnotobiotic isolator for 6 weeks to examine small intestinal and colonic lamina propria (LP) immune cells.

Figure 2:
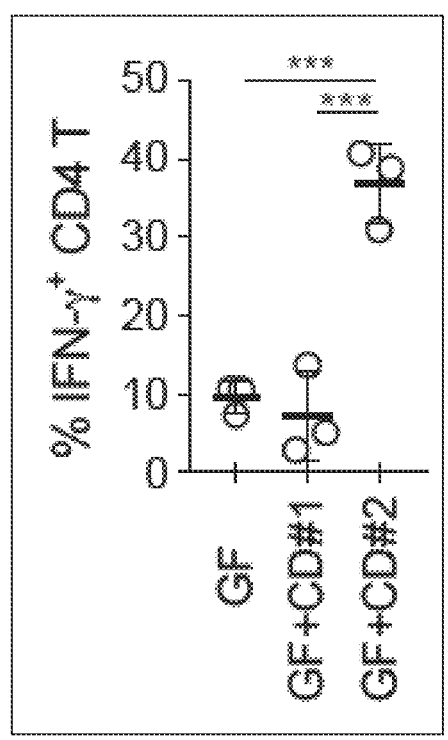
FIG. 2 is a graph for illustrating the result of the flow cytometry analysis of the frequencies of the IFN-γ positive cells among the CD4⁺TCRβ⁺ T cells in the colonic LP of the exGF B6 mice inoculated with the saliva samples from the two Crohn's disease patients (CD #1, CD #2), respectively. In the graph, each point represents data on an individual mouse. In addition, "GF" indicates data on the group inoculated with no saliva sample. Error bars indicate means±standard deviations. *** indicates $P<0.001$ (based on one-way analysis of variance (ANOVA) followed by Tukey's post hoc test).

As a result, as shown in FIGS. 1 and 2, no significant change in the intestinal T cells was found in the mice (GF+CD #1 mice) receiving the saliva of the CD patient #1. In contrast, a marked accumulation of interferon-γ (IFN-g)$^+$ CD4$^+$ T cells (Th1 cells) was found in the colonic lamina propria of the mice (GF+CD #2 mice) receiving the saliva of the CD patient #2.

Hence, the community compositions were compared by the 16S rRNA sequencing among the saliva microbiotas of the GF mice before the administration and the fecal microbiotas of the animals (exGF mice) colonized with the saliva microbiotas.

Figure 3:
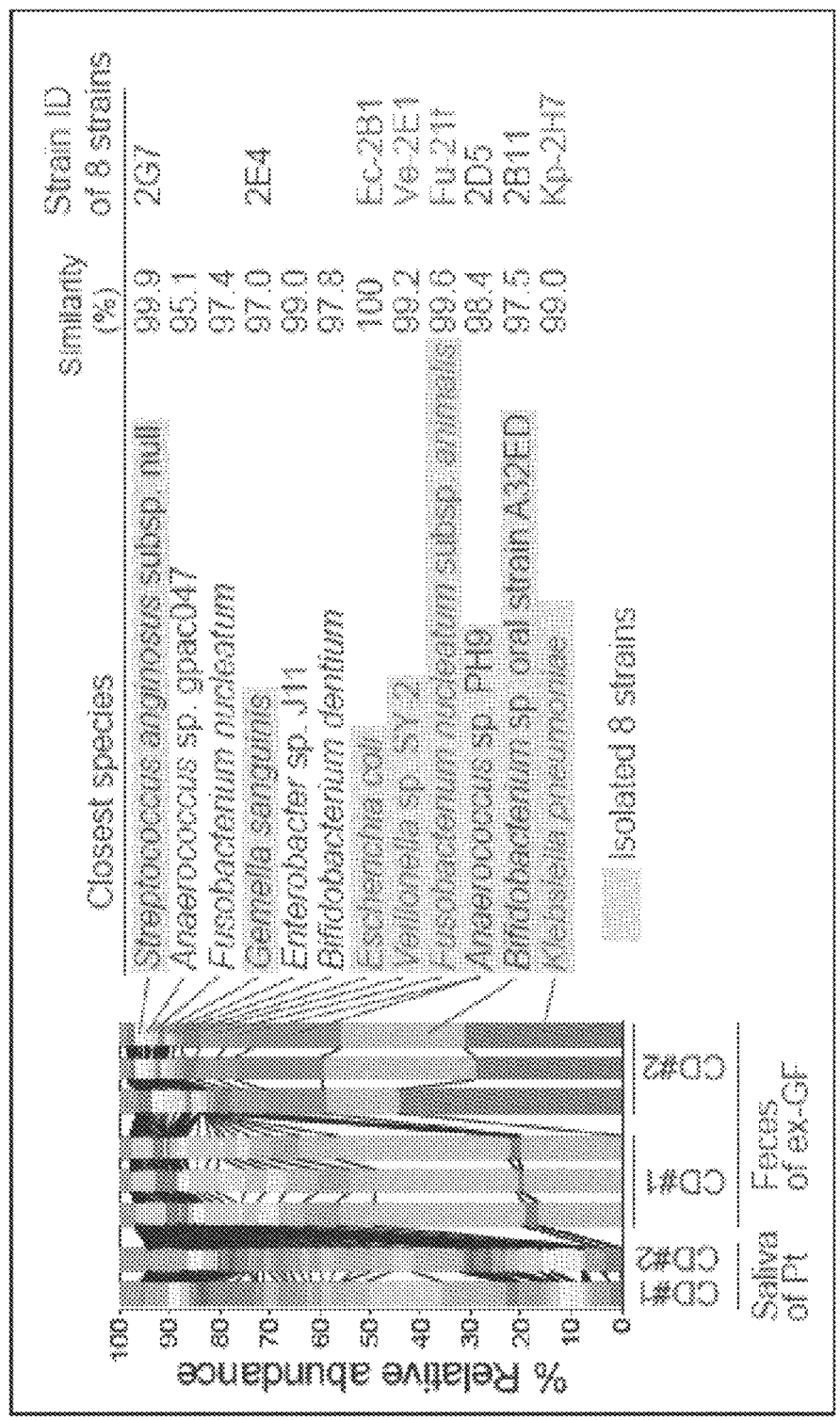
FIG. 3 is a schematic diagram for illustrating the result of pyrosequencing analysis of 16S rRNAs of saliva microbiotas of the patients (CD #1, CD #2) and fecal microbiotas of exGF mice inoculated with the saliva microbiotas, respectively. Note that each group was analyzed with n=3, and quality filter-passed sequences were classified into OTUs based on sequence similarity (96% identity). The diagram shows the relative abundance of the OTUs and known bacterial species closely related to each OTU. In addition, eight isolated bacterial strains corresponding to the OTUs are marked in green.

As a result, although the saliva samples of the two patients contained similar microbial communities, a marked difference was found between the fecal microbiotas of the GF+CD #2 mice and the GF+CD #1 mice as shown in FIG. 3. Importantly, most of the bacterial species observed in the fecal microbiota of the exGF mice were minor bacterial species present in the saliva microbiota.

These results revealed that even minor bacterial species present in the oral microbiota were capable of colonizing the digestive tract, and further that such a limited subset was capable of inducing the accumulation of intestinal Th1 cells.

Next, to isolate Th1 cells inducing bacteria, cecal contents of the GF+CD #2 mice were cultured using various media under anaerobic conditions. Then, 24 colonies having different appearances were picked.

The result of sequencing the 16S rRNA genes revealed that these colonies included the following eight strains, which consisted of diverse genera, and accounted for major bacterial species in the gut microbiota colonizing the GF+CD #2 mice.

*Gemella, Bifidobacterium, Streptococcus, Escherichia, Fusobacterium, Veillonella, Anaerococcus*, and *Klebsiella*.

To examine whether these isolated bacterial strains had the Th1 cell-inducing capability, these eight strains were all cultured, and a mixture thereof (8-mix) was administered to GF mice. Then, as a result of the magnitude comparison with the result observed in the GF+CD #2 mice, efficient induction of Th1 cells was found in the intestinal LP of the mice inoculated with 8-mix as shown in FIGS. 1, 2, and 4.

Since *Fusobacterium* (Fu) and *Veillonella* (Ve) have been known to be involved in IBD pathogenesis (see NPL 2), next, mice colonized with the two strains were prepared. However, as shown in FIG. 4, only a few Th1 cells were found in the mice colonized with these bacterial strains.

Next, a *Klebsiella pneumoniae* strain ID 2H7 (Kp-2H7) was tested, which exhibited the most prominent component percentage in the microbiota of the GF+CD #2 mice.

Figure 4:
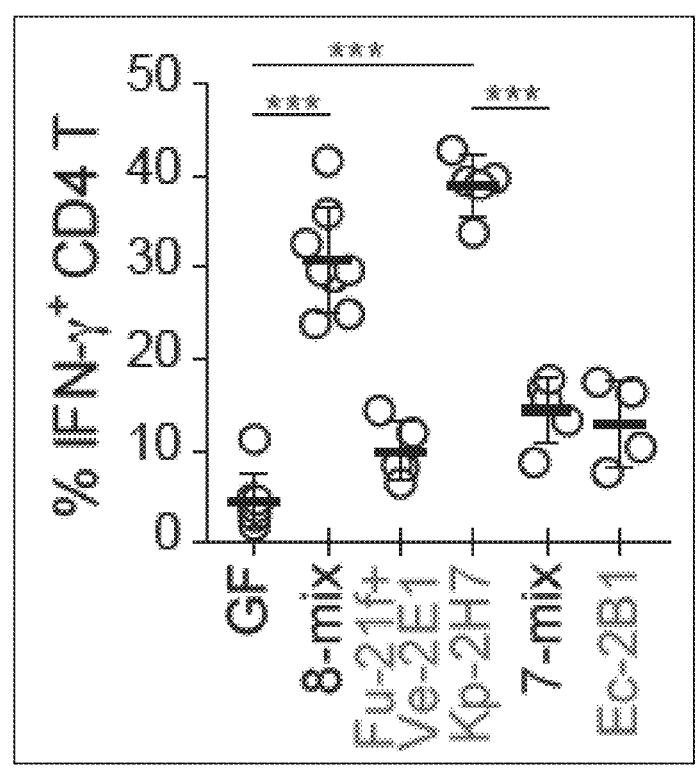
FIG. 4 is a graph showing the percentage of Th1 cells in the colonic LP of exGF B6 mice colonized with a mixture of the eight strains (8-mix), an Fu-21f+Ve-2E1 mixture, Kp-2H7, a mixture of seven strains (7-mix), or Ec-2B1. Note that, in the graph, "GF" indicates data on a group inoculated with no bacterium. Error bars indicate means±standard deviations. *** indicates $P<0.001$ (based on one-way analysis of variance (ANOVA) followed by Tukey's post hoc test).

As a result, as shown in FIG. 4, although mixing and administering seven strains (7-mix) other than Kp-2H7 did not induce Th1 cells, Th1 cells were markedly induced as a result of orally administering Kp-2H7 alone. This result revealed that the Kp-2H7 strain was a bacterial strain which mainly contributed to the accumulation of Th1 cells observed in the GF+CD #2 mice.

Figure 5:
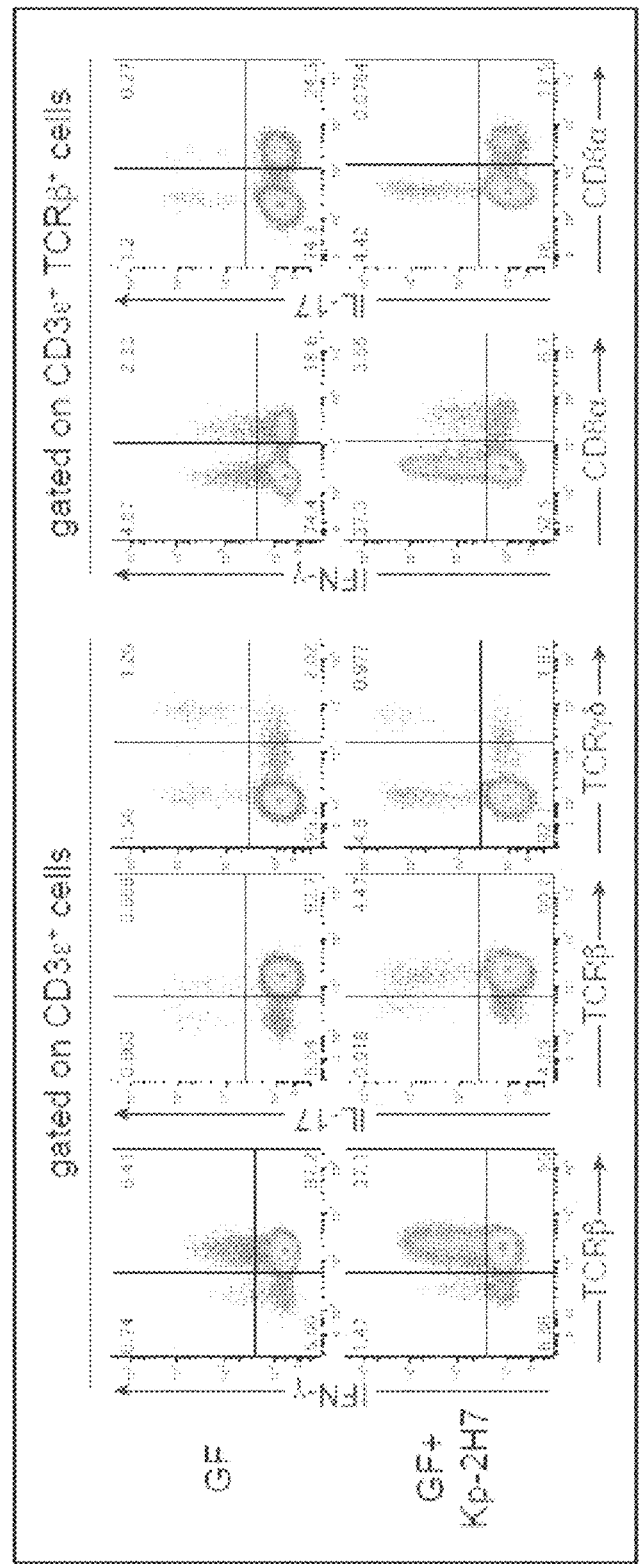
FIG. 5 shows plots for illustrating representative results of flow cytometry analysis of the expressions of IFN-γ, IL-17A, TCRβ, TCRγδ, and CD8α in colonic LP CD3ε⁺ cells or CD3ε⁺TCRβ+ cells isolated from the GF mice or the Kp-2H7-monocolonized GF mice (GF+Kp-2H7).
Figure 6:
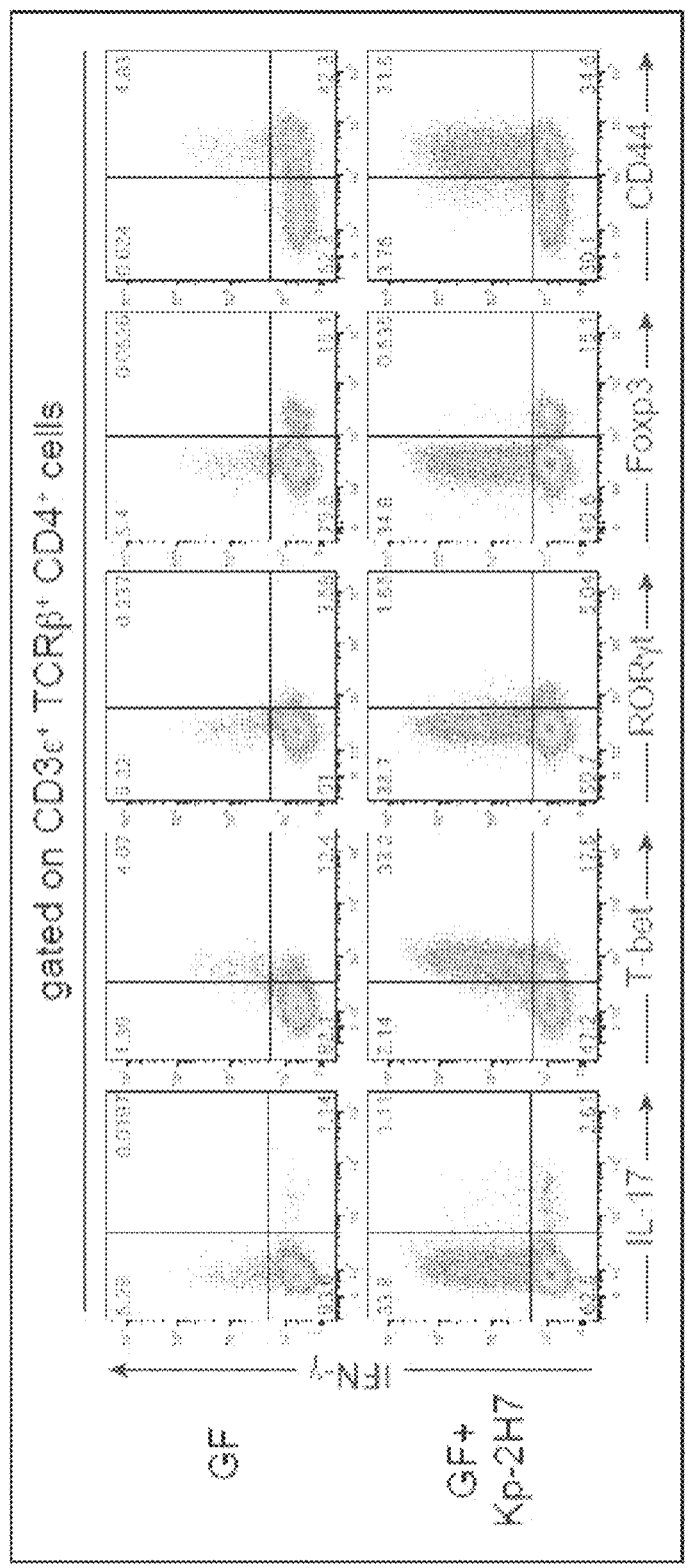
FIG. 6 shows plots for illustrating representative results of flow cytometry analysis of the expressions of IFN-γ, IL-17, T-bet, RORγt, Foxp3, and CD44 in colonic CD3ε⁺TCRβ⁺CD4⁺ cells isolated from the GF mice or the GF+Kp-2H7 mice.
Figure 7:
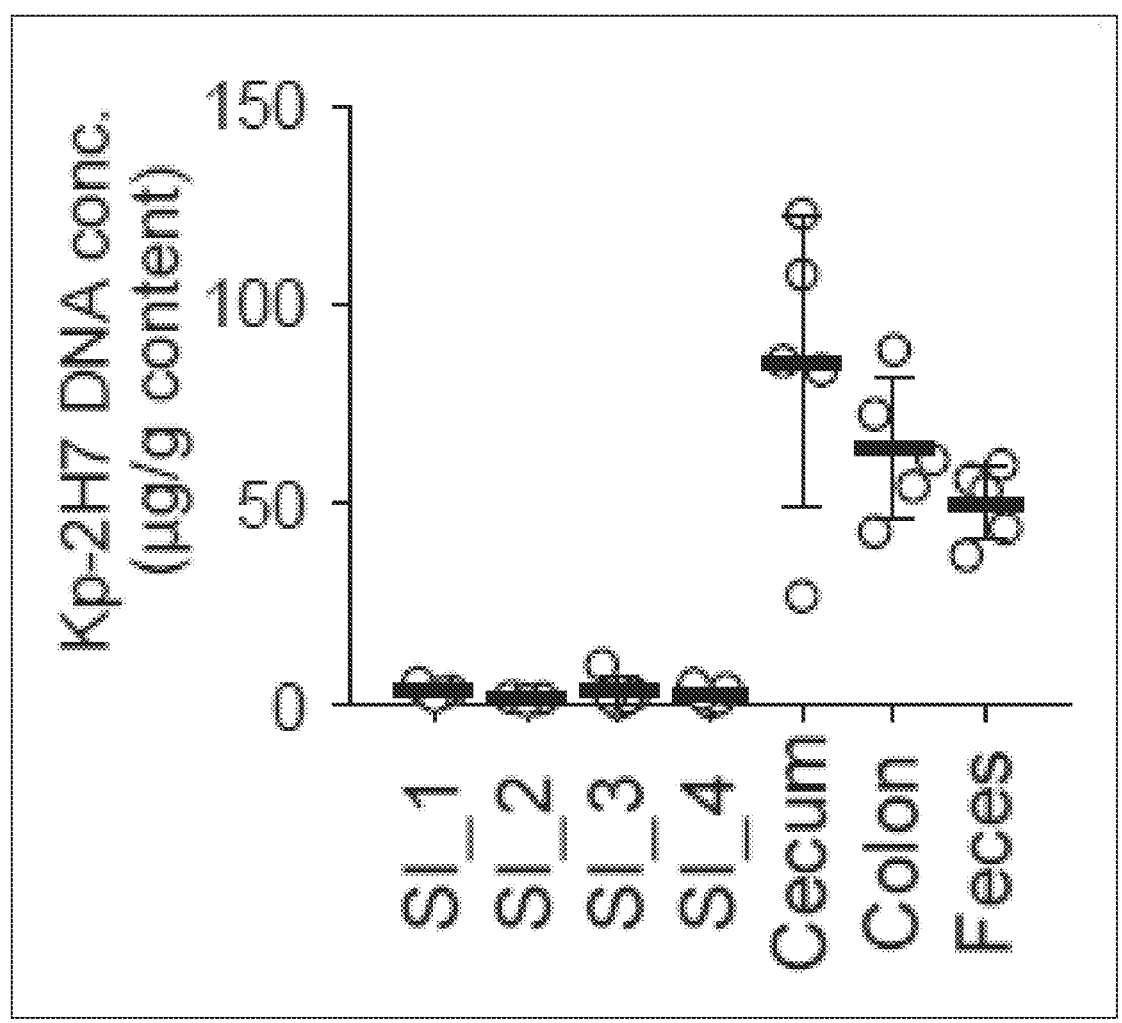
FIG. 7 is a graph for illustrating the result of q-PCR analysis of the Kp-2H7 DNA concentrations in feces and luminal contents from the small intestine (subdivided into four segments from proximal to distal portions: SI_1, SI_2, SI_3, and SI_4), cecum, and colon of the GF+Kp-2H7 mice (n=5). In the graph, each point represents data on an individual mouse. Error bars indicate means±standard deviations.
Figure 8:
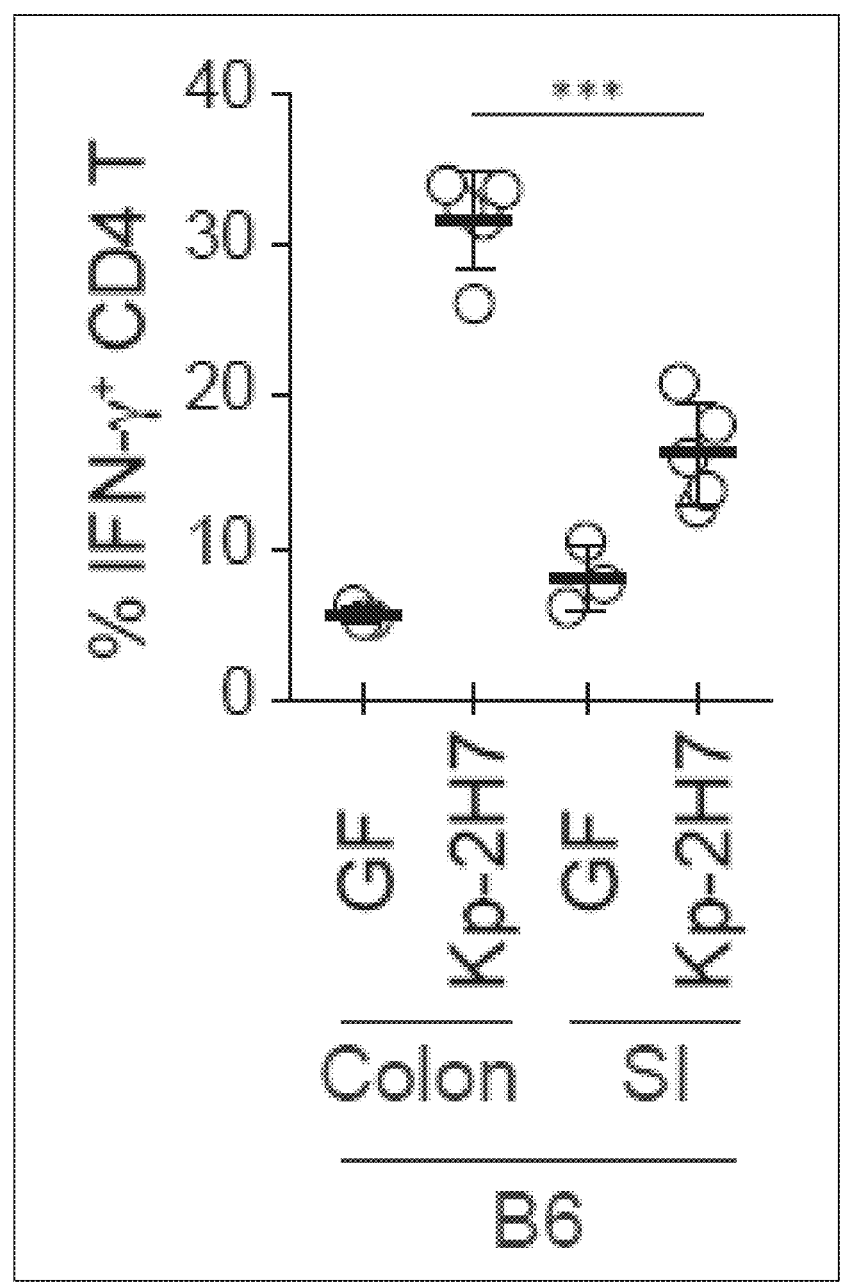
FIG. 8 is a graph for illustrating the result of q-PCR analysis of the percentage (%) of IFN-γ⁺ cells (Th1 cells) within CD4⁺ T cells in the LP of the colon or the small intestine of Kp-2H7-monocolonized GF B6 mice. In the graph, each point represents data on an individual mouse. Error bars indicate means±standard deviations. *** indicates $P<0.001$ (based on one-way analysis of variance (ANOVA) followed by Tukey's post hoc test).

The induction effect by Kp-2H7 was relatively specific to Th1 cells among the tested immune cells (see FIG. 5). Moreover, the induced Th1 cells exhibited negative reactions to interleukin 17, RORγt, and Foxp3, but exhibited positive reactions to T-bet and CD44 (see FIG. 6). These results suggested chronically activated/memory Th1 cells were produced (see S. Okada et al., Science 349, 606-613 (2015)). In addition, Kp-2H7 mainly colonized the colon, reflecting that Th1 cells were induced more prominently in the colon than in the small intestine (see FIGS. 7 and 8).

Figure 9:
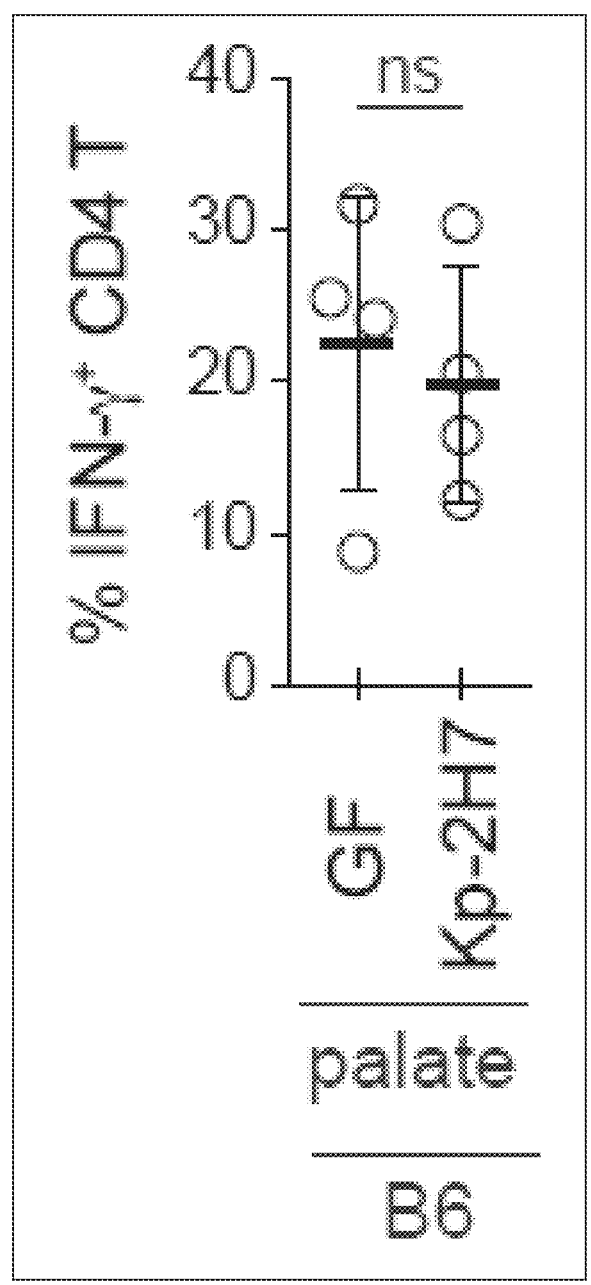
FIG. 9 is a graph for illustrating the result of q-PCR analysis of the percentage (%) of IFN-γ⁺ cells (Th1 cells) within CD4⁺ T cells in the palate of the Kp-2H7-monocolonized GF B6 mice. In the graph, each point represents data on an individual mouse. Error bars indicate means±standard deviations. ns indicates that no significant difference was found ($P>0.05$) (based on one-way analysis of variance (ANOVA) followed by Tukey's post hoc test).

Importantly, no increase in the percentage of Th1 cells present was found in the oral tissues (palate and tongue) of B6 GF Kp-2H7 mice, suggesting that the bacterium is innocuous in the oral cavity (see FIG. 9).

Figure 10:
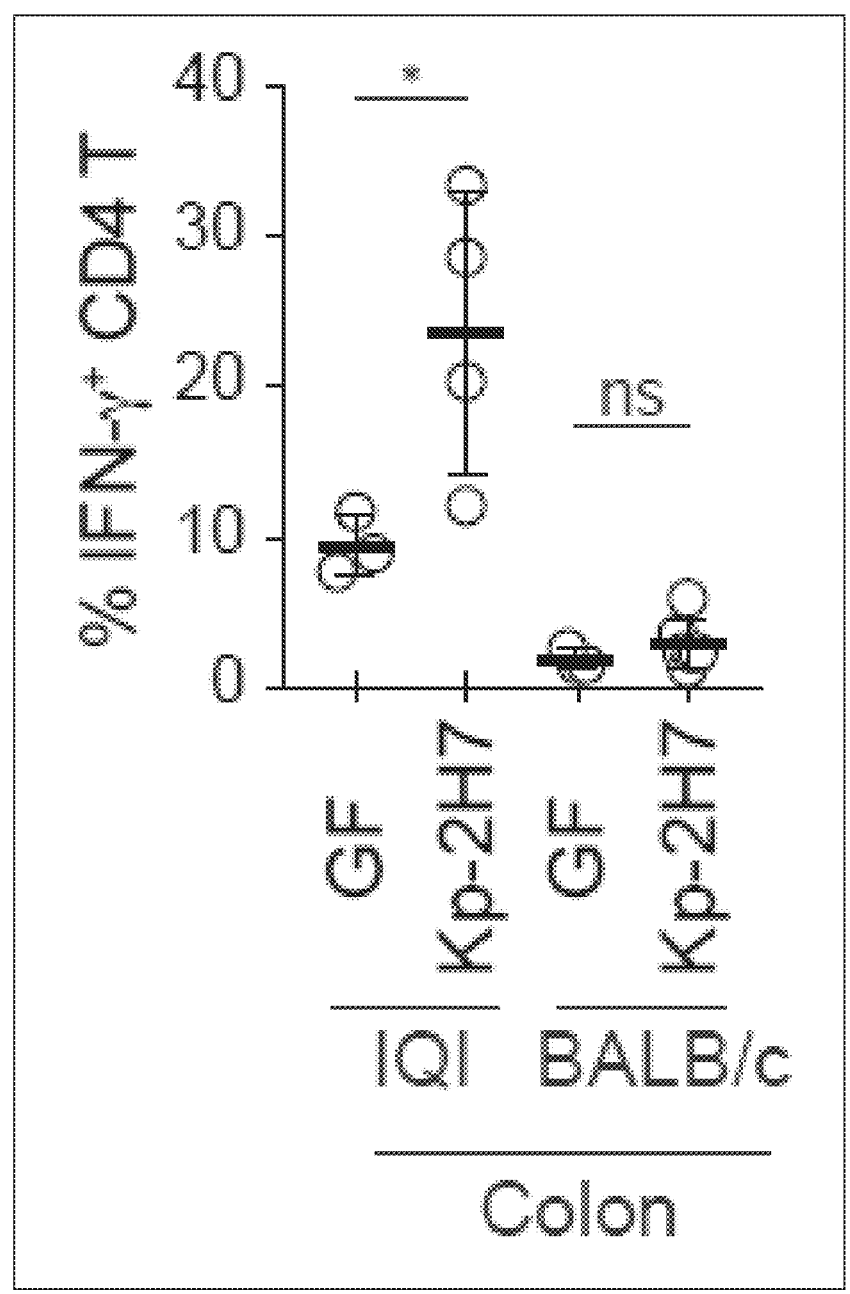
FIG. 10 is a graph for illustrating the result of q-PCR analysis of the percentage (%) of IFN-γ⁺ cells (Th1 cells) within CD4⁺ T cells in the colonic LP of Kp-2H7-monocolonized GF ICI mice or GF BALB/c mice. In the graph, each point represents data on an individual mouse. Error bars indicate means±standard deviations. * indicates $P<0.05$, and ns indicates that no significant difference was found ($P>0.05$) (based on one-way analysis of variance (ANOVA) followed by Tukey's post hoc test).

Meanwhile, increases in Th1 cells were found in IQI/Jic mice and B6 mice, but not in BALB/c. This suggests that the interplay between host genotype and Kp-2H7 is important for colonic Th1 cells induction (see FIG. 10)).

The bacterial species belonging to *Klebsiella* often acquire multi-drug resistance and can be a cause of healthcare-associated infection (see E. S. Snitkin et al., Science translational medicine 4, 148ra116 (2012), K. E. Holt et al., Proceedings of the National Academy of Sciences of the United States of America 112, E3574-3581 (2015), E. G. Pamer, Science 352, 535-538 (2016)).

Figure 11:
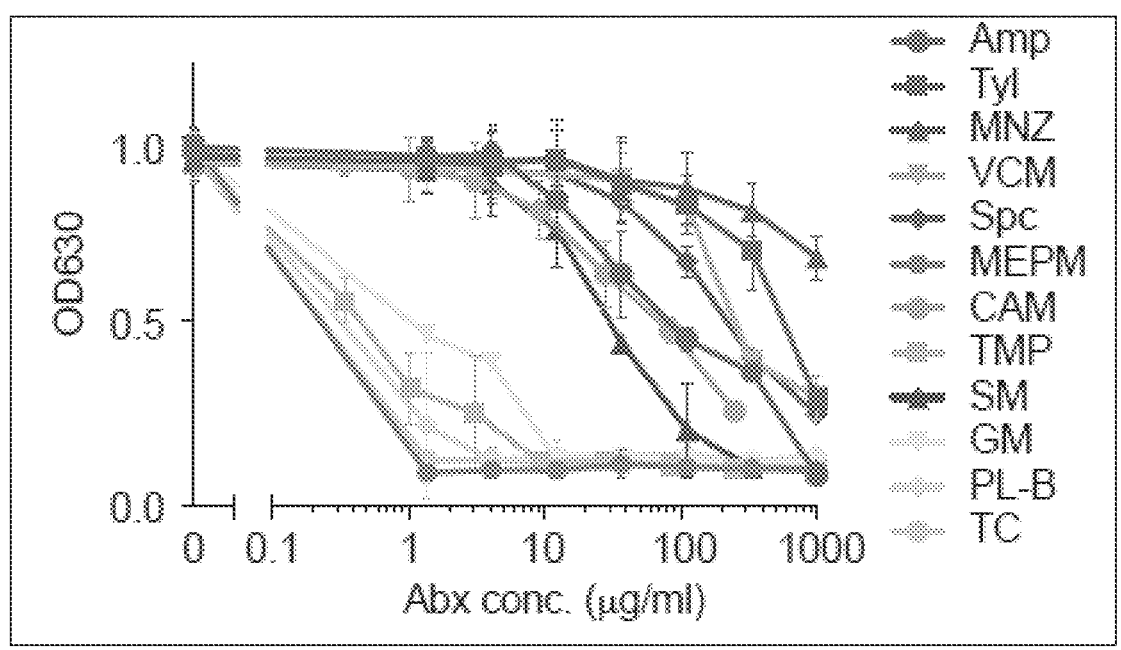
FIG. 11 is a graph for analyzing the Kp-2H7 growths in the presence of antibiotics. Kp-2H7 was cultured in a 96-well plate in the presence of different concentrations of the antibiotics at 37° C. for 24 hours. The bacterium growths were determined based on the absorbance measurement at a wavelength of 630 nm. Each data represents the mean±standard deviation based on the results of at least three independent experiments. "Amp" shows the result of the culturing in the presence of ampicillin; "Tyl", in the presence of tylosin; "MNZ", in the presence of metronidazole; "VCM", in the presence of vancomycin; "Spc", in the presence of spectinomycin; "MEPM", in the presence of meropenem; "CAM", in the presence of clarithromycin; "TMP", in the presence of trimethoprim; "SM", in the presence of streptomycin; "GM", in the presence of gentamycin; "PL-B", in the presence of polymyxin-B; and "TC", in the presence of tetracycline.
Figure 12:
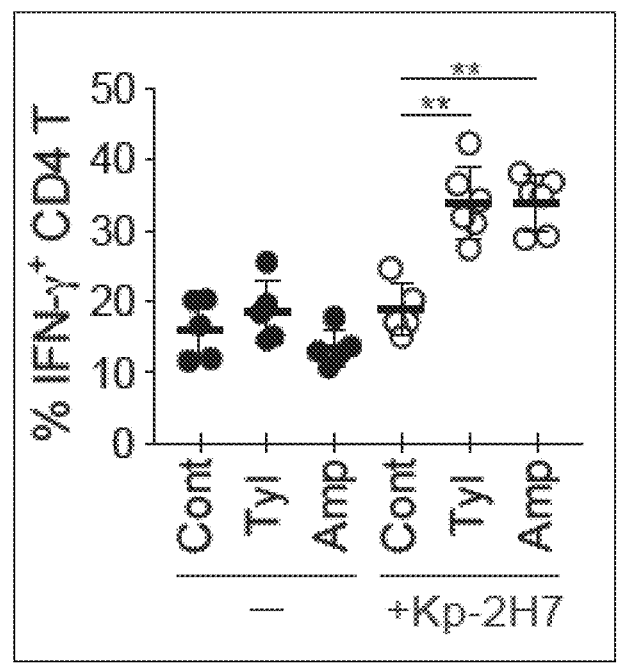
FIG. 12 is a graph for illustrating the result of flow cytometry analysis of the percentage of Th1 cells within colonic LP CD4⁺ T cells of untreated SPF B6 mice (Cont, control) or SPF B6 mice continuously treated with an antibiotic (Tyl: tylosin or Amp: ampicillin) via the drinking water, starting 4 days before administration of 2×10⁸ CFU Kp-2H7, the analysis being performed on day 21 after the Kp-2H7 administration. In the graph, "-" and "+Kp-2H7" respectively indicate the Kp-2H7-unadministered group and -administered group. Each point represents data on an individual mouse. Error bars indicate means±standard deviations. ** indicates $P<0.01$ (based on one-way analysis of variance (ANOVA) followed by Tukey's post hoc test).

Kp-2H7 isolated by the present inventors exhibited resistances to various antibiotics such as ampicillin (Amp), tylosin (Tyl), spectinomycin (Spc), and metronidazole (MNZ) as shown in FIG. 11 and Table 12. Moreover, as shown in FIG. 12, the strong Kp-2H7 colonization was accompanied by marked increase in colonic Th1 cells.

TABLE 12

| Antibiotic | MIC (μg/ml) | CLSI |
|---|---|---|
| Penicillins | | |
| Ampicillin | >16 | R |
| Piperacillin | ≤8 | S |
| Cephems | | |
| Cefaclor | ≤4 | S |
| Cefpodoxime-Proxetil | ≤1 | S |
| Cefazolin | 1 | S |
| Cefotiam | ≤0.5 | S |
| Cefotaxime | ≤0.5 | S |
| Ceftazidime | ≤1 | S |
| Cefpirome | ≤4 | S |
| Cefmetazole | ≤8 | S |
| Flomoxef | ≤8 | S |
| Carbapenems | | |
| Imipenem/Cilastatin | ≤0.25 | S |
| Meropenem | ≤0.25 | S |
| Monobactams | | |
| Aztreonam | ≤1 | S |
| β-lactamase inhibitors | | |
| Amoxicillin/Clavulanate | ≤4 | S |
| Sulbactam/Cefoperazone | ≤4 | S |
| Aminoglycosides | | |
| Gentamicin | ≤2 | S |
| Amikacin | ≤8 | S |
| Tetracyclins | | |
| Minocycline | ≤2 | S |
| Others | | |
| Sulfamethoxazole- | ≤20 | S |

TABLE 12-continued

| Antibiotic | MIC (μg/ml) | CLSI |
|---|---|---|
| Trimethoprim | | |
| Levofloxacin | ≤1 | S |
| Fosfomycin | 16 | I |

Next, the present inventors examined the colitogenic potential of K-2H7. As a result, despite the induction of Th1 cells, Kp-2H7 did not cause any inflammatory changes in the intestines of wildtype (WT) hosts, B6 GF mice monocolonized with the bacterium, or Amp-treated mice colonized therewith, as shown in FIGS. 13 to 16.

Since the interplay between microbial and genetic factors greatly contributes to the pathogenesis of IBD (see H. Chu et al., Science 352, 1116-1120 (2016)), the influence of Kp-2H7 colonization in $Il10^{-/-}$B6 mice, which are genetically prone to colitis, was examined.

Kp-2H7 or *Escherichia coli* strain ID 2B1 (Ec-2B1) was orally administered to GF $Il10^{-/-}$ mice or Amp-treated SPF $Il10^{-/-}$ mice.

Note that Ec-2B1 is a bacterium isolated from the GF+CD #2 mice but has a weak Th1 cell-inducing capability as shown in FIG. 4. Moreover, *K. pneumoniae* and *E. coli* belong to Enterobacteriaceae, and this family includes bacteria involved in IBD pathogenesis (see NPL 2, X. C. Morgan et al., Genome biology 13, R79 (2012)).

As a result, the histological analysis revealed as shown in FIGS. 13 to 17 that Kp-2H7 induced more severe inflammation than Ec-2B1, in the proximal colons of the exGF mice or the ampicillin-treated SPF $Il10^{-/-}$ mice.

This suggests that Kp-2H7 acts as a gut pathobiont by inducing the Th1 cell response and possibly additional pro-inflammatory effect in a species-specific and host genotype-specific fashion.

It is noteworthy that, although unillustrated, when Kp-2H7 was intratracheally injected into the lung, a Th17 response predominated over a Th1 response in the lung T cells. In addition, the response was accompanied by severe lung pathology even in genetically normal mice.

Therefore, the strong influence of Kp-2H7 on Th1 induction was gut-specific, presumably due to the contribution of gut-specific epithelial cells (ECs) and dendritic cells (DCs).

Example 2

To explore the mechanism underlying Kp-2H7-mediated Th1 cell induction, various approaches were taken.

Figure 18:
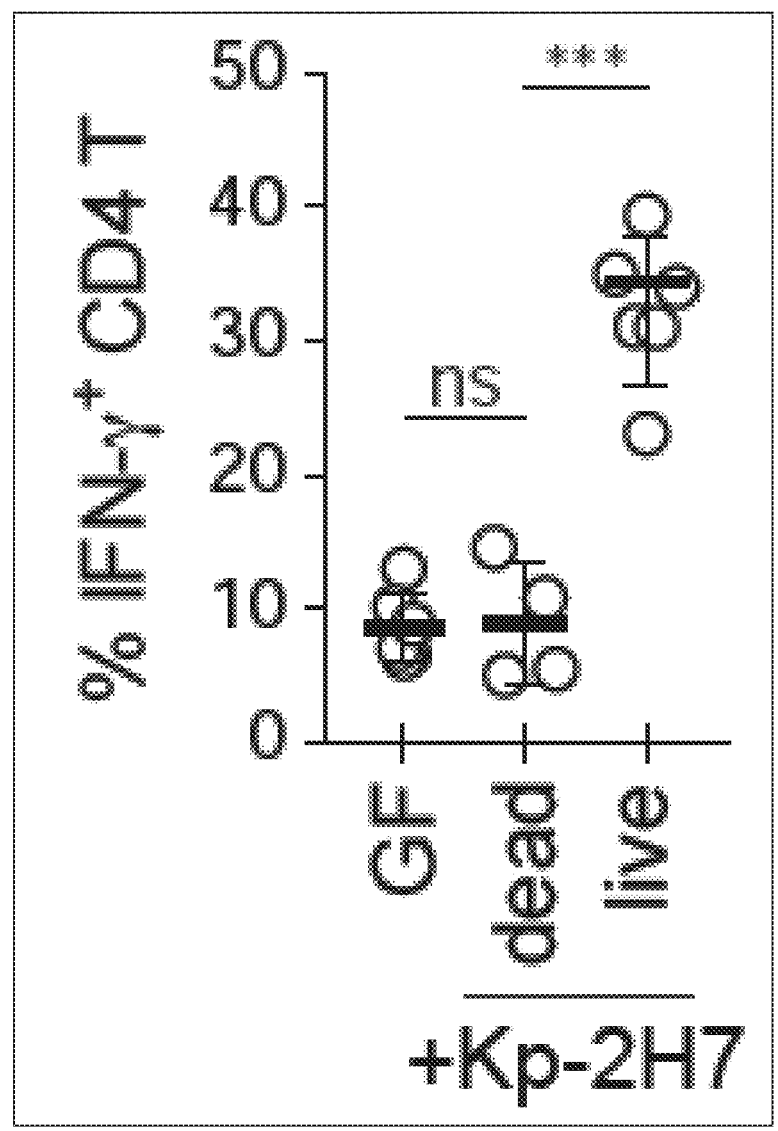
FIG. 18 is a graph showing the frequency of Th1 cells in each colon of GF mice receiving Kp-2H7 via the drinking water for 3 weeks (in the graph, "live") and GF mice receiving heat-killed Kp-2H7 via the drinking water for 3 weeks (in the graph, "dead"). In the graph, "GF" indicates a Kp-2H7-unadministered group. Each point represents data on an individual mouse. Error bars indicate means±standard deviations. ns indicates that no significant difference was found (P>0.05), and indicates P<0.001 (based on one-way analysis of variance (ANOVA) followed by Tukey's post hoc test).

First, whether dead bacteria could induce Th1 cells in vivo was examined. To be more specific, in vitro-cultured Kp-2H7 was heat-killed and orally administered to GF mice via drinking water for 3 weeks. As a result, the heat-killed bacteria did not influence the frequency of Th1 cells as shown in FIG. 18.

Hence, to examine the specific localization of Kp-2H7, the colons of mice colonized with Kp-2H7 were examined by in situ hybridization.

Figure 19:
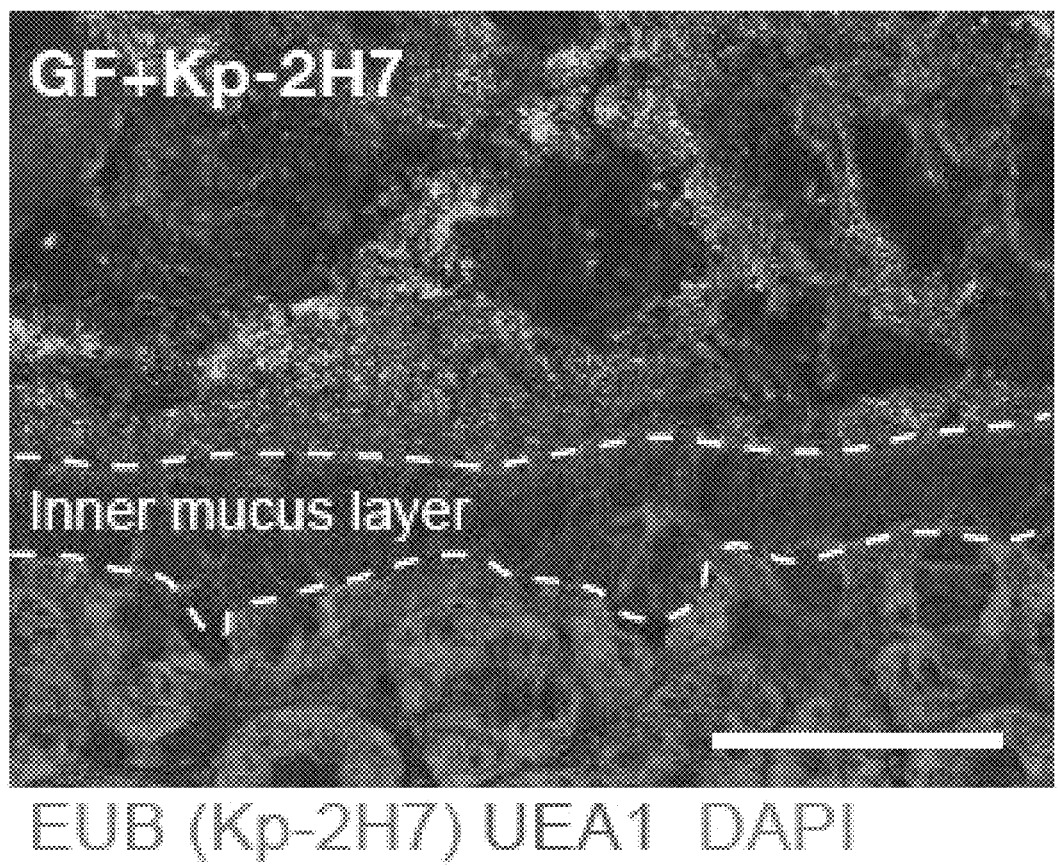
FIG. 19 is a fluorescence micrograph for illustrating the observation result of the proximal colon of a GF mouse monocolonized with Kp-2H7, the proximal colon being stained with DAPI (indicated in blue in the figure), EUB338 FISH probe (indicated in green in the figure), and *Ulex Europaeus* Agglutinin I (UEA1, indicated in red in the figure).

As a result, Kp-2H7 existed on the mucin layer as shown in FIG. 19, and no evidence of adhesion or invasion on or into the epithelial layer was found. These results suggest that the Th1 induction is mediated by the activity of live bacteria localized distantly from the epithelial layer.

Next, to further elucidate the mechanism, eight different *K. pneumoniae* strains shown in Table 13 were prepared, which were derived from human, mice, or the environment.

TABLE 13

| Strain ID | Isolated from | gapA | infB | mdh | pgi | phoE | rpoB | IonB | MLST-type | wzi-type (Homology) | wzc-type (Homology) | TH1-induction capability |
|---|---|---|---|---|---|---|---|---|---|---|---|---|
| Kp-2H7 | Cecal content of GF mice inoculated with CD#2 saliva | 2 | 1 | 1 | 1 | 9 | 1 | 93 | 323 | wzi287 (446/447) | K21 (136/136) | |
| ATCC 700603 (K6) | Urine of a hospitalized patient | 16 | 22 | 26 | 71 | 98 | 52 | 51 | 489 | wzi20-K20 (425/447) | K53 (124/124) | |
| ATCC BAA-1705 (ART 2008133) | Urine of a 42 year-old patient | 3 | 3 | 1 | 1 | 1 | 1 | 79 | 258 | wzi81-K81 (446/447) | K85 (99/134) | |
| 34E1 | Cecal content of SPF mice treated with Amp | 2 | 60 | 11 | 1 | 4 | 8 | 24 | 628 | wzi9-K9 (430/447) | K41 (101/141) | |
| Kp-40B3 | Cecal content of GF mice inoculated with Healthy#1 saliva | 43 | 1 | 2 | 1 | 10 | 4 | 13 | 818 | wzi72-K2 (447/447) | K2 (133/133) | |
| ATCC 700721 (MGH78578) | Urine of a 66 year-old patient | 2 | 1 | 2 | 1 | 2 | 2 | 2 | 38 | wzi50-K15, K17, K50, K51, K52 (447/447) | K52 (136/136) | |
| ATCC 13882 (NCTC:8172) | Water | 7 | 1 | 6 | 1 | 1 | 1 | 84 | 505 | wzi64-K14, K64 (447/447) | K84 (148/148) | |
| KP-1 | Not specified environmental origin | 2 | 3 | 2 | 2 | 6 | 4 | 4 | 29 | wzi115-K54 (447/447) | K54 (115/115) | |
| ATCC BAA-2552 (342) | Maise plant | 16 | 24 | 30 | 27 | 36 | 22 | 55 | 146 | wzi20-K20 (430/447) | K30 (133/144) | |
| KCTC 2242 | Not described | 43 | 1 | 2 | 1 | 10 | 4 | 13 | 818 | wzi72-K2 (447/447) | K2 (133/133) | |

Figure 20:
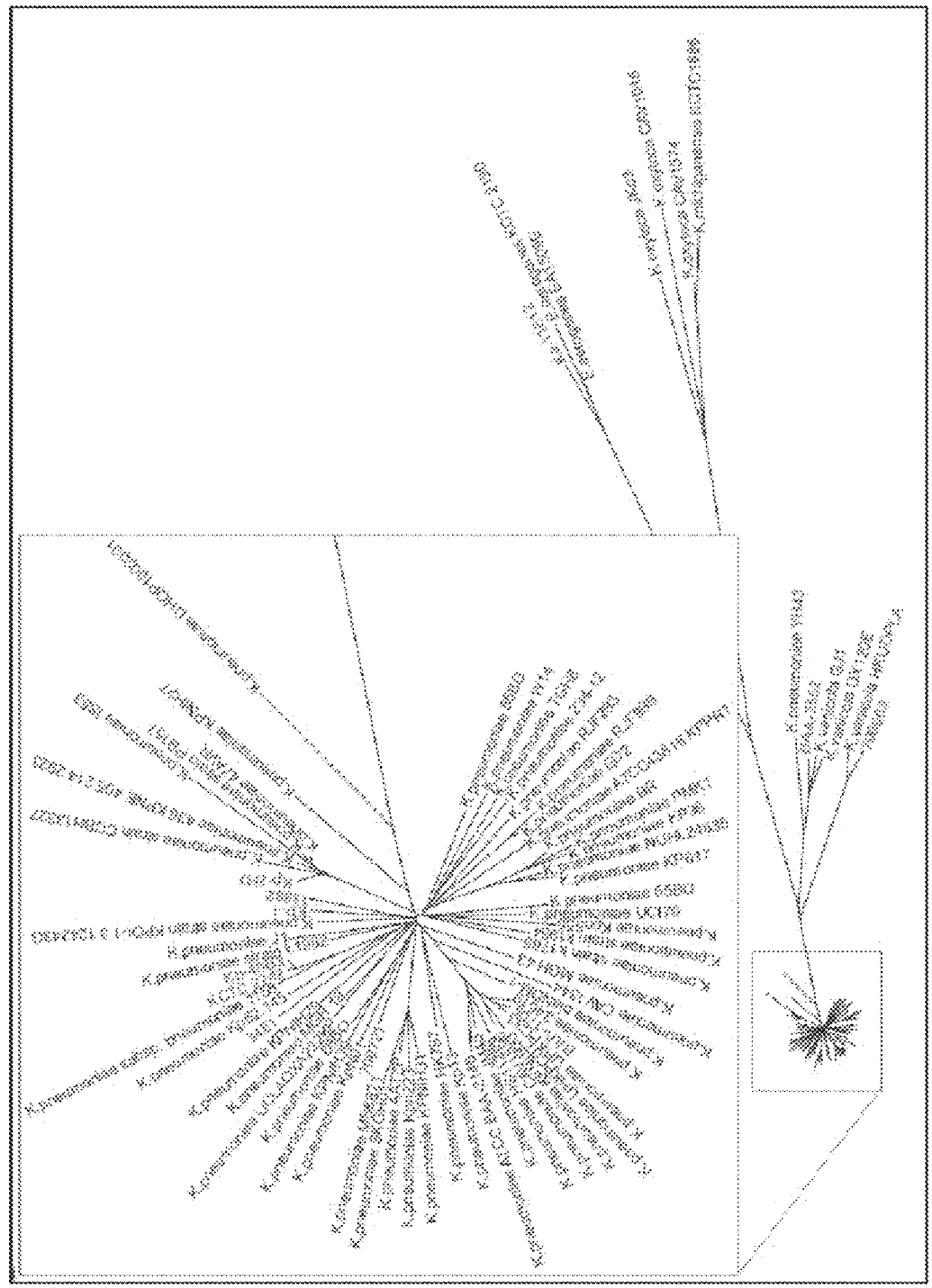
FIG. 20 is a phylogenetic tree constructed based on Mash distance by analyzing the whole genomes of *K. pneumoniae* strains using neighbor-joining method.

First, Kp-2H7 and the eight *K. pneumoniae* strains were newly sequenced or the sequences were obtained from public databases, and subjected to multilocus sequence typing (MLST), sequence based capsular (K) typing, and core genome phylogeny analysis. Thereby, it was revealed that these were phylogenetically different (see Table 13 and FIG. 20).

Figure 21:
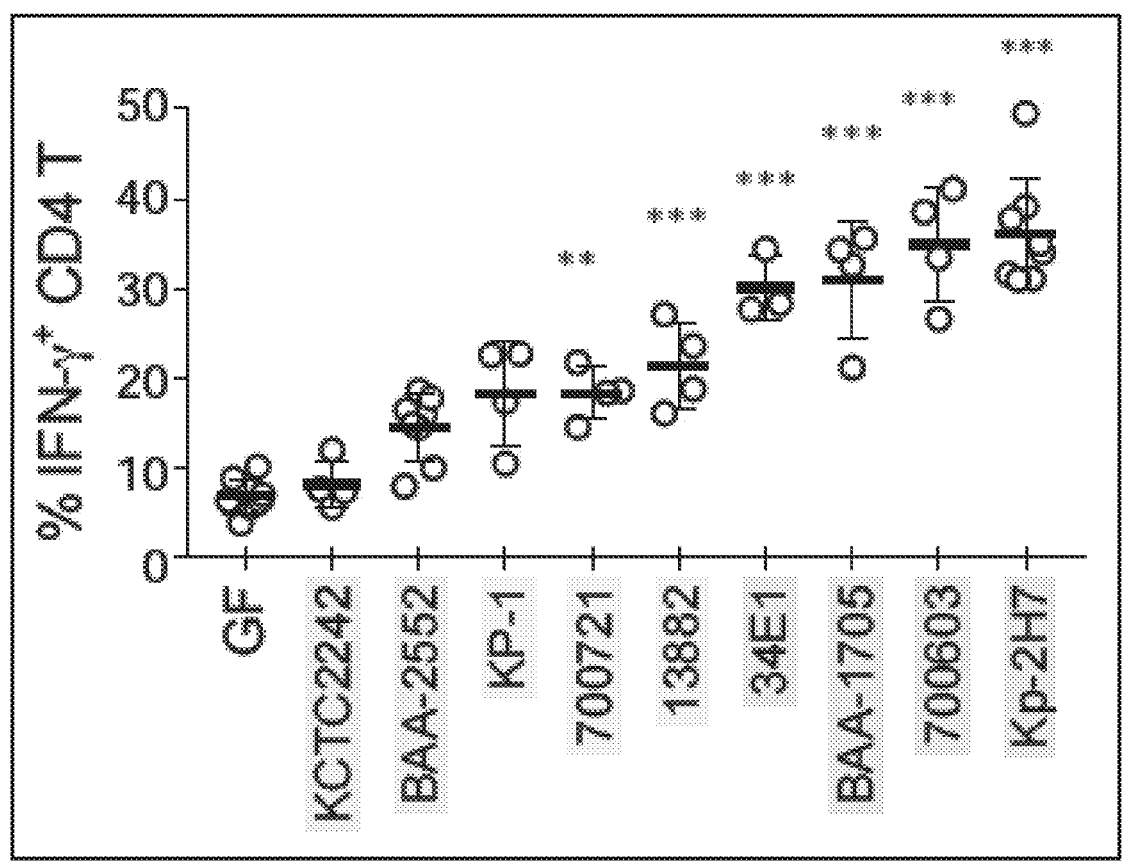
FIG. 21 is a graph for illustrating the result of analyzing Th1 cells 3 weeks after GF mice were monocolonized with each *K. pneumoniae* strain. In the graph, the vertical axis represents the frequency of IFN-γ⁺ colonic LP CD4⁺TCRβ⁺ T cells. Each point represents data on an individual mouse. Error bars indicate means±standard deviations.  indicates P<0.01, and * indicates P<0.001 (based on one-way analysis of variance (ANOVA) followed by Tukey's post hoc test).

Next, B6 mice monocolonized with each bacterial strain were prepared. As a result, the tested bacterial strains were found to considerably vary in the ability to induce Th1 cells in the colon as shown in FIG. 21. To be more specific, in some bacterial strains such as ATCC700603, BAA-1705, and 34E1, the Th1 cell induction was found at frequencies comparable to Kp-2H7, but the other strains had low inducing capabilities. Particularly, KCTC2242 and BAA2552 did not or only weakly influence the Th1 cell frequency. This suggests that the Th1 cell induction is specific to bacterial strains.

Figure 22:
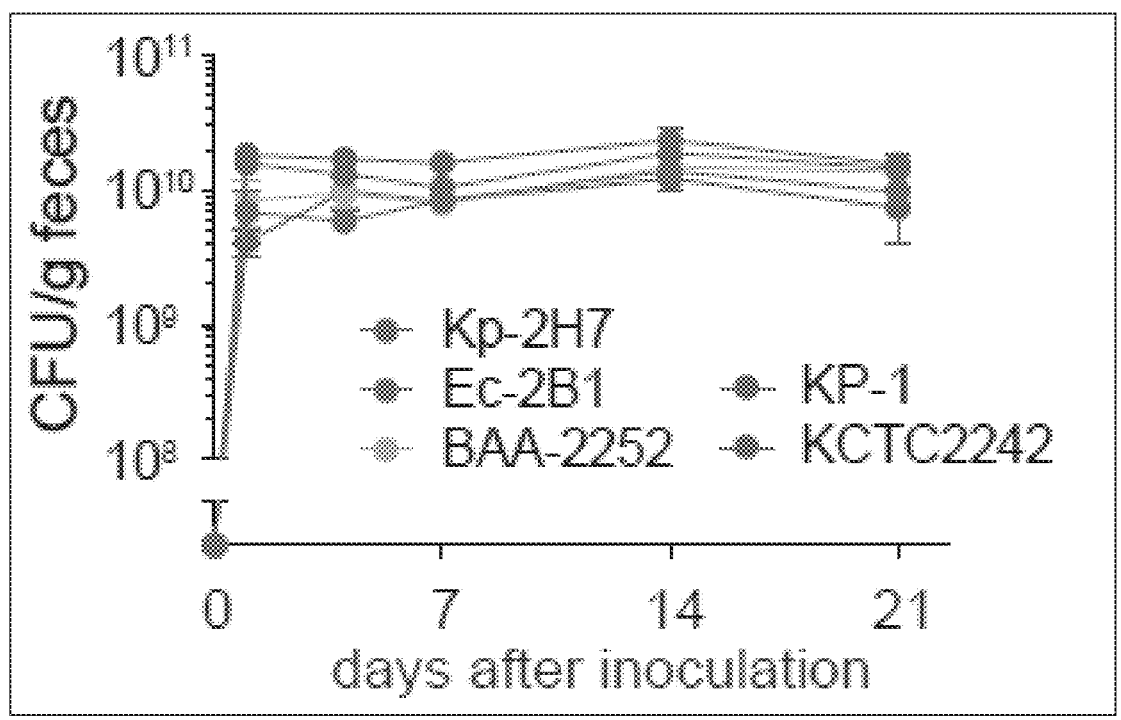
FIG. 22 is a graph for illustrating the change over time of the bacterial load in feces of GF mice gavaged with each *K. pneumoniae* strain, the change being represented by colony forming units (CFU).

Moreover, the intensity of inducing these Th1 cells was independent on bacterial load and was not accompanied by inflammation (see FIG. 22). Further, there was no correlation between Th1-cell induction and MLST, K-typing, and phylogeny (see FIGS. 20, 21 and Table 13).

Figure 23:
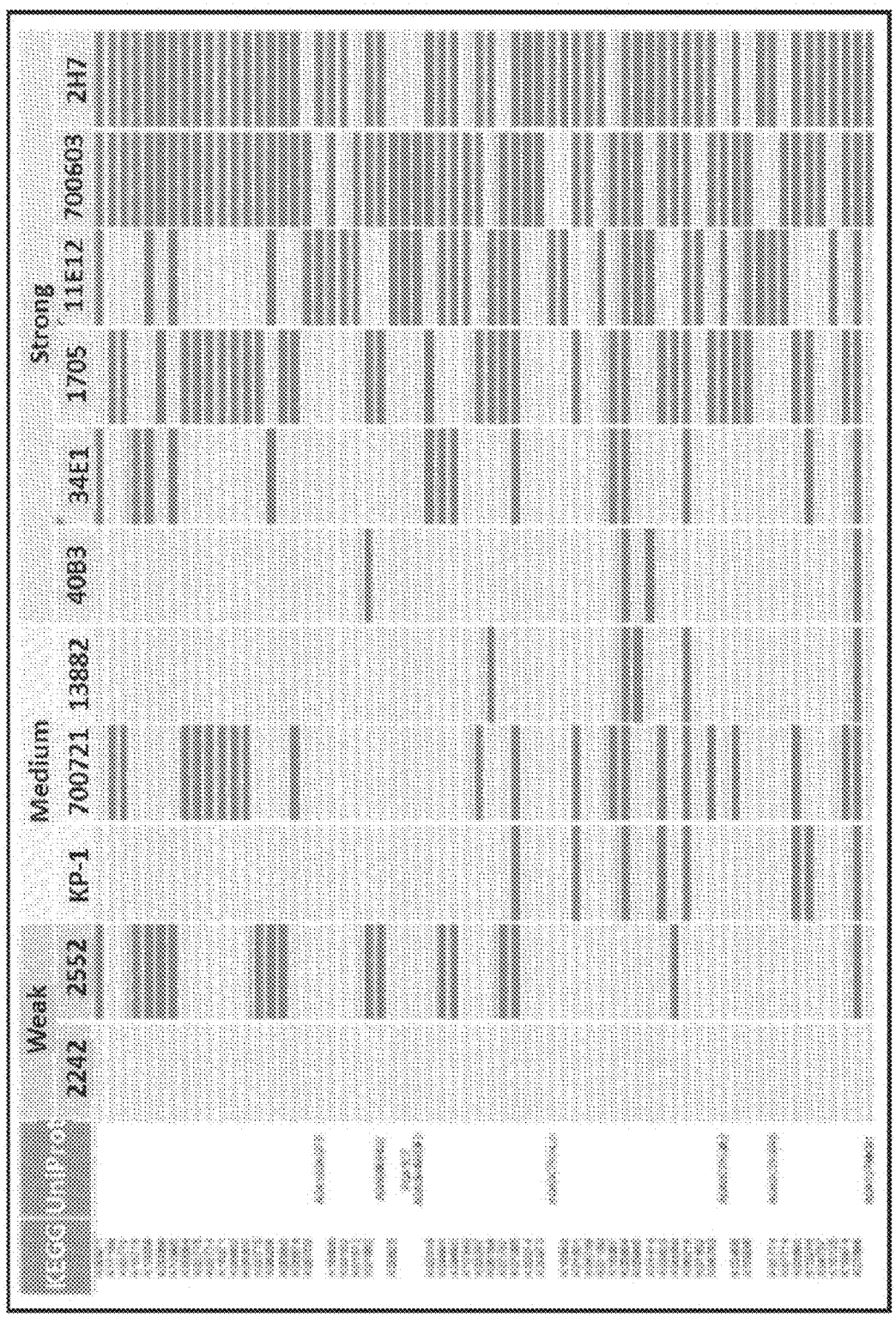
FIG. 23 is a representation for illustrating a correlation between a Th1-induction related gene group (64 genes whose functions have been already known) selected based on the result of comparative genomics among bacterial strains belonging to *Klebsiella* and whether or not each of the bacterial strains belonging to *Klebsiella* comprises the genes (see FIGS. 53-62 for the details). Note that, based on the result of the comparative genomics among the bacterial strains belonging to *Klebsiella*, the top 100 genes were selected based on the sum of multiplications of whether to comprise the gene or not (0 or 1) and the relative induction level. Further, from the top 100 genes, those whose functions have been already known (64 genes) were selected as the Th1-induction related gene group.

The result of the comparative analysis of the whole genomes revealed that a 64-gene group was positively correlated with the Th1 induction as shown in FIG. 23. The gene group included genes predicted to encode enzymes involved in fructose-, galactitol-, and mannose-related uptake and metabolic processes (see FIG. 23 and FIGS. 53-62).

These genes have been reported to be expressed abundantly in inflammatory diseases, accordingly suggested to have immunomodulatory actions, and thereby may be involved in Th1-cell induction (see NPL 1, X. C. Morgan et al., Genome biology 13, R79 (2012), A. R. Records, Molecular plant-microbe interactions: MPMI 24, 751-757 (2011), S. Fukuda et al., Nature 469, 543-547 (2011), A. N. Thorburn, L. Macia, C. R. Mackay, Immunity 40, 833-842 (2014)).

Next, the present inventors made efforts to explore the host cell signal transduction mediating Th1 induction. Particularly, the involvement of innate immune signaling pathways was examined by using Kp-2H7-monocolonized GF Myd88$^{-/-}$ mice, Myd88$^{-/-}$Trif$^{-/-}$ mice, and Tlr4$^{-/-}$ mice.

Figure 24:
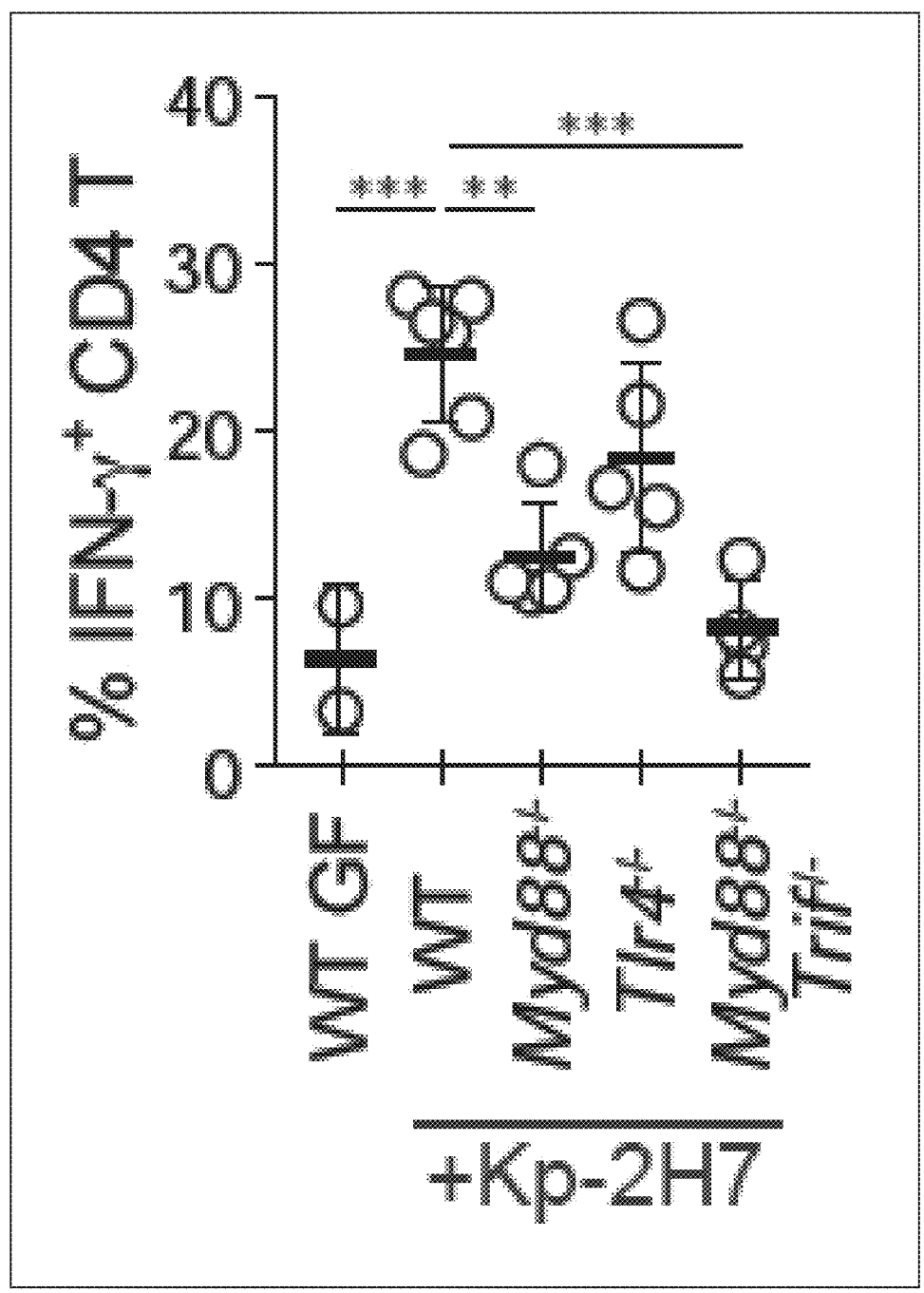
FIG. 24 is a graph showing the percentage of Th1 cells in the colons of Kp-2H7-monocolonized WT mice, Myd88$^{-/-}$ mice, Tlr4$^{-/-}$ mice, and Myd88$^{-/-}$Trif$^{-/-}$ mice. In the graph, each point represents data on an individual mouse. Error bars indicate means±standard deviations.  indicates P<0.01, and * indicates P<0.001 (based on one-way analysis of variance (ANOVA) followed by Tukey's post hoc test).

The magnitude of Th1 induction was significantly lower in the Myd88$^{-/-}$ mice and Myd88$^{-/-}$Trif$^{-/-}$ mice, and partially attenuated in the Tlr4$^{-/-}$ mice (see FIG. 24). This suggests an involvement of innate immune signaling pathways mediated through Toll-like receptors (TLRs) and possibly through other MyD88-dependent receptors, including IL-1b and IL-18.

RNA sequencing was performed on the gene expression profiles of colonic ECs and DCs isolated from wildtype mice monocolonized with Kp-2H7 or BAA2552 for 1 week, as well as from wildtype mice, Myd88$^{-/-}$ mice, Myd88$^{-/-}$Trif$^{-/-}$ mice, and Tlr4$^{-/-}$ mice monocolonized with Kp-2H7 for 3 weeks, for comparison to GF mice (see FIGS. 25 to 28).

Figure 29:
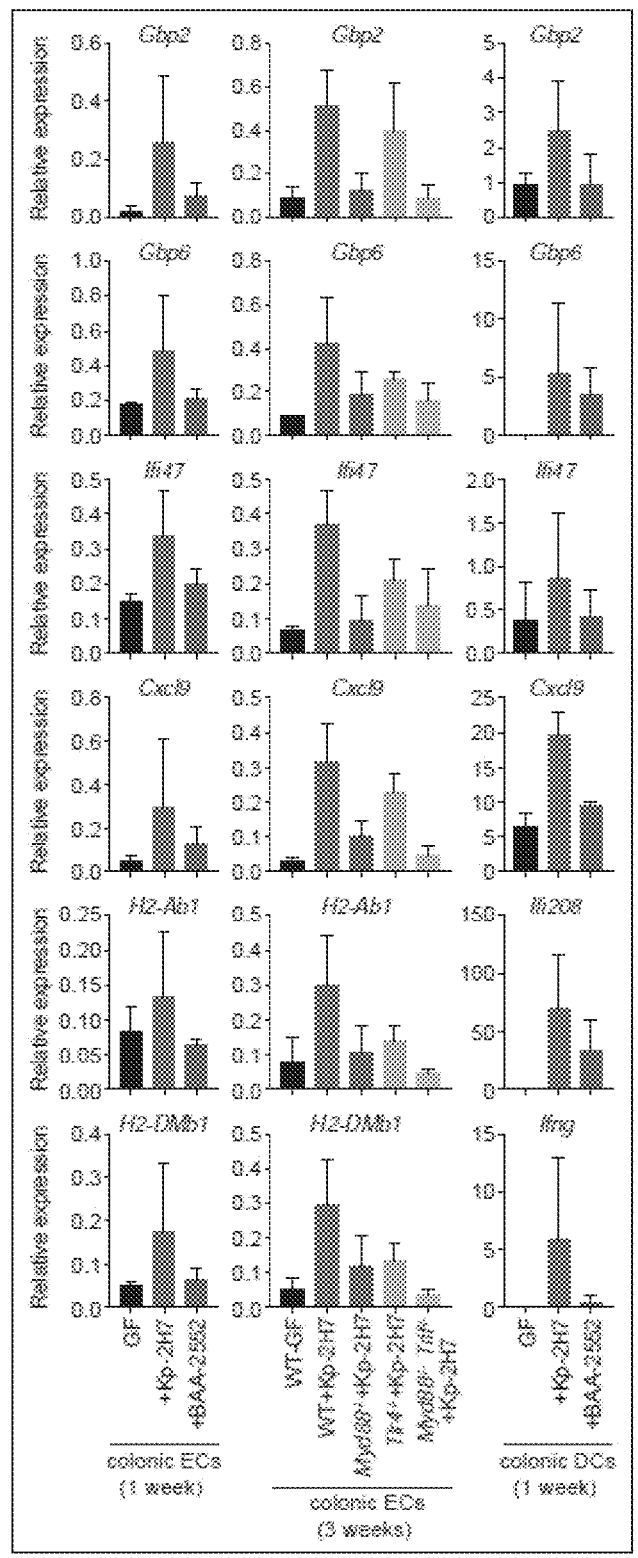
FIG. 29 shows graphs for illustrating the result of q-PCR analysis of each gene expression in colonic epithelial cells or dendritic cells of mice monocolonized with each bacterial strain. In a graph, the vertical axis represents values normalized to the Gapdh expression for each gene. Error bars indicate standard deviations. Moreover, "1 week" or "3 weeks" denotes weeks after the cell-strain inoculations.
Figure 30:
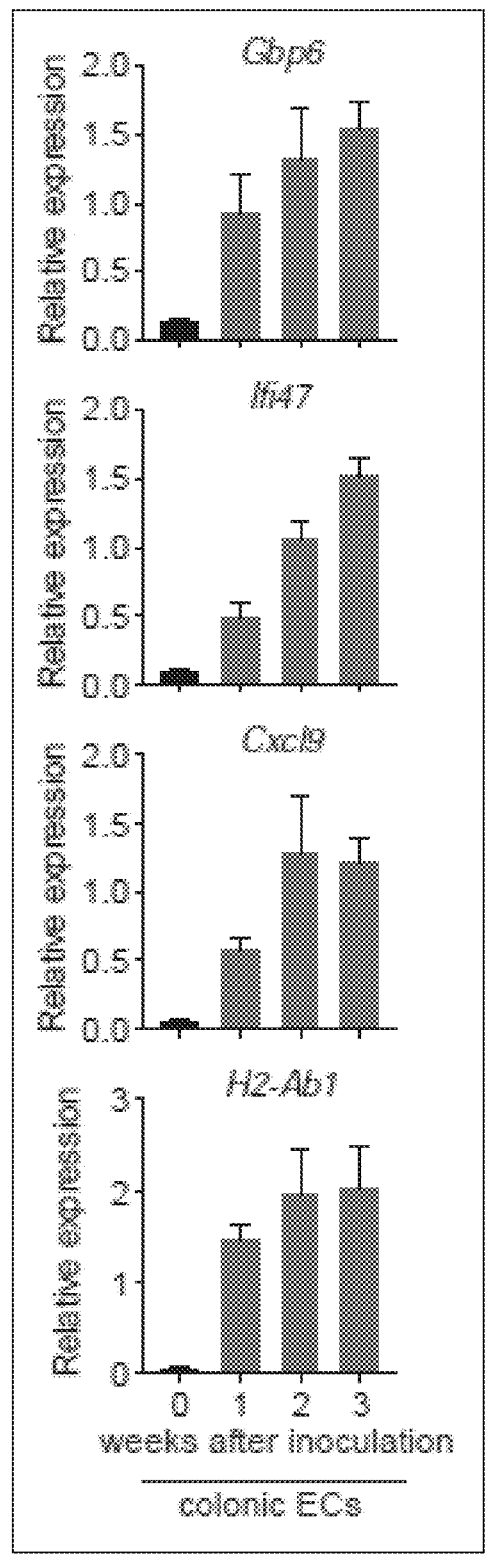
FIG. 30 shows graphs for illustrating the over time result of q-PCR analysis of each gene expression in the colonic epithelial cells of the mice monocolonized with Kp-2H7. In a graph, the vertical axis represents values normalized to the Gapdh expression for each gene. Error bars indicate standard deviations. Moreover, the horizontal axis represents weeks after the cell-strain inoculation.
Figure 31:
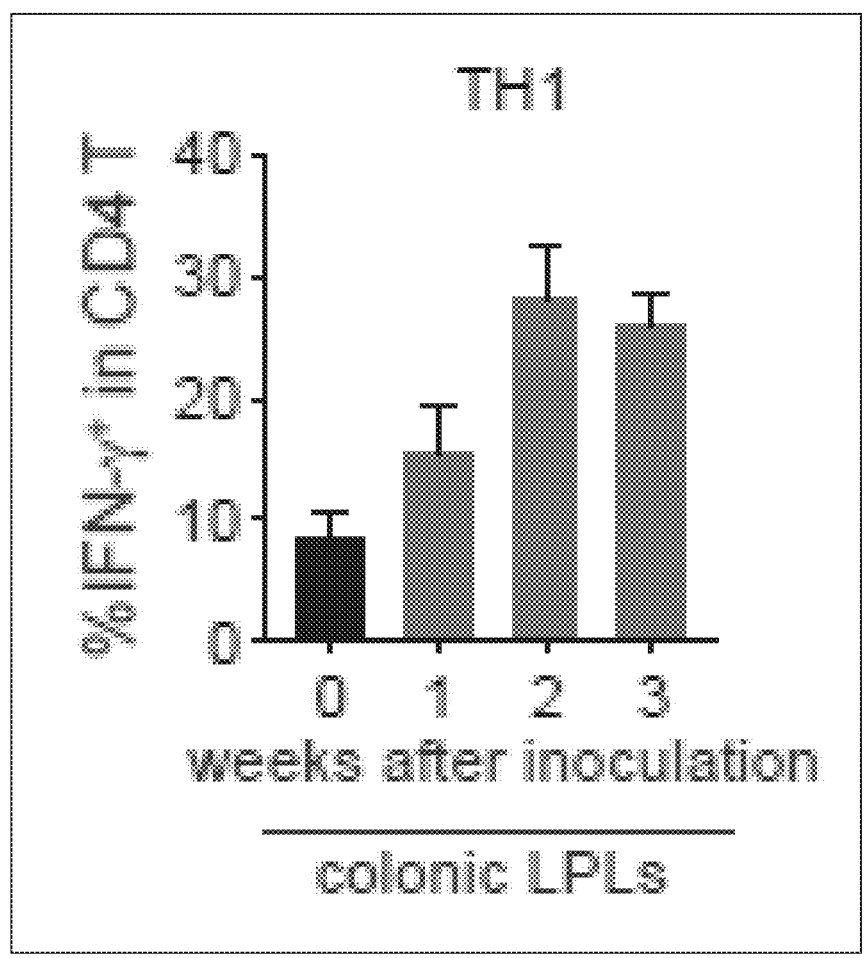
FIG. 31 is a graph for illustrating the over time result of flow cytometry analysis of the percentage of Th1 cells in colonic lamina propria lymphocytes (LPL) of the mice monocolonized with Kp-2H7. In the graph, error bars indicate standard deviations. Moreover, the horizontal axis represents weeks after the cell-strain inoculation.

IFN-inducible (IFI) genes, such as major histocompatibility complex-related molecules involved in antigen processing/presentation (for example, H2-DMb1, H2-Ab1, and Tap1) and guanylate-binding proteins (GBPs), were significantly upregulated in the colonic ECs and DCs from the GF WT+Kp-2H7 mice. Moreover, as shown in FIG. 29, expression differences were confirmed by qPCR analysis. As shown in FIGS. 25 and 29 to 31, the upregulation of IFI genes in ECs and DCs and Ifng gene in DCs notably began during the early phase of colonization (one week) when the Th1 induction was limited. This suggests that the upregulation of IFN-g and IFI was not just a consequence, but involved in the Th1 cell induction.

Figure 32:
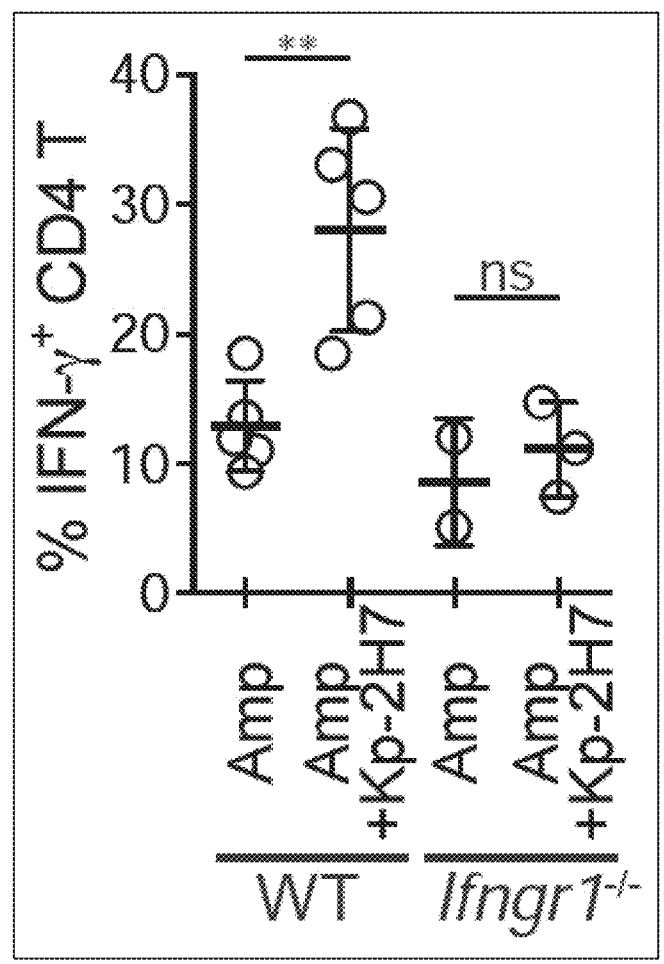
FIG. 32 is a graph showing the percentage of Th1 cells within colonic LPCD4⁺ cells of SPF WT mice or SPF Ifngr1$^{-/-}$ mice treated with ampicillin (Amp) and gavaged with Kp-2H7 or not subjected to the administration. In the graph, each point represents data on an individual mouse. Error bars indicate means±standard deviations. ns indicates that no significant difference was found (P>0.05), ** indicates P<0.01 (based on one-way analysis of variance (ANOVA) followed by Tukey's post hoc test).

Consistent with this interpretation, IFN-g receptor 1-deficient (IFNgR1$^{-/-}$) mice resulted in a defective Th1 cell induction upon the Kp-2H7 colonization as shown in FIG. 32.

Taken together, K. pneumoniae strains produce certain innate immune ligands. The ligands can cross the mucin layer and gain access to intestinal ECs and DCs. As a result, MyD88- and IFI-dependent signaling pathways are activated, conceivably leading to the induction of Th1 cells.

Example 3

To further confirm the link between oral-derived bacteria and Th1 cell induction, additional saliva samples were obtained from two healthy donors (He #1 and He #2) and two patients with active ulcerative colitis (UC) (UC #1 and UC #2), and these samples were orally administered to GF WT B6 mice.

Figure 33:
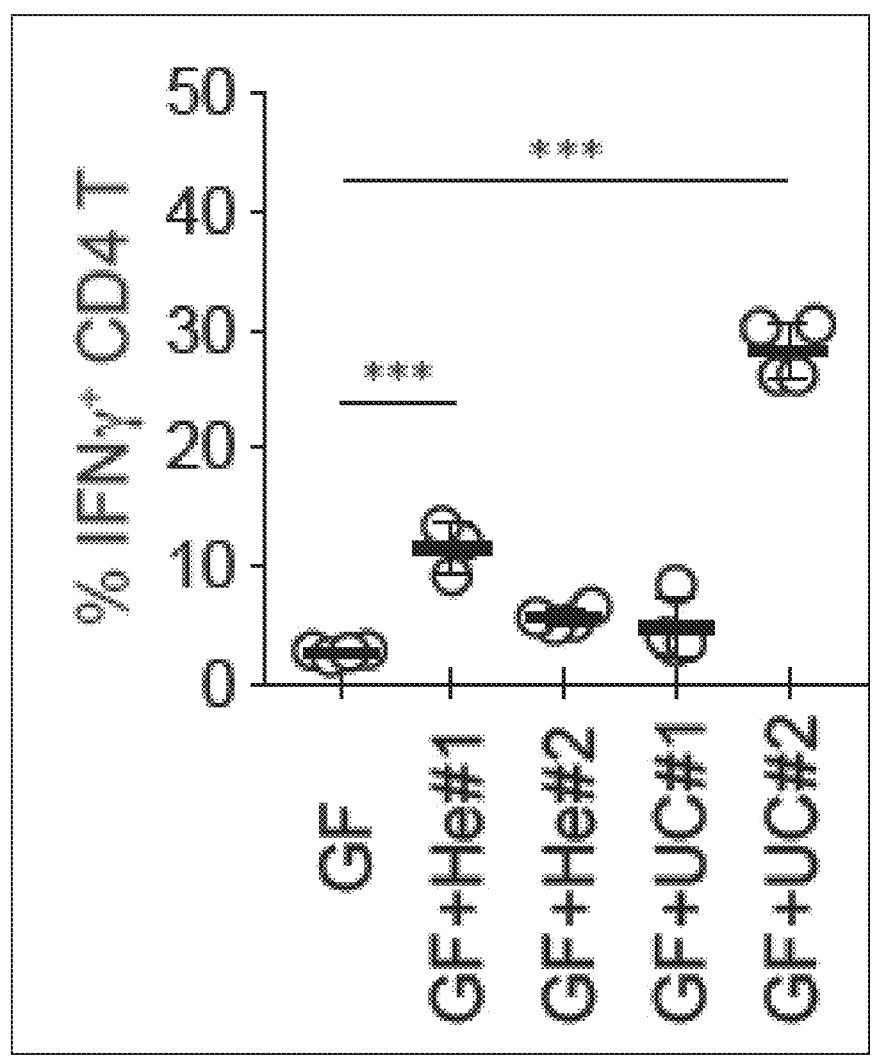
FIG. 33 is a graph showing the frequencies of IFNγ⁺ cells among colonic LP CD4⁺TCRβ⁺ T cells of exGF mice inoculated with saliva samples from healthy donors (He #1, He #2) and ulcerative colitis patients (UC #1, UC #2), respectively. In the graph, each point represents data on an individual mouse. Error bars indicate means±standard deviations. *** indicates P<0.001 (based on one-way analysis of variance (ANOVA) followed by Tukey's post hoc test).

As a result, a marked accumulation of Th1 cells was found in the colonic LP of the mice (GF+UC #2 mice) inoculated with the saliva sample obtained from the UC patient #2, at a level comparable to that in the GF+CD #2 mice as shown in FIG. 33.

Figure 34:
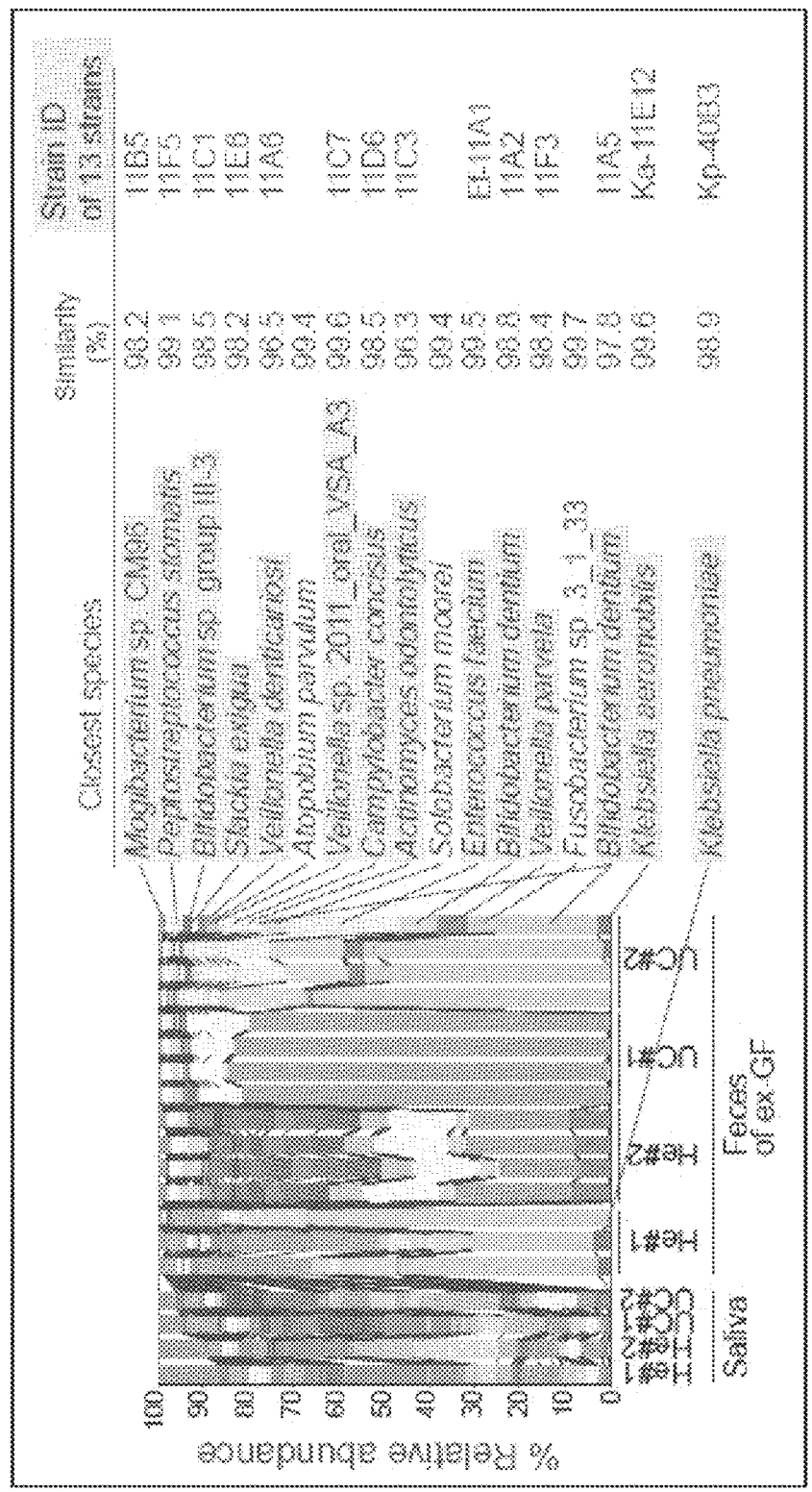
FIG. 34 is a diagram for illustrating the result of pyrosequencing analysis of 16S rRNAs of saliva microbiotas of the healthy controls and ulcerative colitis patients as well as fecal microbiotas of the exGF mice inoculated with saliva microbiotas, respectively (in each group, n=3 or 4). The diagram shows the relative abundance of the OTUs and known bacterial species closely related to each OTU. Moreover, 13 isolated bacterial strains corresponding to the OTUs and Kp-40B3 are marked in green and yellow, respectively.

To isolate bacterial strains responsible for the detected Th1 cell induction, cecal contents of the GF+UC #2 mice were collected and cultured in vitro. As a result, the present inventors successfully isolated 13 strains, which roughly represented the microbiota of the GF+UC #2 mice, as shown in FIG. 34.

Figure 35:
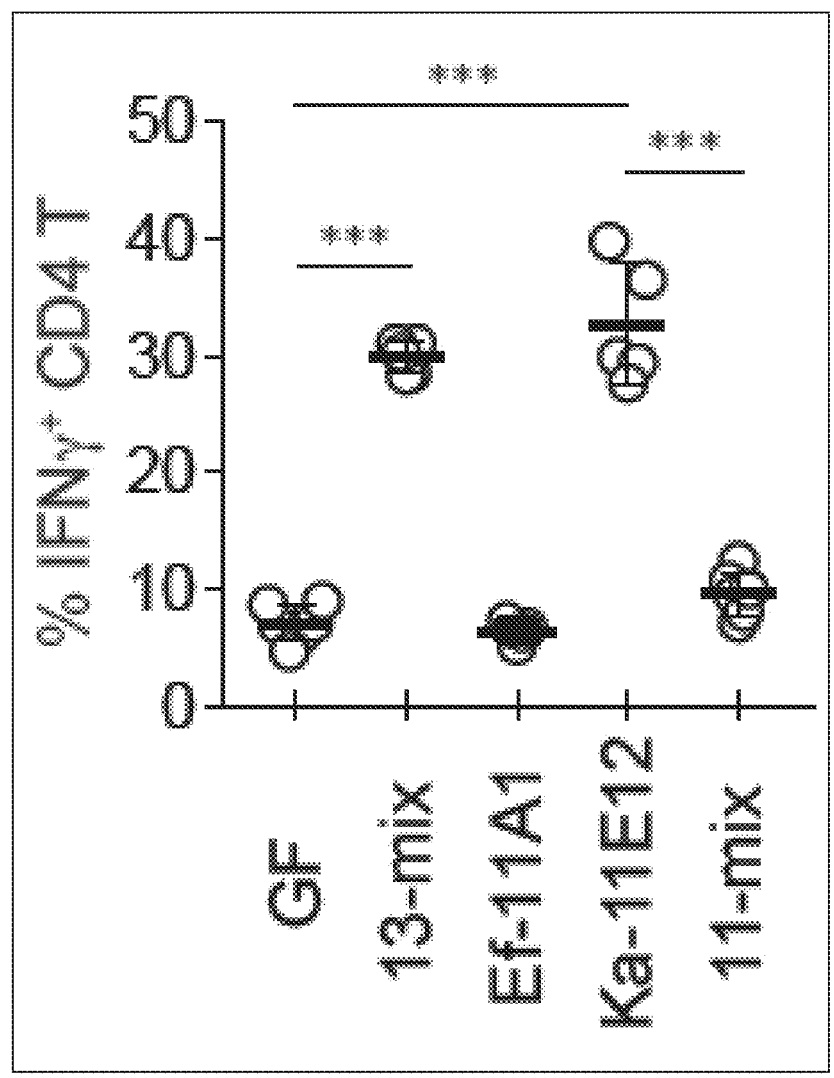
FIG. 35 is a graph showing the percentage of Th1 cells in the colonic LP of B6 mice colonized with a mixture of the 13 strains (13-mix), Ef-11A1, Ka-11E12, or a mixture of 11 strains (11-mix). In the graph, each point represents data on an individual mouse. Error bars indicate means±standard deviations. *** indicates P<0.001 (based on one-way analysis of variance (ANOVA) followed by Tukey's post hoc test).

Moreover, orally administering a mixture of the 13 strains (13-mix) into GF mice fully replicated the phenotype detected in the GF+UC #2 mice in terms of colonic Th1 cell induction (see FIGS. 33, 35).

Among the 13 bacterial strains, Enterococcus faecium strain ID 11A1 (Ef-11A1) and Klebsiella aeromobilis 11E12 (Ka-11E12) drew attention because both species have been reported as important pathobionts involved in IBD pathogenesis and exhibiting multidrug resistance (see Y. Taur, E. G. Pamer, Current opinion in infectious diseases 26, 332-337 (2013), A. Davin-Regli, J. M. Pages, Frontiers in microbiology 6, 392 (2015), S. Mondot et al., Inflammatory bowel diseases 17, 185-192 (2011)).

Note that reclassification of K. aeromobilis from Enterobacter aerogenes has recently been proposed. Moreover, this bacterium is phylogenetically very close to K. pneumoniae, with 99% 16S rRNA gene sequence identity (see S. M. Diene et al., Molecular biology and evolution 30, 369-383 (2013)).

Hence, GF mice were gavaged with Ef-11A1, Ka-11E12, or a mixture of the other 11 bacterial strains (11-mix). As a result, Ka-11E12 induced a marked accumulation of Th1 cells in the colon at a level comparable to those found in the GF+13-mix mice and the GF+UC #2 mice as shown in FIG. 35. On the other hand, such induction was not found from Ef-11A1 and 11-mix.

Therefore, even though Ka-11E12 is merely a minor bacterium in the gut microbiota of the GF+UC #2 mice, Ka-11E12 is likely the major factor of the Th1 cell induction found in the GF+UC #2 mice (see FIG. 34).

Figure 36:
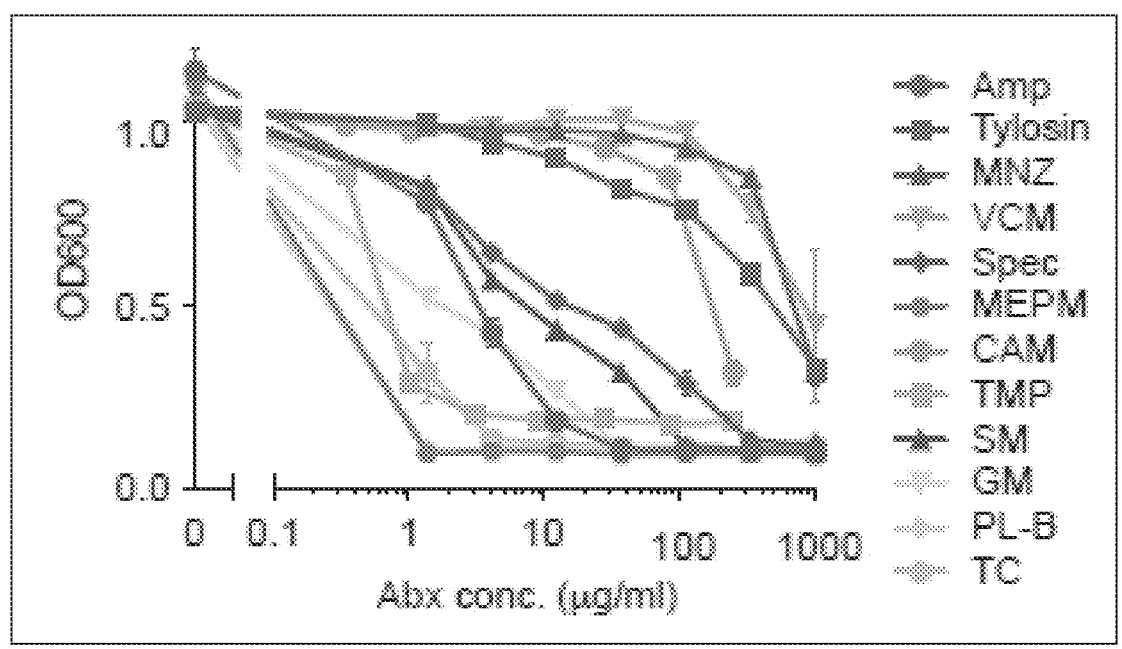
FIG. 36 is a graph for analyzing the Ka-11E12 growths in the presence of antibiotics. Ka-11E12 was cultured in a 96-well plate in the presence of different concentrations of the antibiotics at 37° C. for 24 hours. The bacterium growths were determined based on the absorbance measurement at a wavelength of 630 nm. Each data represents the mean±standard deviation based on the results of at least three independent experiments. "Amp" shows the result of the culturing in the presence of ampicillin; "Tylosin", in the presence of tylosin; "MNZ", in the presence of metronidazole; "VCM", in the presence of vancomycin; "Spec", in the presence of spectinomycin; "MEPM", in the presence of meropenem; "CAM", in the presence of clarithromycin; "TMP", in the presence of trimethoprim; "SM", in the presence of streptomycin; "GM", in the presence of gentamycin; "PL-B", in the presence of polymyxin-B; and "TC", in the presence of tetracycline.

In addition, as shown in FIG. 36 and Table 14, Ka-11E12 exhibited resistances to multiple antibiotics.

TABLE 14

| Antibiotic | MIC (μg/ml) | CLSI |
|---|---|---|
| Penicillins | | |
| Ampicillin | >16 | R |
| Piperacillin | ≤8 | S |
| Cephems | | |
| Cefaclor | 8 | S |
| Cefpodoxime-Proxetil | ≤1 | S |
| Cefazolin | >4 | R |
| Cefotiam | ≤0.5 | S |
| Cefotaxime | ≤0.5 | S |
| Ceftazidime | ≤1 | S |
| Cefpirome | ≤4 | S |
| Cefmetazole | 16 | S |
| Flomoxef | ≤8 | S |
| Carbapenems | | |
| Imipenem/Cilastatin | ≤0.25 | S |
| Meropenem | ≤0.25 | S |
| Monobactams | | |
| Aztreonam | ≤1 | S |
| β-lactamase inhibitors | | |
| Amoxicillin/Clavulanate | >16 | R |
| Sulbactam/Cefoperazone | ≤4 | S |
| Aminoglycosides | | |
| Gentamicin | ≤2 | S |
| Amikacin | ≤8 | S |
| Tetracyclins | | |
| Minocycline | ≤2 | S |
| Others | | |
| Sulfamethoxazole-Trimethoprim | ≤ 20 | S |
| Levofloxacin | ≤1 | S |
| Fosfomycin | 16 | I |

Figure 37:
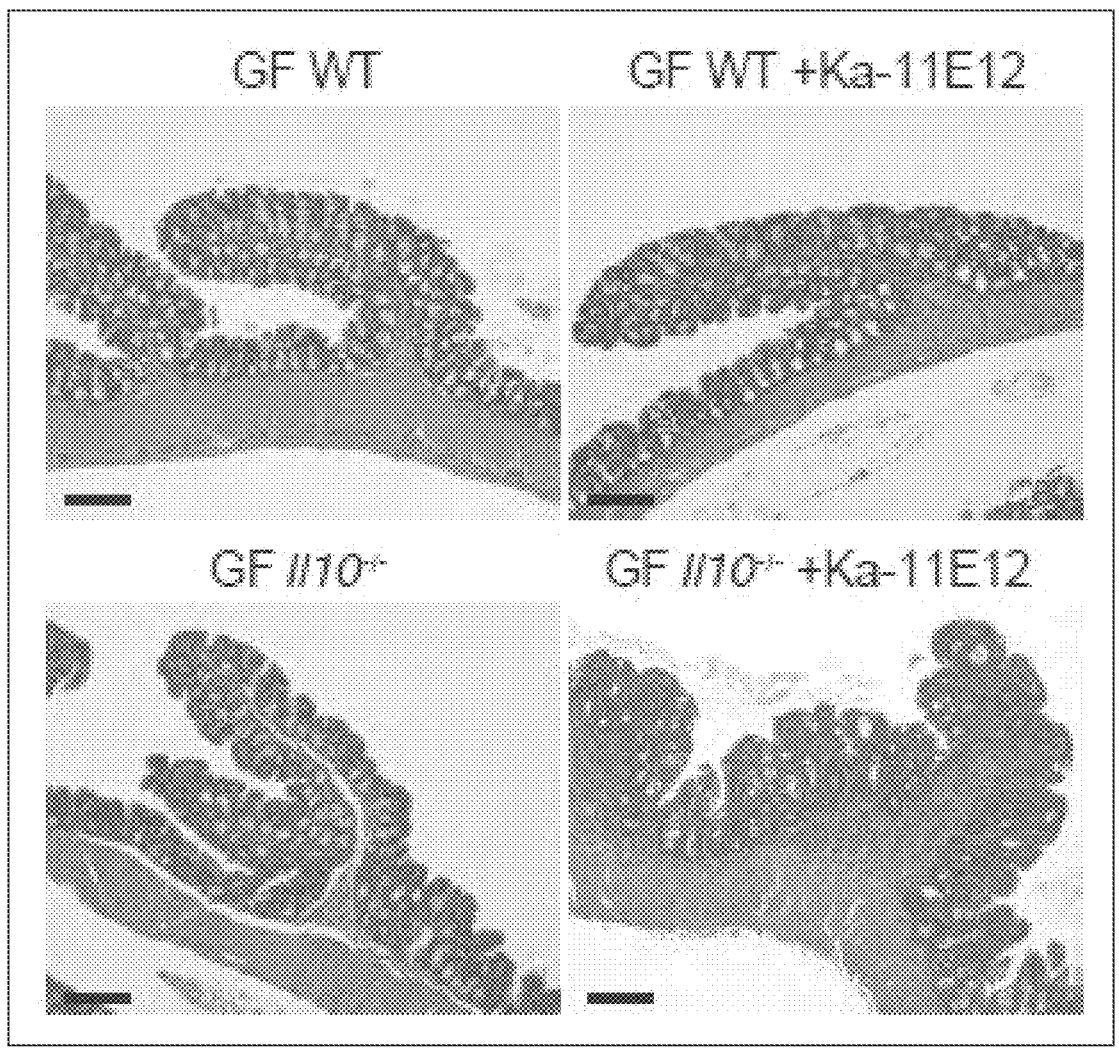
FIG. 37 shows photographs for illustrating the result of microscope observation of the proximal colons of GF wildtype or GF Il10$^{-/-}$ mice monocolonized or not colonized with Ka-11E12. The figure shows representative examples of the H&E staining analysis result obtained 5 weeks after the Ka-11E12 administration. The scale bars represent 200 μm.
Figure 38:
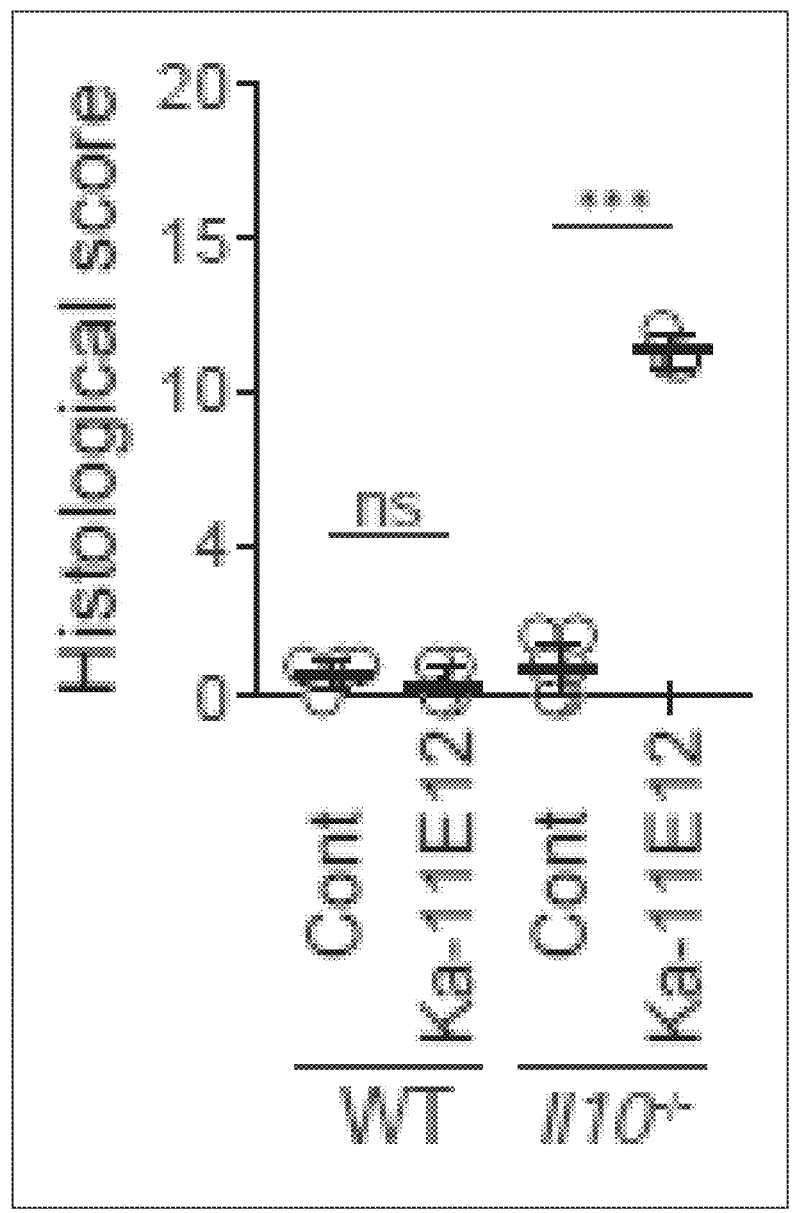
FIG. 38 is a graph for illustrating the result of analyzing the histological colitis scores of the proximal colons of the GF wildtype or GF Il10$^{-/-}$ mice monocolonized or not colonized with Ka-11E12. In the graph, "Cont" indicates the result of the bacterium-unadministered group. Each point represents data on an individual mouse. Error bars indicate means±standard deviations. ns indicates that no significant difference was found (P>0.05), *** indicates P<0.001 (based on one-way analysis of variance (ANOVA) followed by Tukey's post hoc test).
Figure 39:
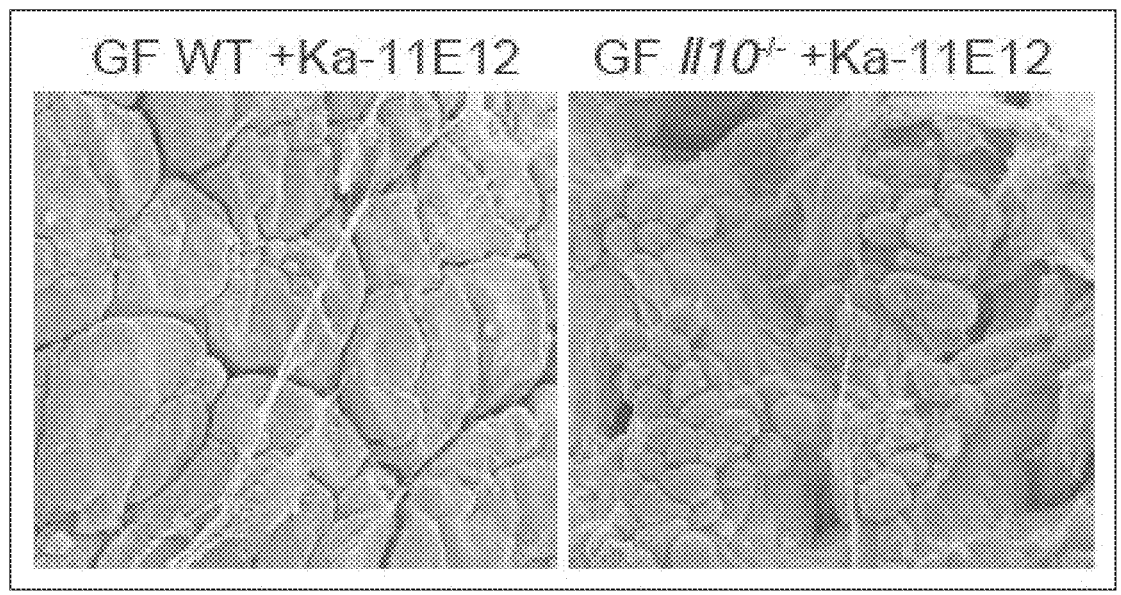
FIG. 39 shows representative SEM images for illustrating the result of observing the colons of the wildtype or Il10$^{-/-}$ mice monocolonized with Ka-11E12.

Further, as shown in FIGS. 37 to 39, it was also revealed that the Ka-11E12 colonization caused severe inflammation in 1110$^{-/-}$ mice).

These suggest that the oral K. aeromobilis strain, which is closely related to K. pneumoniae and exhibits resistances to multiple antibiotics, functions as a pathobiontic bacterium much like Kp-2H7.

Figure 40:
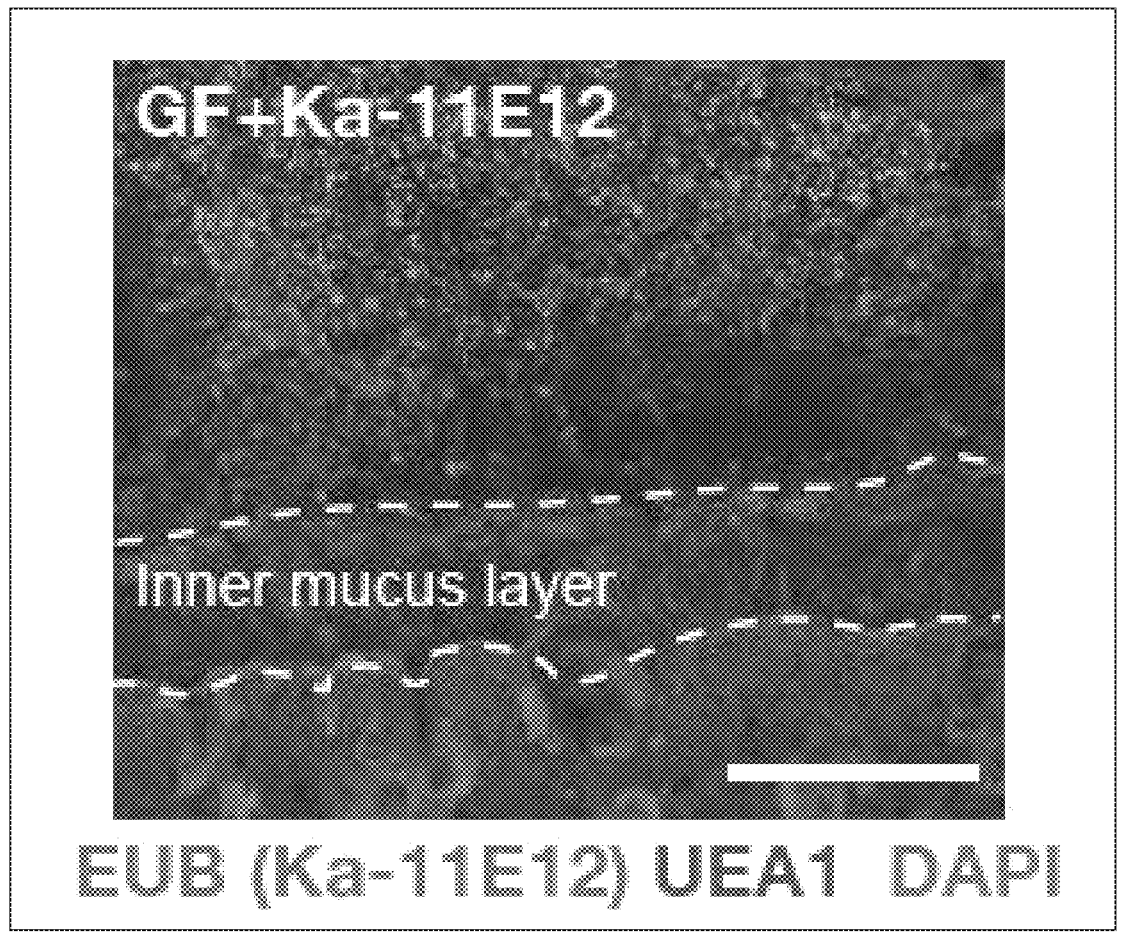
FIG. 40 is a fluorescence micrograph for illustrating the result of staining the colon of a Ka-11E12-monocolonized mouse with DAPI (indicated in blue in the figure), EUB338 FISH probe (indicated in green in the figure), and UEA1 (indicated in red in the figure). The scale bar represents 100 μm.

Furthermore, as shown in FIG. 40, FISH revealed that Ka-11E12 colonized distantly from colonic ECs similarly to Kp-2H7.

Figure 41:
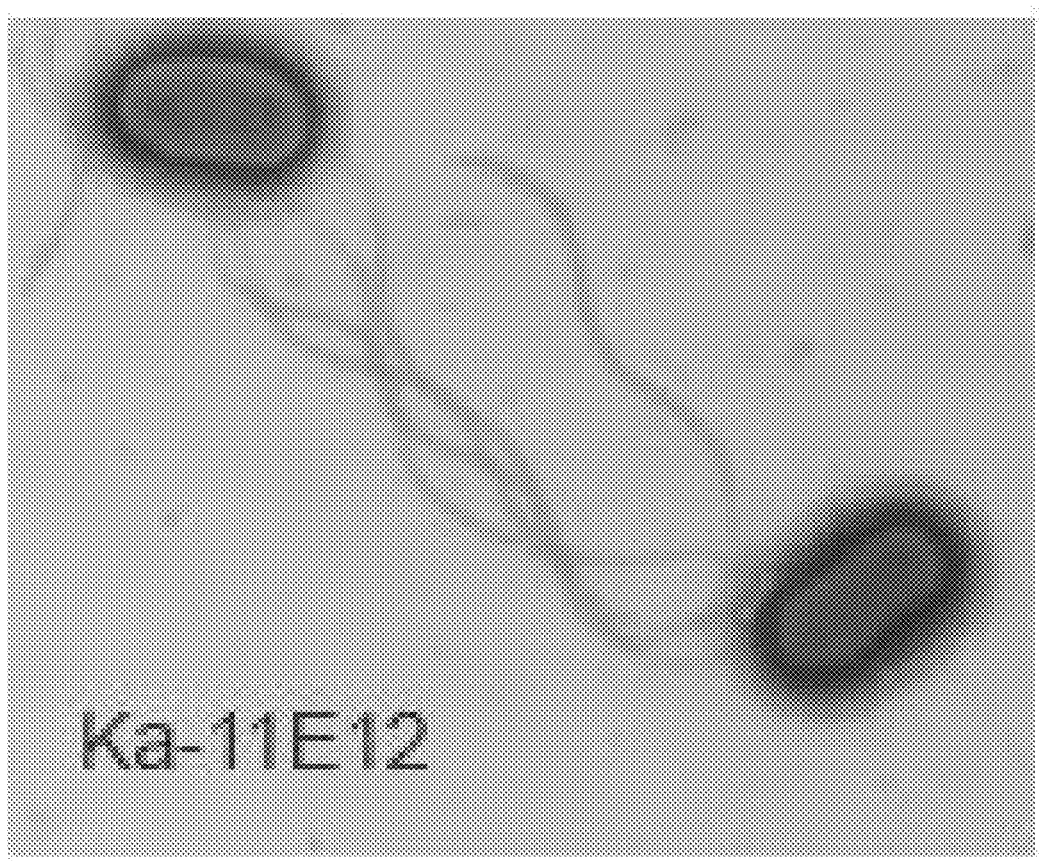
FIG. 41 is a photograph for illustrating the result of transmission electron microscope observation of in vitro cultured Ka-11E12.
Figure 42:
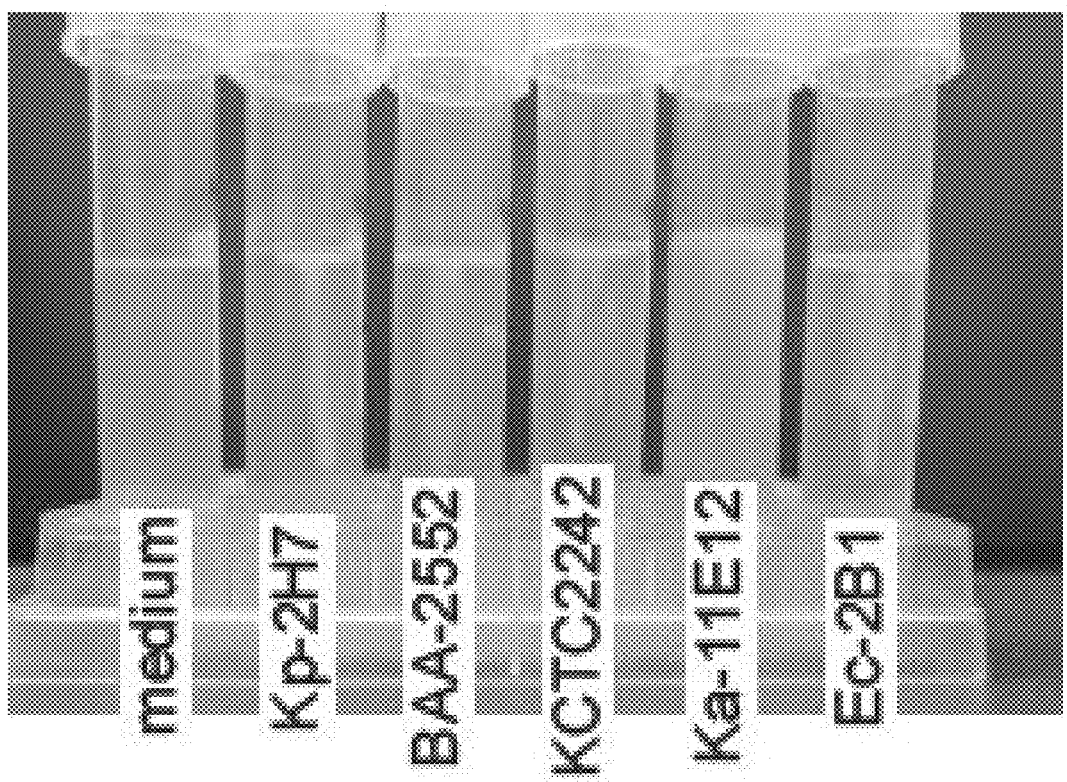
Figure 43:
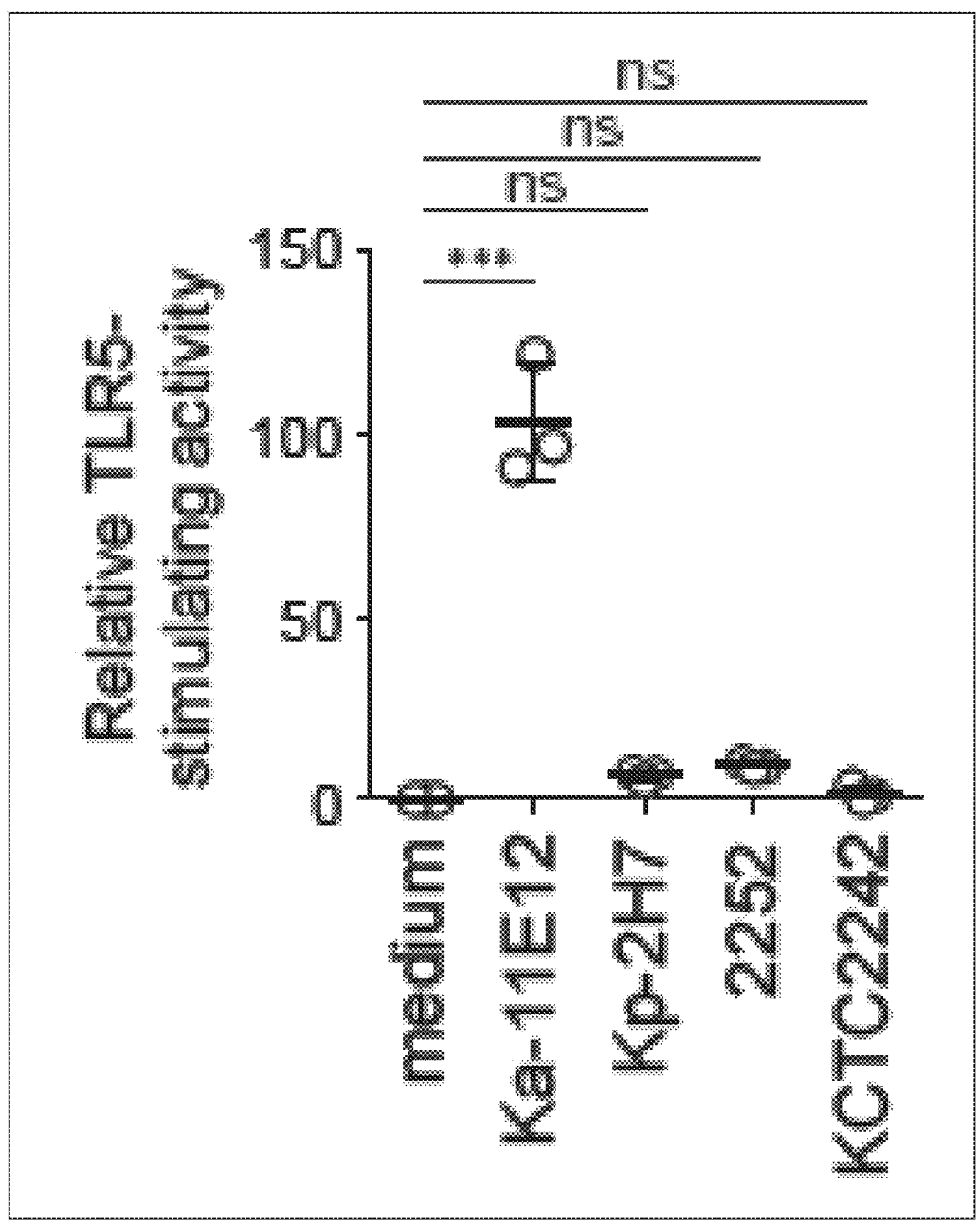
FIG. 43 is a graph for illustrating the result of luminescence assay analysis of the TLR5 activity by incubating HEK-Blue TLR5 with culture supernatants of Ka-11E12 and the like. In the graph, "medium" indicates the result of incubating HEK-Blue TLR5 without adding any bacterium. Error bars indicate means±standard deviations. ns indicates that no significant difference was found (P>0.05), *** indicates P<0.001 (based on one-way analysis of variance (ANOVA) followed by Tukey's post hoc test).
Figure 44:
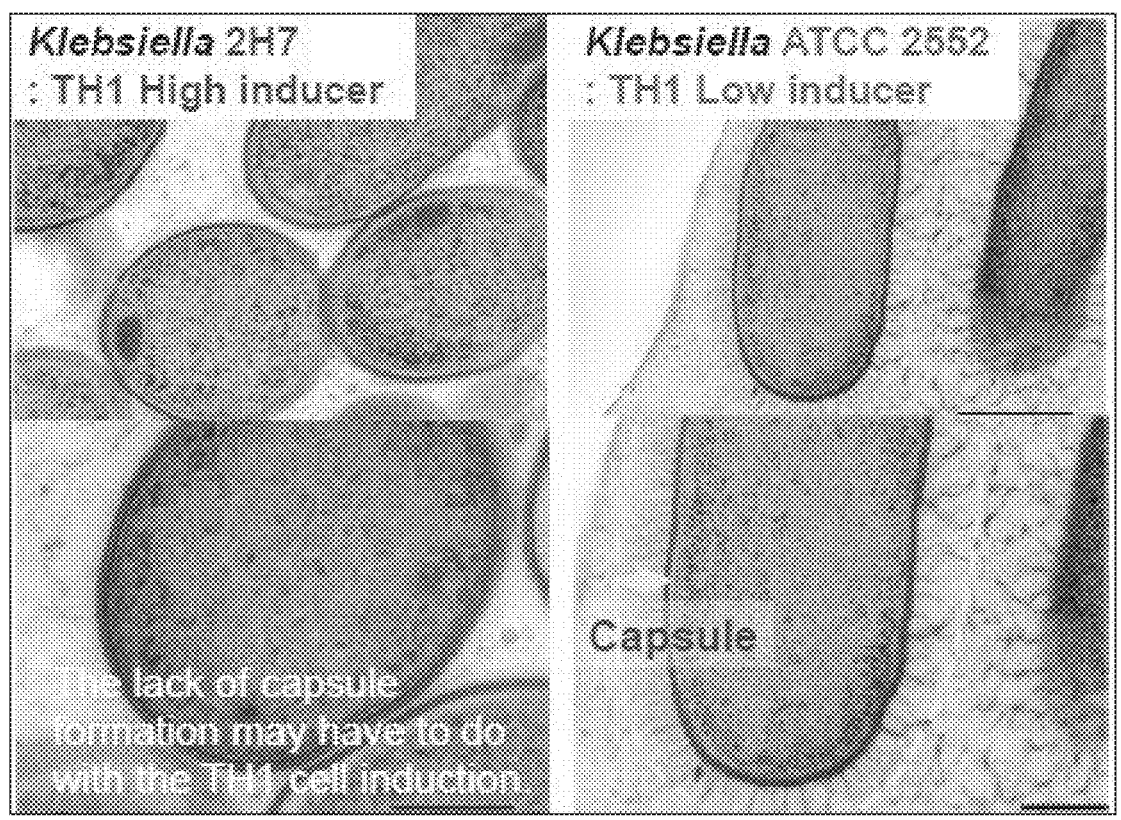
FIG. 44 shows photographs for illustrating the result of transmission electron microscope observation of Kp-2H7 (*Klebsiella* 2H7) and BAA2552 (*Klebsiella* ATCC2552).
Figure 45:
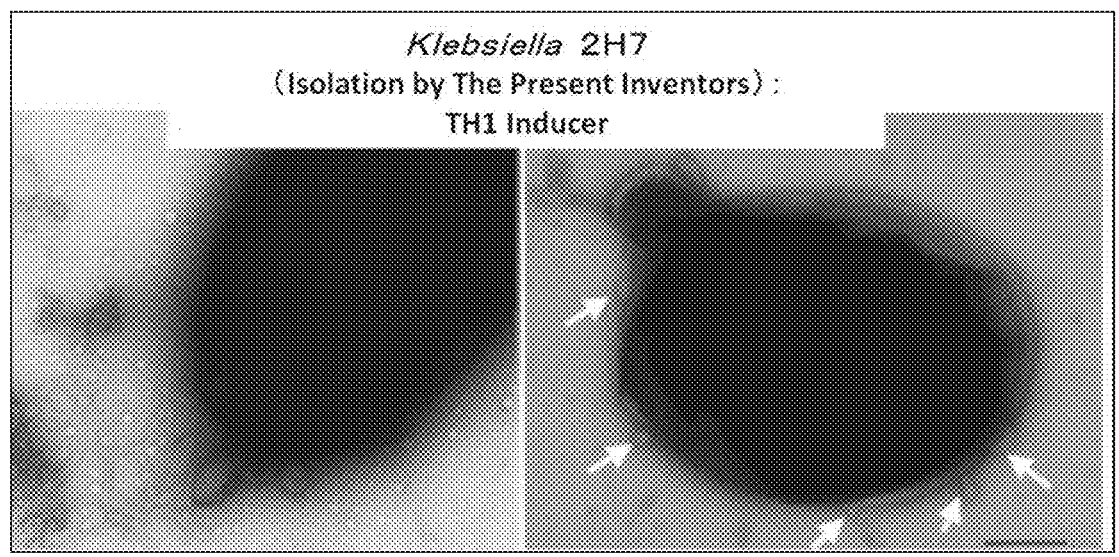
FIG. 45 shows photographs for illustrating the result of transmission electron microscope observation of in vitro cultured Kp-2H7 (*Klebsiella* 2H7) by negative staining. The arrows in the figure indicate vesicle structures (for example, outer membrane vesicles (OMV) or OMV-like structures produced by Kp-2H7) present around Kp-2H7 or budding from the bacterium.

Moreover, as shown in FIGS. 41 to 43, Ka-11E12 has a flagellar assembly system, exhibits a high motility, and also has a stimulatory action for TLR5. Meanwhile, Kp-2H7, as shown in FIGS. 44 and 45, forms no capsule, but produces outer membrane vesicles (OMV) or OMV-like structures.

Additionally, it is noteworthy that a substantial increase in Th1 cells was found in the GF+He #1 mice as shown in FIG. 33, and further that the fecal microbiota contained K. pneumoniae sequences (see FIG. 34).

Figure 46:
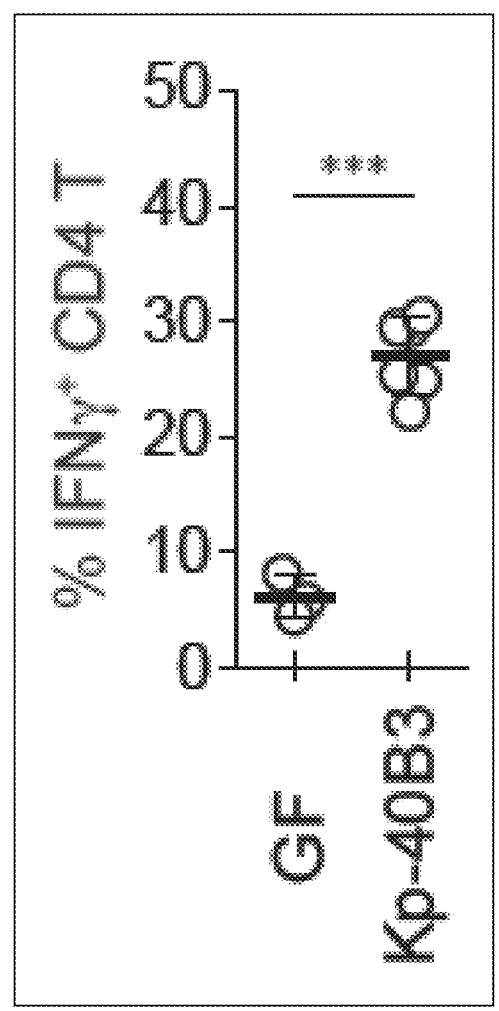
FIG. 46 is a graph showing the percentage of Th1 cells in the colonic LP of B6 mice colonized with Kp-40B3. In the graph, each point represents data on an individual mouse. Error bars indicate means±standard deviations. *** indicates P<0.001 (based on one-way analysis of variance (ANOVA) followed by Tukey's post hoc test).

Hence, a K. pneumoniae strain (Kp-40B3 strain) was isolated from cecal contents of the GF+He #1 mice, and inoculated into mice (GF+Kp-40B3). As a result, a strong accumulation of Th1 cells was found in the colon as shown in FIG. 46.

Therefore, it was revealed that a K. pneumoniae strain colonizing the healthy human oral cavity was also capable of Th1 induction when colonized in the intestine, similarly to Klebsiella species isolated from the IBD patient.

Example 4

The present inventors next examined whether Klebsiella was enriched in patients with IBD and other diseases.

Figure 47:
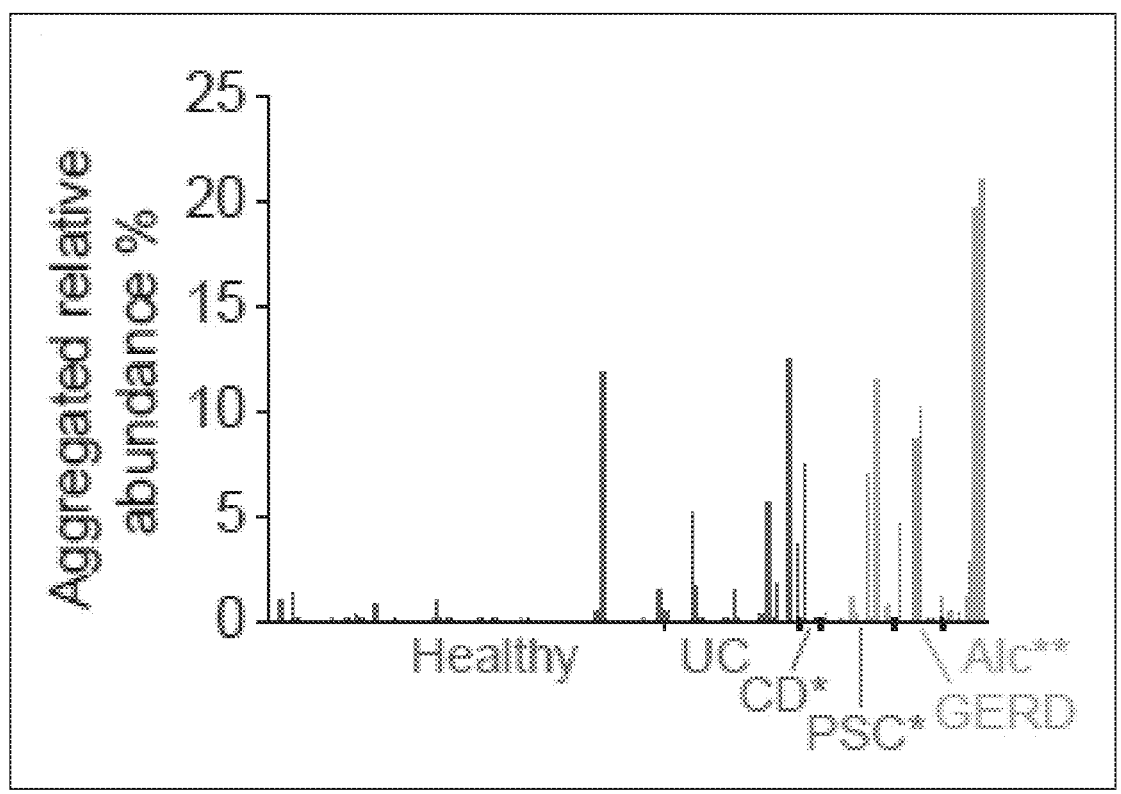
FIG. 47 is a graph showing aggregated (accumulated) relative abundances of OTUs assigned to the genus *Klebsiella* in samples derived from healthy donors and disease patients. In the graph, "UC" indicates ulcerative colitis patients, "CD" indicates Crohn's disease patients, "PSC" indicates primary sclerosing cholangitis patients, "GERD" indicates gastroesophageal reflux disease patients, and "Alc" indicates alcoholism patients. Moreover, * indicates P<0.05, and ** indicates P<0.01 (based on Wilcoxon rank-sum test).

First, 16S rRNA gene sequence databases were analyzed. As a result, it was found out as shown in FIG. 47 that the relative abundance of *Klebsiella* members was significantly higher in the patients with CD (Crohn's disease) (P=0.0157), PSC (primary sclerosing cholangitis) (P=0.0309), and alcoholism (P<0.0001) than in healthy persons.

Next, another analysis was performed by expanding the target to: the metagenome databases of intestinal microbiotas of IBD patients, non-IBD controls obtained from the Prospective Registry in IBD Study at MGH (PRISM) (see X. C. Morgan et al., Genome biology 13, R79 (2012)), and the CD cohort from University of Pennsylvania (UPenn cohort) (see J. D. Lewis et al., Cell host & microbe 18, 489-500 (2015)).

Figure 48:
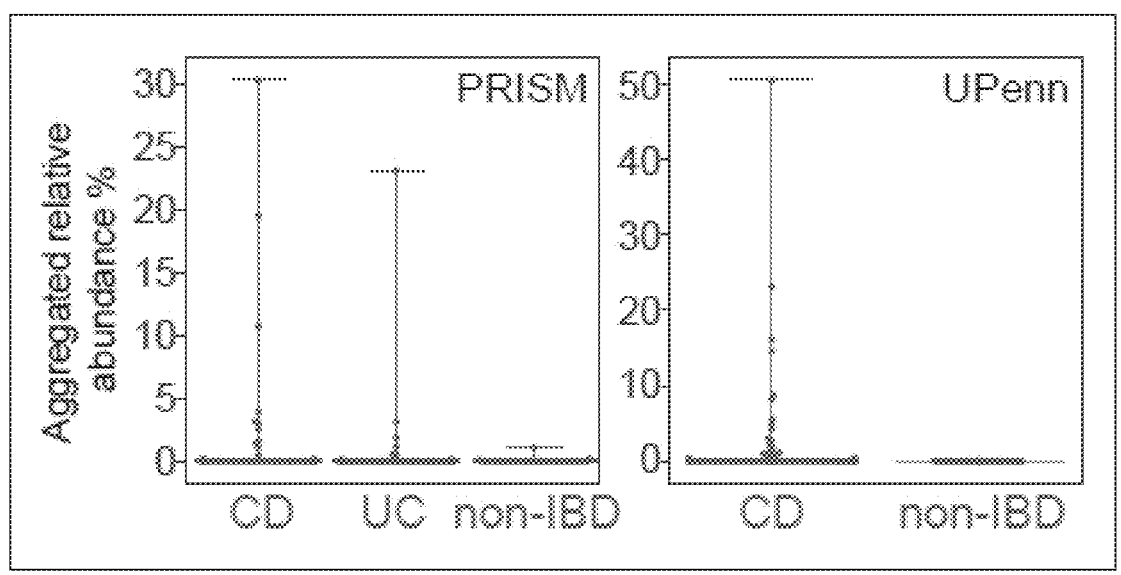
FIG. 48 shows graphs for illustrating the result of mapping the reads of samples in PRISM and UPenn cohorts to *Klebsiella* species.

As a result, it was revealed as shown in FIG. 48 that the aggregated relative abundance of *Klebsiella* species was significantly higher in the IBD patients than in the non-IBD or healthy controls across all the cohorts (P<0.01)).

Then, analyzed were genes related to Kp2H7-mediated Th1 induction in fecal microbiota of PRISM and UPenn cohorts (see FIG. 23).

Figure 49:
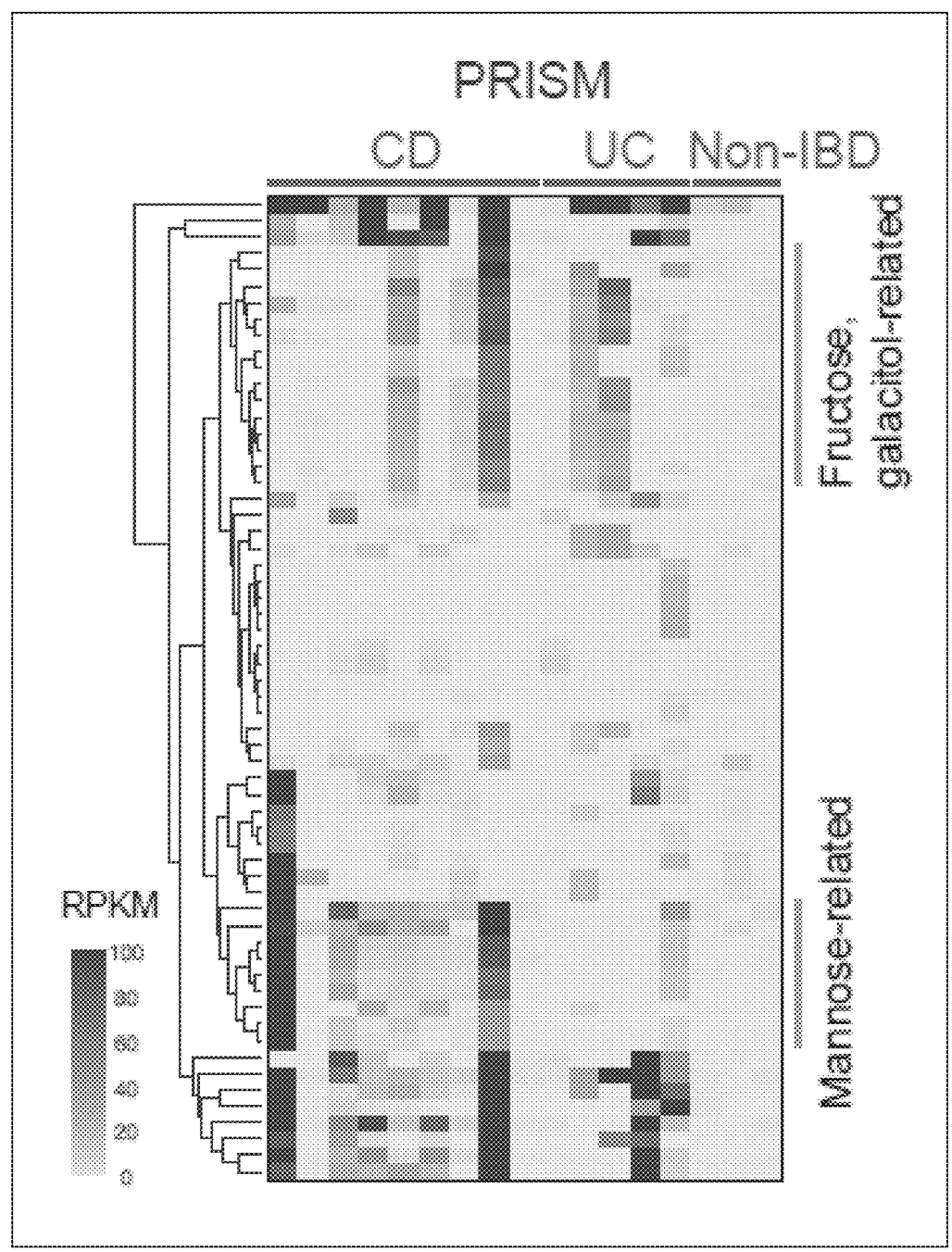
FIG. 49 is a heatmap for illustrating the result of mapping the reads of the samples in the PRISM cohort to the gene sequences related to Th1 induction. The heatmap shows values of reads per kilobase per million reads (RPKM) for the Th1-related genes.
Figure 50:
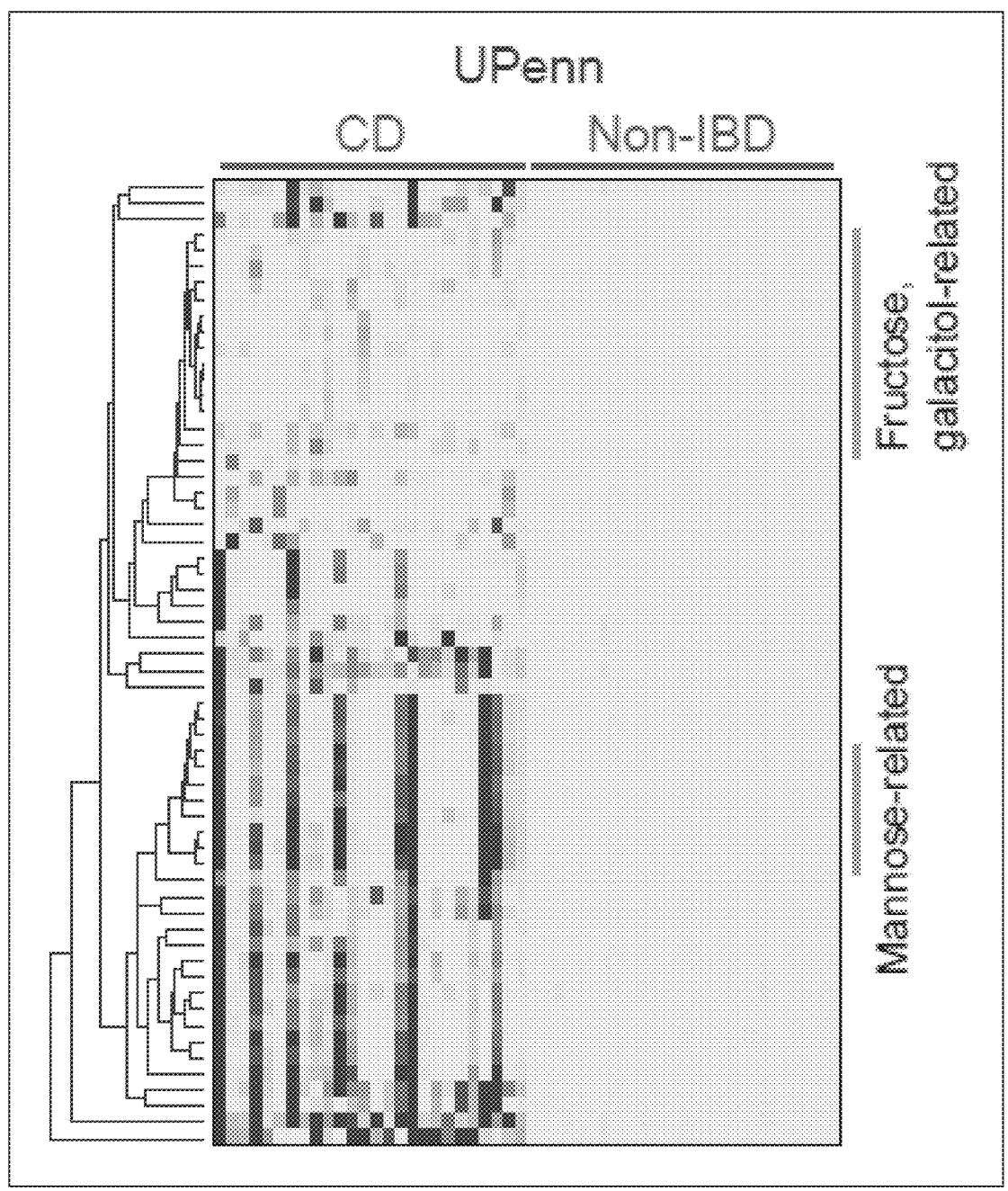
FIG. 50 is a heatmap for illustrating the result of mapping the reads of the samples in the UPenn cohort to the gene sequences related to Th1 induction. The heatmap shows RPKM values for the Th1-related genes.

As a result, the values of reads per kilobase per million reads (RPKM) for Th1-related genes were generally higher in the patient samples than in the non-IBD samples as shown in FIGS. 49 and 50.

Moreover, among the PRISM cohort, nine CD, five UC, and three non-IBD samples carried *Klebsiella*. Further, seven CD, four UC, and zero non-IBD controls were positive for Th1-related genes in their intestinal microbiotas, at around a threshold for presence of >1 average RPKM (see FIG. 49).

Among the UPenn cohort, the genes correlated with the Th1-related genes were abundantly expressed in the CD patients carrying *Klebsiella* species, but not found in the non-IBD controls (see FIG. 50).

Overall, the percentage of the Th1-related genes in the IBD patients was statistically significant in comparison with the non-IBD controls according to the analysis result by the Mann-Whitney U test (P=0.00988).

INDUSTRIAL APPLICABILITY

As has been described above, Th1 cell proliferation or activation can be induced in an intestine using bacteria such as the 2H7 strain, the 11E12 strain, the 34E1 strain, the BAA-1705 strain, the 700603 strain, and the 40B3 strain belonging to *Klebsiella*.

Thus, according to the present invention, targeting such bacteria capable of inducing Th1 cell proliferation or activation in an intestine (Th1 cell-inducible bacteria) to, for example, suppress the bacterial growth or kill the bacteria makes it possible to suppress Th1 cell proliferation or activation. Moreover, the suppression of the growth of the Th1 cell-inducible bacteria or the like makes it also possible to suppress immunity in an intestine, and consequently makes it also possible to treat, alleviate, or prevent a disease such as Crohn's disease and ulcerative colitis attributable to Th1 cells.

Further, according to the present invention, detecting the bacteria makes it also possible to test a disease attributable to Th1 cells.

In addition, according to the present invention, the use of a such Th1 cell-inducible bacterium or a physiologically active substance thereof makes it also possible to induce Th1 cell proliferation or activation, activate immunity, and consequently treat an infectious disease and enhance an anti-cancer action.

Thus, the present invention is quite useful in the drug development, and the treatment, alleviation, prevention, or diagnosis of various diseases.

[Sequence Listing Free Text]
SEQ ID NO: 1 to 35
<223> Artificially Synthesized Primer Sequence

---

The invention claimed is:

1. A method for suppressing Th1 cell proliferation or activation in a subject, the method comprising administering the subject with an antibiotic having an antibacterial activity against a bacterium that induces Th1 cell proliferation or activation in an intestine,
   wherein the bacterium is *Klebsiella pneumoniae* 2H7 (Kp-2H7) or *Klebsiella aeromobilis* 11E12 (Ka-11E12);
   the antibiotic against Kp-2H7 is one or more selected from the group consisting of meropenem, tetracycline, polymyxin-B, trimethoprim, and gentamycin; and
   the antibiotic against Ka-11E12 is one or more selected from the group consisting of meropenem, tetracycline, trimethoprim, ampicillin, gentamycin, streptomycin, and spectinomycin.

2. The method of claim 1, wherein the method is used for treating, alleviating, or preventing a disease attributable to Th1 cells in the subject.

3. The method of claim 2, wherein the disease is Crohn's disease or ulcerative colitis.

4. The method of claim 2, wherein the antibiotics is formulated for oral administration and/or delivery to the intestine or the oral cavity.

* * * * *